US012746396B2

(12) United States Patent
Yeh et al.

(10) Patent No.: US 12,746,396 B2
(45) Date of Patent: Sep. 29, 2026

(54) IMPLANTABLE DEVICE FIXATION MECHANISMS

(71) Applicant: NeuSpera Medical Inc., San Jose, CA (US)

(72) Inventors: Alexander Yeh, Los Altos Hills, CA (US); Frank W. Wang, San Bruno, CA (US); Stephen James Schellenberg, Aptos, CA (US); Anastacia Armstrong, Oakland, CA (US); Shivkumar Sabesan, South San Francisco, CA (US)

(73) Assignee: NEUSPERA MEDICAL INC., San Jose, CA (US)

( * ) Notice: Subject to any disclaimer, the term of this patent is extended or adjusted under 35 U.S.C. 154(b) by 655 days.

(21) Appl. No.: 18/025,125

(22) PCT Filed: Sep. 8, 2021

(86) PCT No.: PCT/US2021/049480

§ 371 (c)(1),
(2) Date: Mar. 7, 2023

(87) PCT Pub. No.: WO2022/056010

PCT Pub. Date: Mar. 17, 2022

(65) Prior Publication Data

US 2024/0009464 A1 Jan. 11, 2024

Related U.S. Application Data

(60) Provisional application No. 63/260,553, filed on Aug. 25, 2021, provisional application No. 63/200,973, (Continued)

(51) Int. Cl.

*A61N 1/375* (2006.01)
*A61B 5/00* (2006.01)
(Continued)

(52) U.S. Cl.

CPC ........ *A61N 1/37229* (2013.01); *A61B 5/0826* (2013.01); *A61B 5/6804* (2013.01); (Continued)

(58) Field of Classification Search

CPC ............ A61N 1/37518; A61N 1/37205; A61N 1/37516; A61N 1/3756

See application file for complete search history.

(56) References Cited

U.S. PATENT DOCUMENTS

| | | | | |
|---|---|---|---|---|
| 5,193,539 A * | 3/1993 | Schulman | A61N 1/372 607/61 |
| 2003/0045919 A1 | 3/2003 | Swoyer et al. | |

(Continued)

FOREIGN PATENT DOCUMENTS

| | | |
|---|---|---|
| AU | 2021342061 B2 | 8/2024 |
| WO | 2022056010 | 3/2022 |
| WO | WO-2022056010 A1 | 3/2022 |

OTHER PUBLICATIONS

"International Application Serial No. PCT/US2021/049480, International Preliminary Report on Patentability mailed Nov. 21, 2022", 4 pgs.

(Continued)

*Primary Examiner* — George R Evanisko

(74) *Attorney, Agent, or Firm* — SCHWEGMAN LUNDBERG & WOESSNER, P.A.

(57) ABSTRACT

Embodiments regard innovations for implantable electrostimulation devices and corresponding systems that operate using or contain the implantable electrostimulation devices. A system can include an implantable electrostimulation device. The system can further include an introducer configured to deliver the electrostimulation device to a target location inside a patient body. The introducer can comprise a migration mitigation component configured to couple with the electrostimulation device.

13 Claims, 48 Drawing Sheets

Related U.S. Application Data filed on Apr. 6, 2021, provisional application No. 63/132,861, filed on Dec. 31, 2020, provisional application No. 63/132,873, filed on Dec. 31, 2020, provisional application No. 63/132,879, filed on Dec. 31, 2020, provisional application No. 63/132,849, filed on Dec. 31, 2020, provisional application No. 63/075,545, filed on Sep. 8, 2020.

(51) Int. Cl.

| | |
|---|---|
| ***A61B 5/08*** | (2006.01) |
| ***A61N 1/36*** | (2006.01) |
| ***A61N 1/372*** | (2006.01) |
| ***A61N 1/378*** | (2006.01) |

(52) U.S. Cl.

CPC ........ *A61B 5/7275* (2013.01); *A61N 1/36139* (2013.01); *A61N 1/37518* (2017.08); *A61N 1/3787* (2013.01)

(56) References Cited

U.S. PATENT DOCUMENTS

| | | | | |
|---|---|---|---|---|
| 2003/0078618 | A1* | 4/2003 | Fey ...................... | A61B 5/6882 607/2 |
| 2005/0049542 | A1 | 3/2005 | Sigg et al. | |
| 2007/0060961 | A1 | 3/2007 | Echt et al. | |
| 2008/0132961 | A1* | 6/2008 | Jaax ..................... | A61N 1/0551 607/2 |
| 2013/0079849 | A1 | 3/2013 | Perryman et al. | |
| 2019/0247050 | A1 | 8/2019 | Goldsmith | |

OTHER PUBLICATIONS

"International Application Serial No. PCT/US2021/049480, International Search Report mailed Feb. 18, 2022", 4 pgs.

"International Application Serial No. PCT/US2021/049480, Invitation to Pay Additional Fees mailed Nov. 18, 2021", 3 pgs.

"International Application Serial No. PCT/US2021/049480, Written Opinion mailed Feb. 18, 2022", 6 pgs.

Mccullough, Mona C, et al., "Third Sacral Foramina Morphometry for Sacral Neromodulation", Female Pelvic and Reconstructive Surgery, 19(1), (2013), 23-30.

"Australian Application Serial No. 2021342061, First Examination Report mailed Feb. 12, 2024", 3 pgs.

Mccullough, Mona C, "Third Sacral Foramina Morphometry for Sacral Neromodulation", Female Pelvic and Reconstructive Surgery, 19(1), (2013), 23-30.

"European Application Serial No. 21867519.7, Extended European Search Report mailed Sep. 9, 2024", 5 pgs.

"European Application Serial No. 21867519.7, Response Filed Extended European Search Report mailed Sep. 9, 2024", 2 pgs.

* cited by examiner

IMPLANTABLE DEVICE FIXATION MECHANISMS

RELATED APPLICATIONS

This application is a U.S. National Stage Filing under 35 U.S.C. 371 from International Application No. PCT/US2021/049480, filed on Sep. 8, 2021, and published as WO 2022/056010 on Mar. 17, 2022, which application claims the benefit of priority to the following United States Provisional Patent Applications, which are all incorporated herein by reference in their entireties: U.S. Provisional Patent Application No. 63/075,545 titled "Neuromodulation Modification Based on Sensor Feedback" and filed on Sep. 8, 2020; U.S. Provisional Patent Application No. 63/132,849 titled "Parameter Cycling for Deeply Implanted Wireless Device" and filed on Dec. 31, 2020; U.S. Provisional Patent Application No. 63/132,861 titled "Epidural Placement for Wireless Implant" and filed on Dec. 31, 2020; U.S. Provisional Patent Application No. 63/132,873 titled "Stable Placement of Wireless Implantable Device" and filed on Dec. 31, 2020; U.S. Provisional Patent Application No. 63/132,879 titled "Increased Strain Relief for Wireless Implant" and filed on Dec. 31, 2020; U.S. Provisional Patent Application No. 63/200,973 titled "Garment with Attached Pocket" and filed on Apr. 6, 2021; and U.S. Provisional Patent Application No. 63/260,553 titled "Implantable Device Fixation and Strain Relief Techniques" and filed on Aug. 25, 2021.

BACKGROUND

Implantable devices can provide neuromodulation therapy to neural targets in a patient body. In some examples, wireless implantable devices can operate using near field power signals or far field power signals. The former is insufficient to achieve implantation depths suitable for some treatments. The latter is insufficient to achieve stimulation with sufficient power for some treatments. Midfield devices can be better configured to balance the requirements of deeper implantations and power transfer efficiency through tissue.

Near field, far field, and other implantable device power supplies suffer from a number of disadvantages. For example, a power harvesting structure in the implanted device is typically large, such as on the order of a centimeter or more. Transmission coils provided as an external device for nearfield communications can be bulky and inflexible. Among other factors, these can present challenges or difficulties incorporating the external device into daily life. Furthermore, the intrinsic exponential decay of nearfield transmission limits miniaturization of the implanted device and limits implantation depth flexibility. Further, the radiative nature of far field coupling limits energy transfer efficiency.

Some fixation mechanisms for implantable devices can be insufficient to withstand external forces exerted thereon. Without proper fixation, an implantable device can wander or move when a sufficient external force is applied to the implantable device or to body tissue in which the device is implanted. Techniques and mechanisms for implantable device fixation are desired.

DETAILED DESCRIPTION

Generally discussed herein are devices, methods, and systems for (i) altering a neuromodulation pattern based on sensor data. The sensor can provide data regarding a patient that is receiving neuromodulation stimulation. The sensor data can be used to determine whether the neuromodulation is effective, whether to increase or decrease an amplitude, frequency, time between stimulation, duration of stimulation, or another parameter of a neuromodulation waveform. Further discussed herein are devices, methods, and systems for (ii) fixation of an implantable device after implant, such as to help reduce chances the implantable device moves appreciably after implant; (iii) implanting the implantable device in an epidural space; (iv) improving strain relief in the implantable device to help reduce stress on the implantable device; (v) implantable device stimulation pattern management to improve brain plasticity; (vi) implantable device fixation, including various device configurations that prevent or arrest migration, and various implantation techniques to help prevent migration without using an additional external fixation component, and a combination thereof, among others.

Midfield powering technology can provide power to an implanted electrostimulation device from an external power source located on or near a tissue surface, such as at an external surface of a user's skin. The user can be a clinical patient or other user. The midfield powering technology can have one or more advantages over implantable pulse generators. For example, a pulse generator can have one or more relatively large, implanted batteries and/or one or more lead systems. Midfield devices, in contrast, can include relatively small battery cells that can be configured to receive and store relatively small amounts of power. A midfield device can include one or more electrodes integrated in a unitary implantable package. The midfield devices thus do not include a lead that extends from its implant site in the body external to the body. Thus, in some examples, a midfield-powered device can provide a simpler implant procedure over other conventional devices, which can lead to a lower cost and a lower risk of infection or other implant complications. One or more of the advantages can be from an amount of power transferred to the implanted device. The ability to focus the energy from the midfield device can allow for an increase in the amount of power transferred to the implanted device. Implant procedures discussed herein can be used with lead devices, leadless devices, near field stimulation devices, far field stimulation devices, or midfield stimulation devices.

Figure 1:
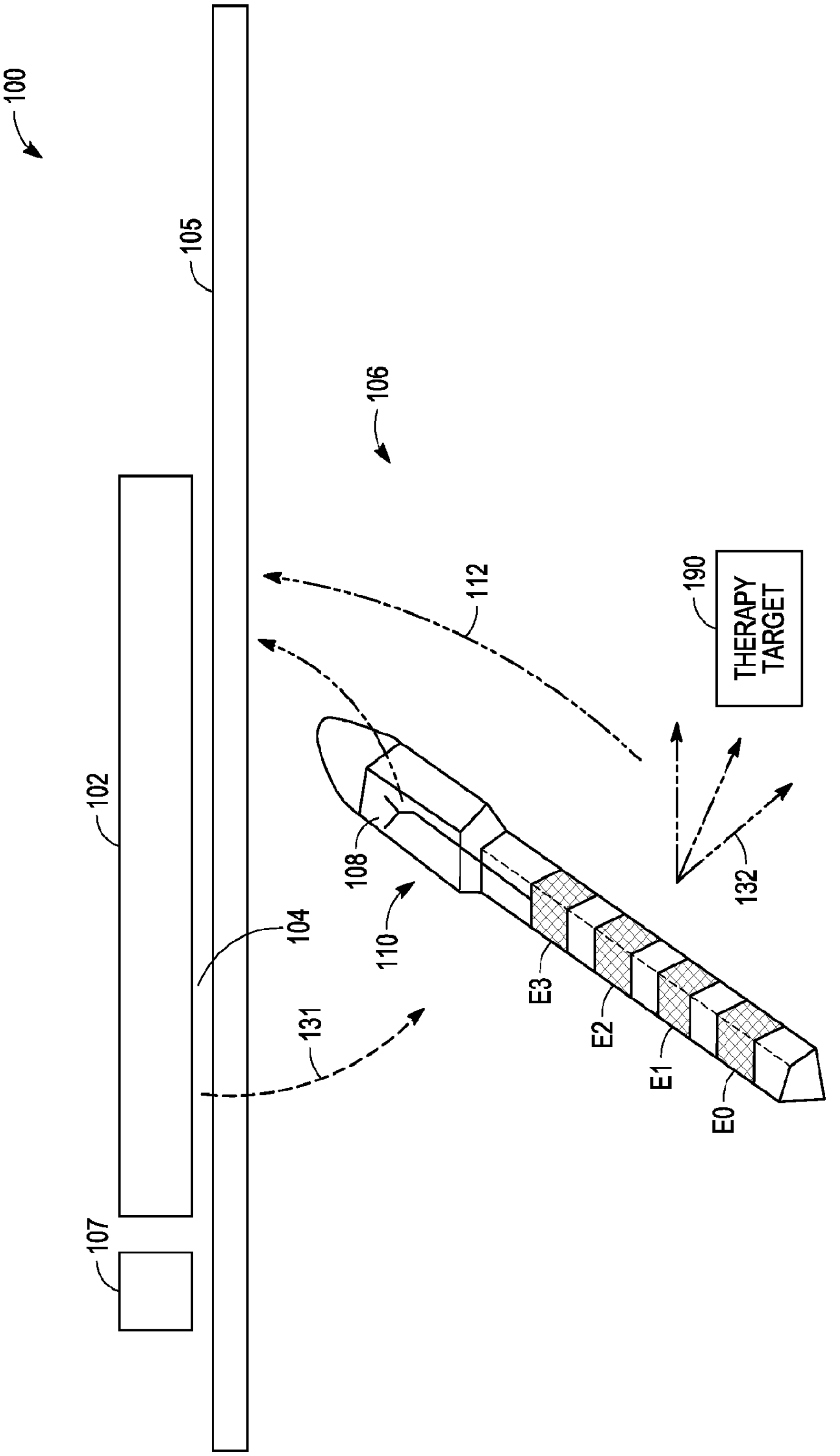
FIG. 1 illustrates, by way of example, a schematic of an embodiment of a system using wireless communication paths.

FIG. 1 illustrates, by way of example, a schematic of an embodiment of a system 100 using wireless communication paths. The system 100 includes an example of an external source 102, such as a midfield transmitter source, sometimes referred to as a midfield coupler, located at or above an interface 105 between air 104 and a higher-index material 106, such as body tissue. The external source 102 can produce a source current (e.g., an in-plane source current). The source current (e.g., in-plane source current) can generate an electric field and a magnetic field. The magnetic field can include a non-negligible component that is parallel to the surface of the source 102 and/or to a surface of the higher-index material 106 (e.g., a surface of the higher-index material 106 that faces the external source 102).

The system 100 includes an implantable device 110, such as can include a multi-polar therapy delivery device configured to be implanted in a higher-index material 106. In one or more embodiments, the implantable device 110 includes circuitry for harvesting electrical energy from the external source 102 and generating an electric field using two or more of the electrodes E0, E1, E2, E3, E4. In one or more embodiments, the implantable device 110 is implanted in tissue below the tissue-air interface 105. In FIG. 1, the implantable device 110 includes an elongate body and multiple electrodes E0, E1, E2, and E3 that are axially spaced apart along a portion of the elongate body. The implantable device 110 includes receiver and/or transmitter circuitry (see FIG. 2) that can enable communication between the implantable device 110 and the external source 102.

The various electrodes E0-E3 can be configured to deliver electrostimulation therapy to patient tissue, such as at or near a neural or muscle target. In one or more embodiments, at least one electrode can be selected for use as an anode and at least one other electrode can be selected for use as a cathode to define an electrostimulation vector. In one or more embodiments, electrode E1 is selected for use as an anode and electrode E2 is selected for use as a cathode. Together, the E1-E2 combination defines an electrostimulation vector V12. Various vectors can be configured independently to provide a neural electrostimulation therapy to the same or different tissue target, such as concurrently or at different times.

In one or more embodiments, the source 102 includes an antenna (see, e.g., FIG. 3) and the implantable device 110 includes an antenna 108 (e.g., an electric field-based or magnetic field-based antenna). The antennas can be configured (e.g., in length, width, shape, material, etc.) to transmit and receive signals at substantially the same frequency. The implantable device 110 can be configured to transmit power and/or data signals through the antenna 108 to the external source 102 and can receive power and/or data signals transmitted by the external source 102. The external source 102 and implantable device 110 can be used for transmission and/or reception of RF signals. A transmit/receive (T/R) switch can be used to switch each RF port of the external source 102 from a transmit (transmit data or power) mode to a receive (receive data) mode. A T/R switch can similarly be used to switch the implantable device 110 between transmit and receive modes.

Figure 3:
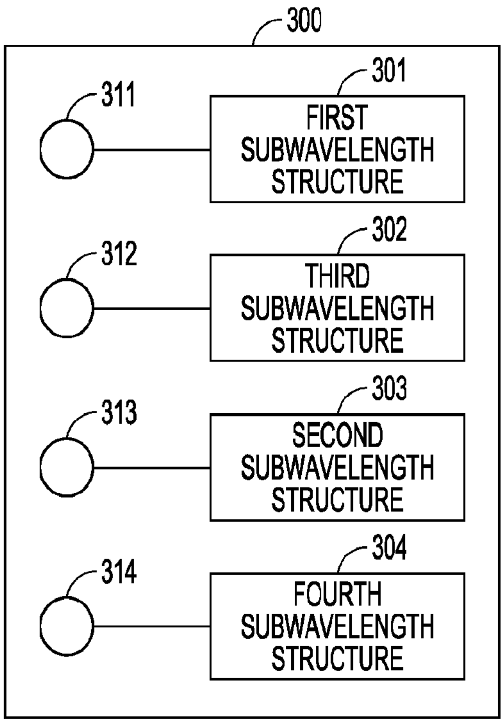
FIG. 3 illustrates, by way of example, a schematic view of an embodiment of a midfield antenna with multiple subwavelength structures.

In one or more embodiments, a receive terminal on the external source 102 can be connected to one or more components that detect a phase and/or amplitude of a received signal from the implantable device 110. The phase and amplitude information can be used to program a phase of the transmit signal, such as to be substantially the same relative phase as a signal received from the implantable device 110. To help achieve this, the external source 102 can include or use a phase-matching and/or amplitude-matching network. The phase-matching and/or amplitude matching network can be configured for use with a midfield antenna that includes multiple ports, such as shown in the embodiment of FIG. 3.

Referring again to FIG. 1, in one or more embodiments, the implantable device 110 can be configured to receive a midfield signal 131 from the external source 102. The midfield signal 131 can include power and/or data signal components. In some embodiments, a power signal component can include one or more data components embedded therein. In one or more embodiments, the midfield signal 131 includes configuration data for use by the implantable device 110. The configuration data can define, among other things, therapy signal parameters, such as a therapy signal frequency, pulse width, amplitude, or other signal waveform parameters. In one or more embodiments, the implantable device 110 can be configured to deliver an electrostimulation therapy to a therapy target 190, such as can include a neural target (e.g., a nerve), a muscle target, or other tissue target. An electrostimulation therapy delivered to the therapy target 190 can be provided using a portion of a power signal received from the external source 102. Examples of the therapy target 190 can include nerve tissue or neural targets, for example including nerve tissue or neural targets at or near cervical, thoracic, lumbar, or sacral regions of the spine, brain tissue, muscle tissue, abnormal tissue (e.g., tumor or cancerous tissue), targets corresponding to sympathetic or parasympathetic nerve systems, targets at or near peripheral nerve bundles or fibers, at or near other targets selected to treat incontinence, urinary urge, overactive bladder, fecal incontinence, constipation, pain, neuralgia, pelvic pain, movement disorders or other diseases or disorders, deep brain stimulation (DBS) therapy targets, inflammation reduction targets (e.g., L5/S1 nerves, L2 nerves, L3 nerves, or L4 nerves, or any other condition, disease or disorder (such as those other conditions, diseases, or disorders identified herein).

Delivering the electrostimulation therapy can include using a portion of a power signal received via the midfield signal 131 and providing a current signal to an electrode or an electrode pair (e.g., two or more of E0-E3), coupled to the implantable device 110, to stimulate the therapy target 190. As a result of the current signal provided to the electrode(s), a nearfield signal 132 can be generated. An electric potential difference resulting from the nearfield signal 132 can be detected remotely from the therapy delivery location. Various factors can influence where and whether the potential difference can be detected, including, among other things, characteristics of the therapy signal, a type or arrangement of the therapy delivery electrodes, and characteristics of any surrounding biologic tissue.

In one or more embodiments, the device 110 can be configured to provide a series of electrostimulation pulses to a tissue target (e.g., neural target). For example, the device 110 can provide multiple electrostimulation pulses separated in time, such as using the same or different electrostimulation vectors, to provide a therapy. In one or more embodiments, a therapy comprising multiple signals can be provided to multiple different vectors in parallel or can be provided in sequence such as to provide a series or sequence of electrostimulation pulses to the same neural target. Thus, even if one vector is more optimal than the others for eliciting a patient response, the therapy, as a whole, can be more effective than stimulating only the known-optimal vector because (1) the target may experience a rest period during periods of non-stimulation, and/or (2) stimulating the areas nearby and/or adjacent to the optimal target can elicit some patient benefit. More details regarding stimulation waveforms are provided regarding FIGS. 4-6.

The system 100 can include a sensor 107 at or near the interface 105 between air 104 and the higher-index material 106. The sensor 107 can include, among other things, one or more electrodes, an optical sensor, an accelerometer, a temperature sensor, a force sensor, a pressure sensor, or a surface electromyography (EMG) device. The sensor 107 may comprise multiple sensors (e.g., two, three, four or more than four sensors). Depending on the type of sensor(s) used, the sensor 107 can be configured to monitor electrical, muscle, or other activity near the device 110 and/or near the source 102. For example, the sensor 107 can be configured to monitor muscle activity at a tissue surface. If muscle activity greater than a specified threshold activity level is detected, then a power level of the source 102 and/or of the device 110 can be adjusted. In one or more embodiments, the sensor 107 can be coupled to or integrated with the source 102, and in other examples, the sensor 107 can be separate from, and in data communication with (e.g., using a wired or wireless electrical coupling or connection), the source 102 and/or the device 110.

In one or more embodiments, the external source 102 provides a midfield signal 131 including power and/or data signals to the implantable device 110. The midfield signal 131 includes a signal (e.g., an RF signal) having various or adjustable amplitude, frequency, phase, and/or other signal characteristics. The implantable device 110 can include an antenna, such as described below, that can receive the midfield signal 131 and, based on characteristics of receiver circuitry in the implantable device 110, can modulate the received signal at the antenna to thereby generate a backscatter signal. In one or more embodiments, the implantable device 110 can encode information in the backscatter signal 112, such as information about a characteristic of the implantable device 110 itself, about a received portion of the midfield signal 131, about a therapy provided by the implantable device 110, and/or other information. The backscatter signal 112 can be received by an antenna at the external source 102 and/or the far field sensor device 130 or can be received by another device.

Figure 2:
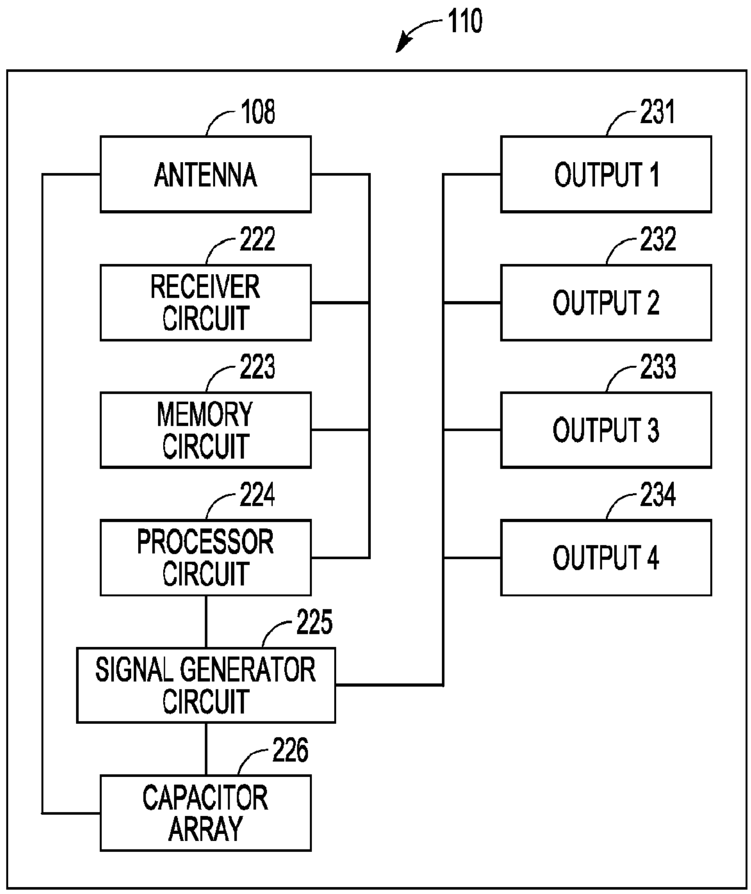
FIG. 2 illustrates, by way of example, a schematic of a multi-polar therapy delivery device, such as the device of FIG. 1.

FIG. 2 illustrates, by way of example, a schematic of a multi-polar therapy delivery device, such as the device 110 of FIG. 1. In an example, the device 110 includes an antenna 108, such as a dipole antenna, such as can be configured to receive power or data communication signals from the source 102. The device 110 can include a receiver circuit 222, such as coupled to the antenna 108. The receiver circuit 222 can receive or interpret one or more signals received via the antenna 108. In an example, the device 110 includes a processor circuit 224 and a memory circuit 223. The processor circuit 224 can be configured to act in coordination with the receiver circuit 222 to receive power or data signals from the source 102 and direct the signals to one or more of the memory circuit 223, a signal generator circuit 225, or a capacitor array 226.

In an example, the signal generator circuit 225 is configured to use power signals wirelessly received via the antenna 108 to generate a therapy signal, such as a neural electrostimulation or modulation signal. The therapy signal can include an AC signal having one or more adjustable characteristics. The one or more adjustable characteristics can include a waveform morphology shape, amplitude, phase, frequency, pulse width, timing, or other characteristic. In an example, the signal generator circuit 225 is coupled to the capacitor array 226, and the capacitor array 226 stores electrostimulation energy from the signal generator circuit 225, and one or more of the signal generator circuit 225 or the processor circuit 224 can selectively discharge stored electrostimulation energy, for example, to provide a therapy via one or more outputs of the device 110.

The device 110, as illustrated, includes multiple outputs. Each output can include output circuitry or other hardware configured to provide an electrostimulation signal to a target. In an example, the device 110 includes a first output 231 that includes, among other things, an output stage of a therapy signal amplifier or a hardware coupler for coupling the first output 231 to a therapy delivery electrode. The device 110 in the example of FIG. 2 includes second, third, and fourth outputs 232, 233, and 234, such as can each be similarly configured to the first output 231.

In an example, the signal generator circuit 225 can provide time delivery of electrostimulation signals via one or more of the first, second, third, and fourth outputs 231-234. For example, the signal generator circuit 225 can provide different electrostimulation signals to one or more of the outputs 231-234 in a serial or parallel manner. That is, in an example, the signal generator circuit 225 can be configured to provide different, discrete electrostimulation signals from each of at least two of the first through fourth outputs 231-234 in turn, such as one following another in time. In an example, the signal generator circuit 225 can be configured to provide different, discrete electrostimulation signals from each of at least two of the first through fourth outputs 231-234 concurrently, such as at least partially overlapping in time.

In an example, the processor circuit 224 and/or signal generator circuit 225 comprise portions of a state machine device. The state machine device can be configured to wirelessly receive power and data signals via the antenna 108 and, in response, release or provide an electrostimulation signal via one or more of the first-fourth outputs 231-234. In an example, such a state machine device needs not retain information about available electrostimulation settings or vectors, and instead the state machine device carries out or provides electrostimulation events substantially immediately after, and in response to, receipt of instructions from the wireless transmitter.

For example, the state machine device can be configured to receive an instruction to deliver a neural electrostimulation therapy signal, such as at a specified time or having some specified signal characteristic (e.g., amplitude, duration, etc.), and the state machine device can respond by initiating or delivering the therapy signal. At a subsequent time, the device can receive a subsequent instruction to terminate the therapy, to change a signal characteristic, or to perform some other task. Thus, the device 110 can optionally be configured to be substantially passive, or responsive to contemporaneously received instructions.

The midfield antenna 108 can be configured to provide a midfield excitation signal, such as can include RF signals having a non-negligible H-field component that is substantially parallel to an external tissue surface. In one or more embodiments, the RF signals can be adapted or selected to manipulate an evanescent field at or near a tissue surface, such as to transmit a power and/or data signal to respective different target devices (e.g., the implantable device 110) implanted in tissue. The midfield antenna 300 can be further configured to receive backscatter or other wireless signal information that can be demodulated by the demodulator circuitry. The demodulated signals can be interpreted by the processor circuitry 224 (see FIG. 2). The midfield antenna 300 can include a dipole antenna, a loop antenna, a coil antenna, a slot or strip antenna, or another antenna. The antenna 300 can be shaped and sized to receive signals in a range of between about 400 MHz and about 4 GHz (e.g., between 400 MHz and 1 GHz, between 400 MHz and 3 GHz, between 500 MHz and 2 GHz, between 1 GHz and 3 GHz, between 500 MHz and 1.5 GHz, between 1 GHz and 2 GHz, between 2 GHz and 3 GHz, overlapping ranges thereof, or any value within the recited ranges). For embodiments incorporating a dipole antenna, the midfield antenna 300 may comprise a straight dipole with two substantially straight conductors, a folded dipole, a short dipole, a cage dipole, a bow-tie dipole, or batwing dipole.

FIG. 3 illustrates, by way of example, a schematic view of an embodiment of a midfield antenna 300 with multiple subwavelength structures 301, 302, 303, and 304. The source 102 can include the midfield antenna 300. The midfield antenna 300 can include a midfield plate structure with a planar surface. The one or more subwavelength structures 301-304 can be formed in the plate structure. In the example of FIG. 3, the antenna 300 includes a first subwavelength structure 301, a second subwavelength structure 302, a third subwavelength structure 303, and a fourth subwavelength structure 304. Fewer or additional subwavelength structures can be used. The subwavelength structures can be excited individually or selectively by one or more RF ports (e.g., first through fourth RF ports 311, 312, 313, and 314) respectively coupled thereto. A "subwavelength structure" can include a hardware structure with dimensions defined relative to a wavelength of a field that is rendered and/or received by the external source 102. For example, for a given $\lambda_0$ corresponding to a signal wavelength in air, a source structure that includes one or more dimensions less than $\lambda_0$ can be considered a subwavelength structure. Various designs or configurations of subwavelength structures can be used. Some examples of a subwavelength structure can include a slot in a planar structure, or a strip or patch of a conductive sheet of substantially planar material.

Figure 4:
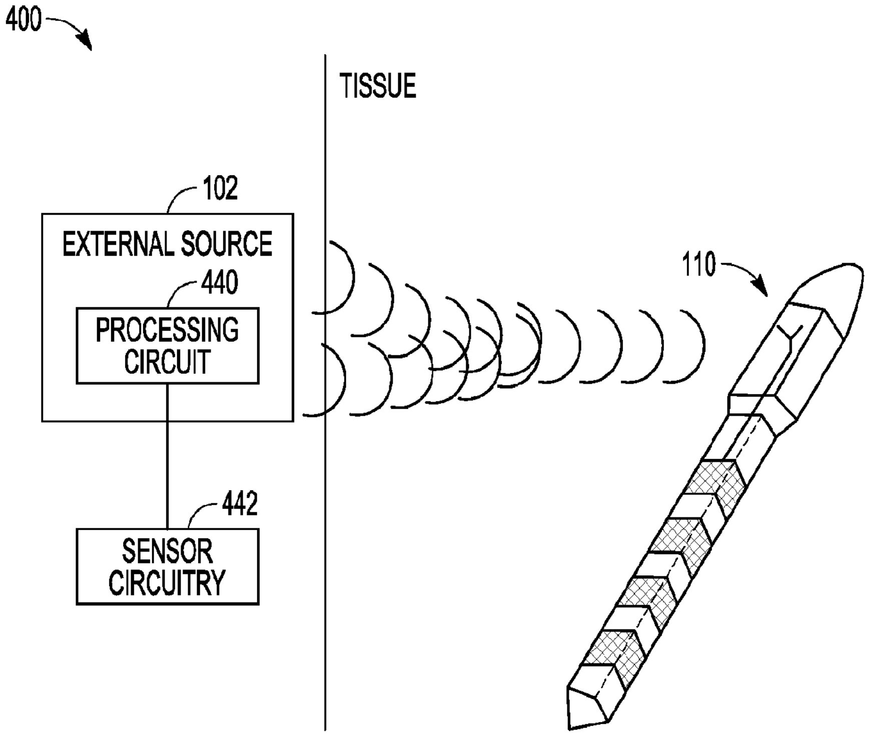
FIG. 4 illustrates, by way of example, a diagram of an embodiment of a system for therapy efficacy monitoring.

FIG. 4 illustrates, by way of example, a diagram of an embodiment of a system 400 for therapy efficacy monitoring. The system 400 as illustrated includes the external source 102, the implantable device 110 implanted in tissue, and external sensor circuitry 442. The external source 102 as illustrated includes processing circuitry 440. The processing circuitry 440 can include electric or electronic components configured to interpret data from the sensor circuitry 442. The processing circuitry 440 can alter a parameter of a neuromodulation waveform, such as delivered by the implantable device 110 to a target in the tissue, based on the data from the processing circuitry 440. The processing circuitry 440 can determine whether the data from the sensor circuitry 442 indicates an improvement in a condition being treated, a worsening of the condition being treated, a condition change, or the like. The processing circuitry 440 can then alter the neuromodulation therapy accordingly. For example, if the therapy is not effective, then a time between stimulation pulses or trains of stimulation pulses can be increased or reduced, an amplitude of the neuromodulation can be changed, a frequency of the neuromodulation can be changed, a number of pulses in a burst or pulse train can be changed, or another parameter of a neuromodulation waveform can be altered. Conversely, if the therapy is effective, one or more of a time between stimulation pulses or trains of stimulation pulses, an amplitude of a neuromodulation signal, a frequency of a neuromodulation signal, the number of pulses in a burst or pulse train, or another parameter of a neuromodulation waveform can be changed.

The sensor circuitry 442 can include a transducer configured to provide electrical signals in response to a physical property indicative of a physiologic status or environment status. The physical property can include information about one or more of a mechanical property (e.g., force, pressure, or the like), heat (e.g., temperature), motion (e.g., capacitance, magnetic field, or the like), electrical activity (e.g., resistivity, sometimes called galvanic skin response), chemical activity or status (e.g., salinity, moisture, oxygenation, or the like), or the like. The data from the sensor circuitry 442 can indicate how much pressure a patient is putting on a foot, a gait of the patient, a temperature, sweat or perspiration status, or other physiologic indicator about the patient.

As a patient's condition improves or worsens, the physical property detected by the sensory circuitry 442 can change. For example, as a user's diabetic status or other neuropathy changes, they can be more comfortable stepping. This can be detected using a pressure sensor under the foot of the patient. Increased pressure, such as relative to a prior value or baseline pressure value, can indicate that a neuromodulation is effective, and the patient's condition is improving. Decreased pressure can indicate that the neuromodulation is ineffective, and the patient's condition is getting worse.

In another example, a severity of a patient's neuropathy can be indicated by the patient's gait. A more regular gait can indicate that the patient's condition is improving. A less regular gait can indicate the patient's condition is not improving. The gait of the patient can be detected using, e.g., a multiple-axis accelerometer, magnetometer, or other sensor configured to detect motion or acceleration. A more regular gait can mean that a duration between each step event includes about the same amount of time (e.g., within about 5% for each leg), or that each leg is extending about the same distance. A less regular gait means that a time between step events is increased relative to a historic step duration or baseline, or a distance travelled by each step is increasing in variance, standard deviation, or the like, or the average distance travelled each step is not stable (e.g., the average changes by more than a threshold amount in a specified amount of time). The accelerometer can be situated in or on a patient's shoe, on (directly or indirectly) or coupled to a patient's leg, such as in a pants pocket of the patient or attached to the patient's skin, a hip (e.g., pelvic region) of the patient, a wrist of arm of the patient, or the like.

In another example, a relative neuropathy of a patient can be indicated by an amount of perspiration or sweat. If the patient is sweating more, their neuropathy can be getting worse. If the patient is sweating less, their neuropathy can be getting better. Data from a salinity or moisture sensor can help determine whether a patient is sweating more or less (relative to a baseline amount). For example, the data from the moisture or salinity sensor can indicate that a sweat volume is increasing or decreasing. The moisture or salinity sensor can be situated directly or indirectly on a foot, leg, pelvis, torso, arm, or the like.

In yet another example, a temperature of the patient can indicate whether their condition is improving or getting worse. If the temperature of the patient is increasing, the patient's condition can be getting worse. If the temperature of the patient is decreasing, the patient's condition can be getting better. A temperature sensor can be used to detect the patient's temperature. The temperature sensor can be situated in or on the patient's shoe, the patient's leg, the patient's foot, the patient's pelvis, the patient's torso, the patient's arm, the patient's neck, the patient's head, or the like.

In yet another example, a galvanic skin response of the patient can indicate whether their condition is improving or getting worse. If the galvanic skin response is increasing, the patient's condition can be getting worse. If the galvanic skin response is decreasing, the patient's condition can be getting better. The galvanic skin response sensor can be situated on or near the skin of the patient.

In yet another example, a blood oxygen level of the patient can indicate whether their condition is improving or getting worse. The blood oxygen level can be determined based on data from an oxygenation sensor. If the oxygen sensor indicates the oxygen level is increasing, the condition of the patient can be improving. If the oxygen sensor indicates the oxygen level is decreasing, the condition of the patient can be getting worse. The oxygenation sensor can be situated on or near the patient's skin, such as on the patient's foot, the patient's leg, the patient's pelvis, the patient's torso, the patient's arm (e.g., the patient's hand or finger), the patient's neck, the patient's head, or the like.

The external source 102 can receive data from the sensor circuitry 442 and, in response, the external source 102 can provide a communication to the implantable device 110. The communication can cause the implantable device 110 to provide neurostimulation with specific waveform parameters (e.g., amplitude, time between pulses or trains, number of pulses, frequency, or the like). The waveform parameters can be selected based on an algorithm performed by the processing circuitry 440 using the information from the sensor circuitry 442, such as from one or more of the sensors. In this way, the data from the sensor circuitry 442 can inform the operations of the implantable device 110. The external source 102 can thus alter the neuromodulation based on the efficacy of the neuromodulation.

For example, if the data from the sensor circuitry 442 indicates the neuromodulation is effective (the patient's condition is improving) then the external source 102 can cause the implantable device 110 to continue the same neuromodulation. If the data from the sensor circuitry 442 indicates the neuromodulation is not effective (the patient's condition is getting worse or not getting better) then the external source 102 can cause the implantable device 110 to provide neurostimulation therapy with one or more different waveform parameters than was used by an immediately prior neurostimulation therapy.

The sensor circuitry 442 can include a wired or wireless communicative coupling to the external source 102. Data can be provided from the sensor circuitry 442 to the external source 102 in a synchronous or asynchronous manner. In the asynchronous manner, the sensor circuitry 442 can provide the data as it generates it, after it generates a specified amount of data, after a specified amount of time has elapsed, a combination thereof, or the like. In the synchronous manner, the sensor circuitry 442 can provide the data at specified times or time intervals, upon request, a combination thereof, or the like.

Figure 5:
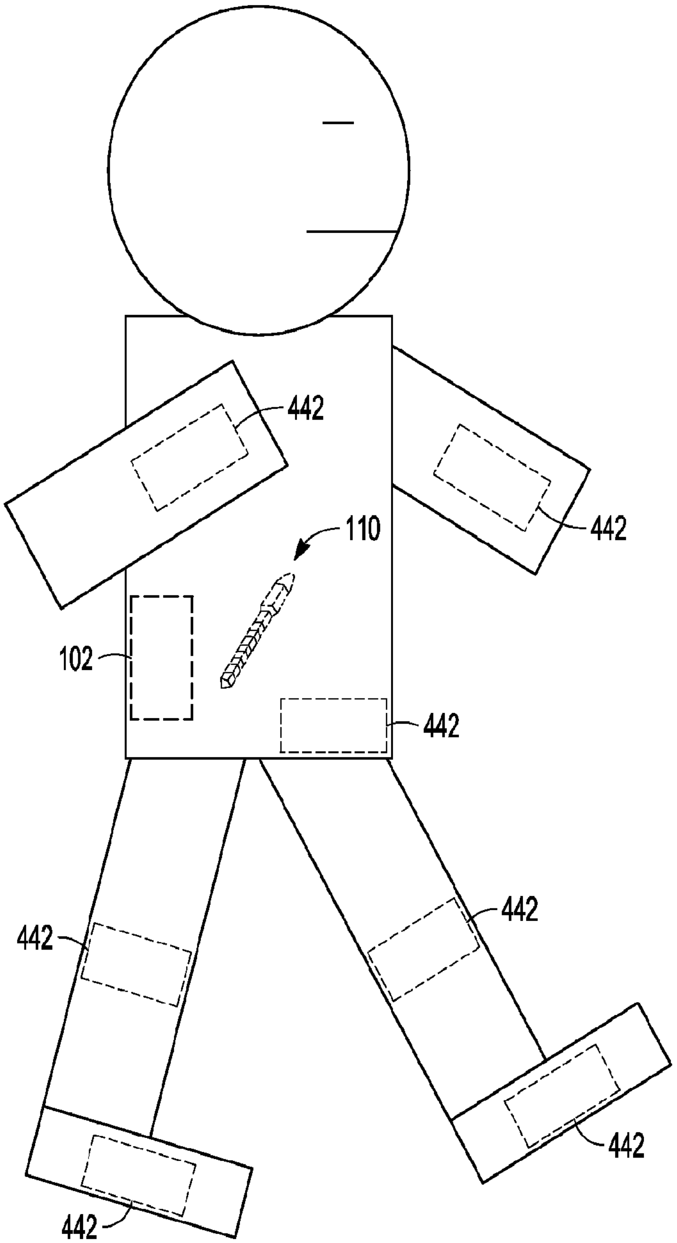
FIG. 5 illustrates, by way of example, a diagram of an embodiment of a patient and the system of FIG. 4.

FIG. 5 illustrates, by way of example, a diagram of an embodiment of a patient using or wearing the system 400 of FIG. 4. The diagram shows the sensor circuitry 442 in various locations on the user. The sensor circuitry 442 can be situated on or near the foot, ankle, leg, knee, pelvis, hip, torso, arm, wrist, hand, neck, shoulder, abdomen, back, head, or the like. The sensor circuitry 442 can include one or multiple sensors configured to be used individually or in combination. For example, sensor circuitry 442 can be situated to monitor movement of each foot or leg and on skin somewhere on the body. That is, one or more sensed indications (e.g., temperature, motion, chemical, electrical, or the like) of the patient condition can be monitored by one or more of the various sensor circuitry 442.

The external source 102 can be situated in a pocket or otherwise situated to provide electromagnetic waves to the implantable device 110. The implantable device 110, as illustrated, is implanted through a sacral foramen of the pelvis, but can be implanted elsewhere. The external source 102 can provide signals to the implantable device 110 that provide electrical power for the implantable device 110. The power signals can be used by the external source 102 to provide neuromodulation stimulation of a therapy target (a nerve, for example). The external source 102 can provide signals to the implantable device 110 that cause the implantable device 110 to adjust a parameter (e.g., frequency, amplitude, time between stimulation, number of pulses or duration of the stimulation, or the like) of a waveform of the neuromodulation.

The external source 102 can receive data from the sensor circuitry 442 and adjust a parameter of the neuromodulation accordingly. Adjusting the parameter can include issuing a communication to the implantable device 110 that causes the implantable device 110 to adjust the parameter. The parameter of the neuromodulation can be adjusted as previously discussed. The implantable device 110, in some embodiments, can be a sort of secondary device that is configured by or is responsive to communications form the external source 102 or primary device. In these embodiments, the implantable device 110 can include only a receive antenna (and corresponding demodulation circuitry). In these embodiments, the implantable device 110 may not include a transmit antenna (and corresponding modulation circuitry).

Figure 6:
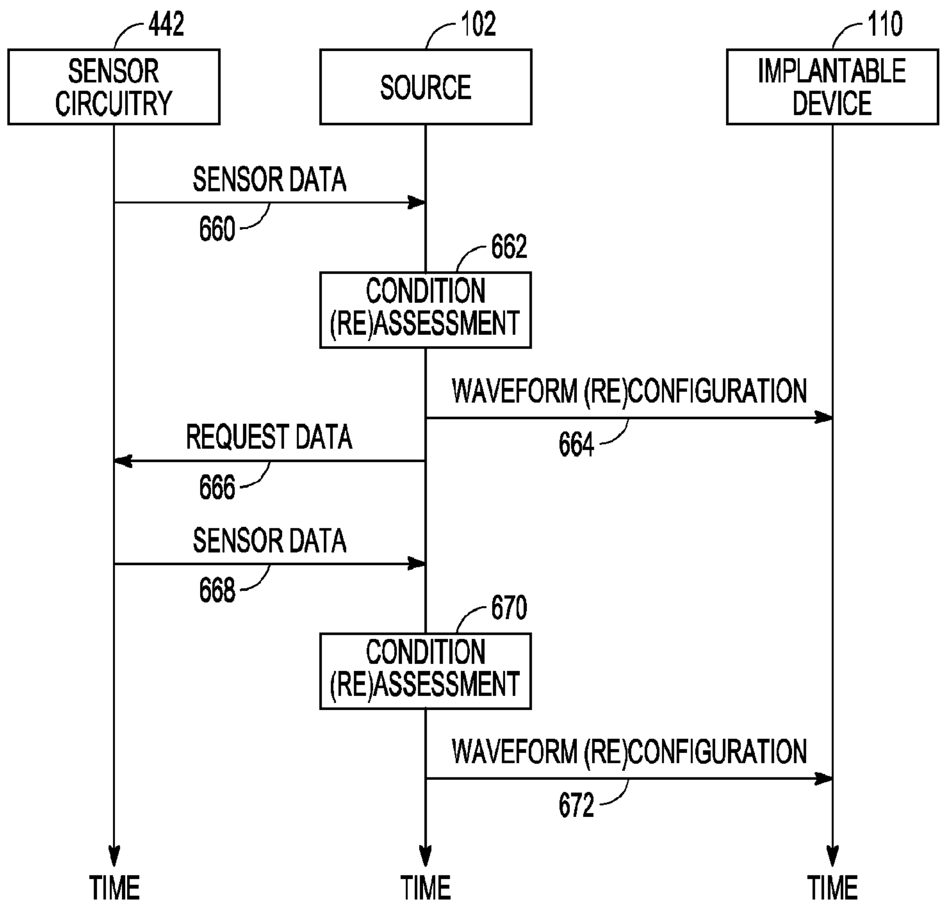
FIG. 6 illustrates, by way of example, a diagram showing communications and operations of sensor circuitry, a source, and an implantable device.

FIG. 6 illustrates, by way of example, a communication diagram of an embodiment of communications and operations of the sensor circuitry 442, the source 102, and the implantable device 110. The sensor circuitry 442 can include a communicative coupling (wired or wireless) to the external source 102. The external source 102 can be wirelessly coupled to the implantable device. The wireless coupling can include a midfield coupling as discussed previously. The sensor circuitry 442 can generate sensor data that is indicative of a physical property of the user. The physical properties are discussed previously. The sensor circuitry 442 can include memory that stores the sensor data. The sensor circuitry 442 can provide sensor data to the external source 102 as the data is generated by the sensor circuitry 442, such as when or if the sensor circuitry 442 does not include the memory.

The sensor circuitry 442 can issue a synchronous or asynchronous communication 660 of sensor data to the source 102. The sensor communication 660 can include sensor data in communication 668 that uniquely identifies the sensor circuitry 442 or source (e.g., if more than one sensor circuitry is present), the sensor data payload, a time indicating when the sensor data was generated, or the like. The communication 660 can include the sensor data generated since the last time sensor data was provided to the source 102. The communication 660 can be provided after a specified period of time has elapsed, or when a specified amount of sensor data accrues in the memory of the sensory circuitry 442, at a specified time, upon request by the source 102, or the like (e.g., by issuing a request data communication 666).

The external source 102 can perform a condition (re) assessment operation 662 based on the sensor data in the communication 660, and optionally further based on historical or other previously received sensor data. The condition (re)assessment operation 662 can include determining whether the condition of the user is improving, staying the same, or getting worse. The operation 662 can include determining whether a change is detected in one or more of a sensed pressure, salinity, moisture, temperature, oxygen level, motion or range of motion, resistivity, or other physiologic status indicator.

In response to the external source 102 determining the condition is worsening, staying the same, or improving, the external source 102 can issue a waveform (re)configuration communication 664 to the implantable device 110. The waveform (re)configuration communication 664 can cause the signal generator circuit 225 (see FIG. 2) to generate stimulation with a different waveform parameter than was used in, e.g., an immediately prior stimulation. The waveform (re)configuration communication 664 can include a command that causes the signal generator circuit 225 to generate the stimulation with the different waveform parameter.

The source 102 can issue a communication 666 to request data from the sensor circuitry 442. The communications 668, 672 are similar to the communications 660, 664, respectively. The operation 670 is similar to the operation 662. The request data communication 666 can include a command requesting the sensor circuitry 442 provide the sensor data. The request data communication 666 can include an identification indicating the sensor circuitry 442 associated with the command (e.g., if more than one sensor circuitry 442 is present).

Parameter Cycling for Deeply Implanted Wireless Device (Brain Plasticity)

Generally discussed herein are devices, methods, and systems for initializing an implantable device and optimizing an electrostimulation therapy provided by the device. In an example, the implantable device can be configured for implantation at or near a nerve target in a sacral or genital area, such as for treatment of overactive bladder (OAB). Other targets can be reached, and other treatments can similarly be provided using the same or other implantable device.

Figure 7:
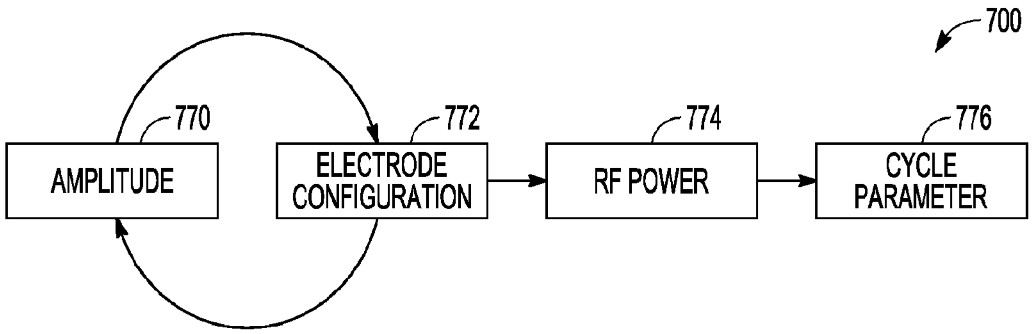
FIG. 7 illustrates generally an example of a device programming algorithm.

FIG. 7 illustrates generally an example of a device programming algorithm 700. The device programming algorithm 700 can describe a procedure for initializing an implantable neurostimulation device when it is newly implanted in a patient. In an example, the device programming algorithm 700 includes initializing the device to use a relatively high power, broadest electric field configuration. This is contrary to the conventional technique of initializing battery-powered devices, where minimizing power consumption to extend battery life is paramount. Since the present systems and methods can use a highly efficient external midfield power source, concerns about power consumption can be minimized.

In an example, the device programming algorithm 700 includes selecting an electrostimulation amplitude at block 770 and selecting an electrode configuration at block 772. In the example, block 770 and block 772 can be processed or performed together because different electrode configurations can use different stimulation signals. The selected amplitude can be a function of, among other things, patient response, tissue type at the electrode or implantation site, or distance between the selected electrode(s) and the neural target. In an example, selecting an electrostimulation amplitude at block 770 can include selecting a therapy parameter such as an electrostimulation signal waveform, duty cycle, or other therapy parameter.

In an example, block 770 and block 772 can include changing amplitude and/or electrode configuration parameters to determine a sensory threshold of the patient, that is, a threshold at which the patient can detect or feel the stimulation. In an example, block 770 can include setting an electrostimulation amplitude at a level that exceeds the threshold. In an example, block 772 can include selecting an electrode configuration for which the patient reports a central sensation and/or a genital sensation. Block 772 can further include selecting an electrode configuration that produces a broadest electric field (e.g., due to the positions of the electrodes used to produce the field, due to the adjoining tissue characteristics, due to the amplitude or other stimulation signal characteristics used, or due to other factors). In an example, block 772 can further include selecting an electrode configuration that does not produce adverse stimulation, such as can produce undesired muscle activations or others undesired effects.

Following block 772, the device programming algorithm 700 can include determining or updating a power transmission characteristic at block 774. For example, block 774 can include changing a parameter of a power transmission signal provided by an external device to an implanted device. The parameter can include, for example, an amplitude, duration, direction (i.e., of a steered or focused midfield power signal), duty cycle, or another parameter, of the transmitted signal. In an example, block 774 can include balancing the requirements or effects of heat generation and positioning of the external device relative to the implanted device.

Following block 774, the device programming algorithm 700 can include cycling one or more therapy parameters at block 776. For example, block 776 can include changing a frequency of stimulation or frequency of therapy events or changing a duty cycle of a therapy signal. In an example, block 776 can include changing a duration of stimulation. In an example, changing a duty cycle or pulse width of a therapy signal can help allow greater amplitude therapy signals without causing an adverse sensation to the patient.

In an example, block 776 can include cycling parameters when, for example, a power transmission threshold is met or exceeded. For example, if a particular therapy uses more than 50% of the power available from the external source, then block 776 can be used to change a stimulation parameter. For example, when more than 50% of the power is used, then therapy can be modulated (e.g., turned off and on) in a time-multiplexed manner, for example, to help limit power consumption and heat generation, for example without adversely affecting the therapeutic effect on the patient. Table 1 illustrates an example of how therapy on-time can be modulated or adjusted based on RF power level.

TABLE 1

Therapy modulation based on RF Power Level.

| RF Power Level | Therapy Event On-time in seconds, e.g., with 3 s off between events |
|---|---|
| 100% | 3 |
| 95% | 3 |
| 90% | 3 |
| 85% | 4 |

TABLE 1-continued

Therapy modulation based on RF Power Level.

| RF Power Level | Therapy Event On-time in seconds, e.g., with 3 s off between events |
|---|---|
| 80% | 5 |
| 75% | 6 |
| 70% | 7 |
| 65% | 10 |
| 60% | 15 |
| 55% | 30 |
| 50% | Any |

Figure 8:
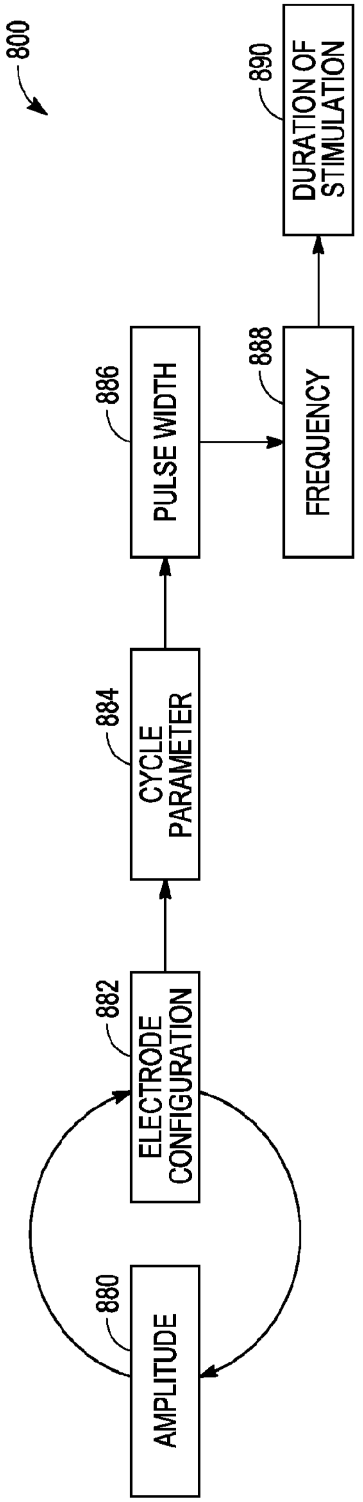
FIG. 8 illustrates generally an example of a device optimization algorithm.

FIG. 8 illustrates generally an example of a device optimization algorithm 800. In an example, the device optimization algorithm 800 can be performed after implantation of a midfield device and after, for example, the device programming algorithm 700 from FIG. 7. In an example, the device optimization algorithm 800 can be performed to adjust device parameters for non-responders or weak responders following initialization under the device programming algorithm 700.

In the example of FIG. 8, block 880 and block 882 can correspond generally to block 770 and block 772, respectively, from the example of FIG. 7. In an example, block 880 and block 882 correspond generally to a first treatment phase (Phase 1). Patient response to therapy during Phase 1 can be monitored, for example, with a 72-hour bladder diary around one week after implantation. An objective during Phase 1 can be to maximize activation of the patient's pelvic floor while remaining well-tolerated by the patient (i.e., substantially no adverse activations or discomfort to the patient).

At block 884, parameter cycling can begin. Various device or therapy parameters can be cycled or changed, for example, if a patient is not responding to an initial therapy or if the patient reports improvement by less than a threshold improvement amount. At block 884, such as corresponding to a second treatment phase (Phase 2), patient response can be monitored using a bladder diary, e.g., over the course of 72 hours. Therapy can be cycled, for example, at regular intervals such as 3 seconds on, and 3 seconds off, for different therapy events. During Phase 2, an objective can be to minimize therapy acclimatization by choosing therapy parameters that are at or above a perception threshold of the patient. By choosing such parameters, patient brain plasticity can be maximized to thereby recognize the effects and benefits of the therapy.

At block 886, a third treatment phase (Phase 3) can include changing a therapy signal pulse width (PW). In an example, changing a PW can help change selectivity of nerve fibers to efferent fibers. In an example, block 886 can include increasing a PW to, e.g., 450 microseconds, such as from a lesser initial PW.

At block 888, a fourth treatment phase (Phase 4) can include changing a therapy signal frequency. In an example, changing a frequency can help change an afferent sensation experienced by the patient. In an example, block 888 can include increasing a frequency to, e.g., 31 Hz, such as from a lesser initial frequency.

At block 890, a fifth treatment phase (Phase 5) can include changing a duration of a stimulation therapy event. In an example, changing a duration increases a therapy dosage provided to a patient, such as toward a continuous stimulation dosage. In an example, block 890 can include increasing a duration of a stimulation therapy event to 4, 6, 8, or more hours each day. In an example, the dosage can be increased gradually or rapidly or at a pace determined by the patient.

The example of FIG. 8 includes treatment Phases 1 through 5 in sequence. Any one or more of the phases may be provided or adjusted concurrently with another phase, or in a different order than in the illustrated embodiment.

Figure 9:
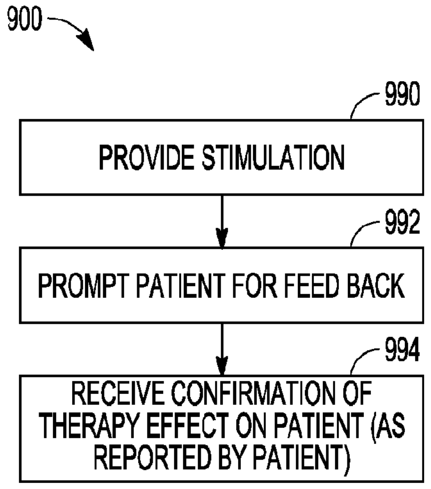
FIG. 9 illustrates generally an example of a method that can help enhance plasticity in the brain and optimize an effect of a patient therapy.

FIG. 9 illustrates generally an example of a first method 900 that can be performed to enhance plasticity in the brain to help optimize an effect of a patient therapy. The first method 900 can include providing stimulation at block 990, and then prompting a patient for feedback at block 992. For example, block 992 can include prompting the patient to determine whether the stimulation was felt or perceived, and if it was felt or perceived, then to determine whether the sensation was painful, pleasant, or somewhere in between. At block 994, the method 900 can include receiving the response information from the patient about the presence or absence of a sensation and any qualities of that sensation.

In an example, the first method 900 can be performed periodically (e.g., every 30 minutes, or at other irregular intervals) to establish a therapy diary. By prompting the patient occasionally to observe whether they are sensing a therapy event, the patient can be urged to "tune in" to the therapy and to any effect of the therapy. In an example, block 992 can be coordinated with therapy events (e.g., with intermittent or periodic therapy events). In an example, patient interfaces and other systems and methods for facilitating patient check-ins or feedback is described in PCT application PCT/US2020/039545, filed Jun. 25, 2020, which is hereby incorporated herein by reference in its entirety.

In an example, if information received from the patient (e.g., at block 994) indicates that the patient is not responding or is weakly responding to therapy, then the device optimization algorithm 800 can be performed.

In an example, block 992 can include providing a stimulus to the patient, such as using the implanted therapy delivery device or using an external device. The stimulus can include an audible signal, visual signal, haptic signal, or a therapy signal (e.g., with increased amplitude).

Figure 10:
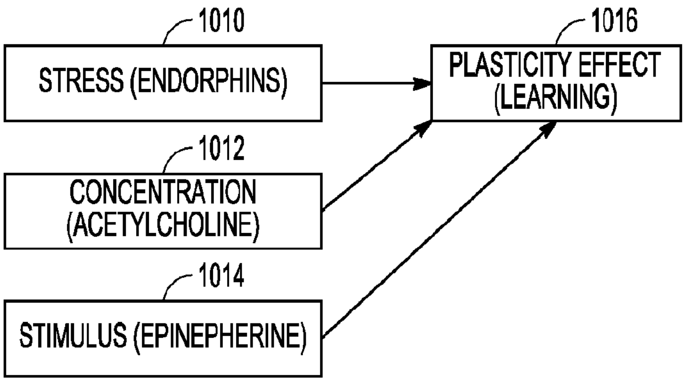
FIG. 10 illustrates generally an example that illustrates effecting brain plasticity.

FIG. 10 illustrates generally an example that illustrates how therapy can be augmented by leveraging brain plasticity. Plasticity, or neuroplasticity, refers generally to an ability of the brain to adapt or change over time. A degree or magnitude of plasticity 1016, or change in the brain, can be a function of stress (e.g., endorphins) 1010, of a concentration of various body chemicals or neurotransmitters (e.g., acetylcholine) 1012, and of stimulus (e.g., epinephrine) 1014, among other things. In an example, a neurostimulation device can provide a stimulus that can help encourage plasticity toward recognizing a neurostimulation therapy and the effects of such therapy.

Epidural Placement for Wireless Implant

Generally discussed herein are devices, methods, and systems for peripheral and central placement of an implantable midfield-powered neurostimulation device. In an example, the implantable device can be configured for implantation at or near a nerve target in a sacral or genital area, such as for treatment of overactive bladder (OAB). Other targets and treatments can use the same or other implantable device. For example, other targets along the spinal cord can be used, such as for treatment of chronic pain.

Figure 11:
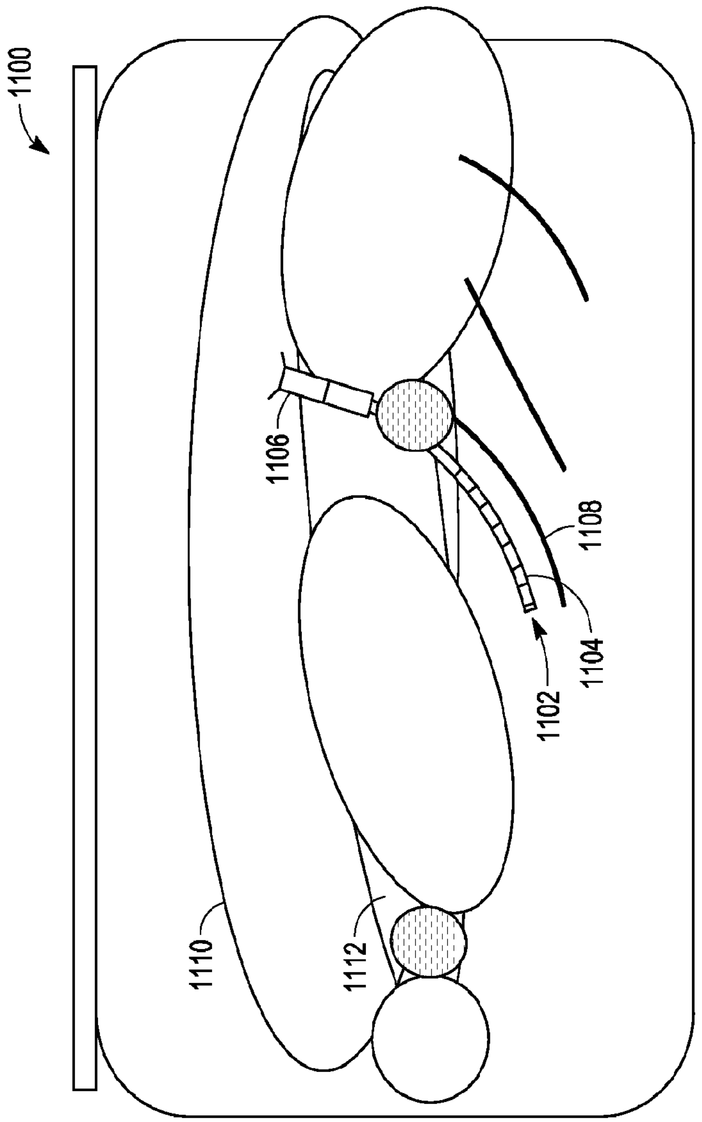
FIG. 11 illustrates generally an example of an implanted electrostimulation device.

FIG. 11 illustrates generally a first example 1100 of an implanted electrostimulation device 1102. In some examples, the electrostimulation device 1102 comprises the implantable device 110, and the electrostimulation device 1102 is configured for wireless communication with the external source 102. The electrostimulation device 1102 can include an electrode portion 1104 and a housing portion 1106. The first example 1100 of FIG. 11 illustrates generally a sacral transforaminal implantation of the device 1102. In the example, the housing portion 1106 is implanted at or in a muscle layer 1110, while the electrode portion 1104 extends through a bony plate 1112 and toward a first neural target 1108.

Figure 12:
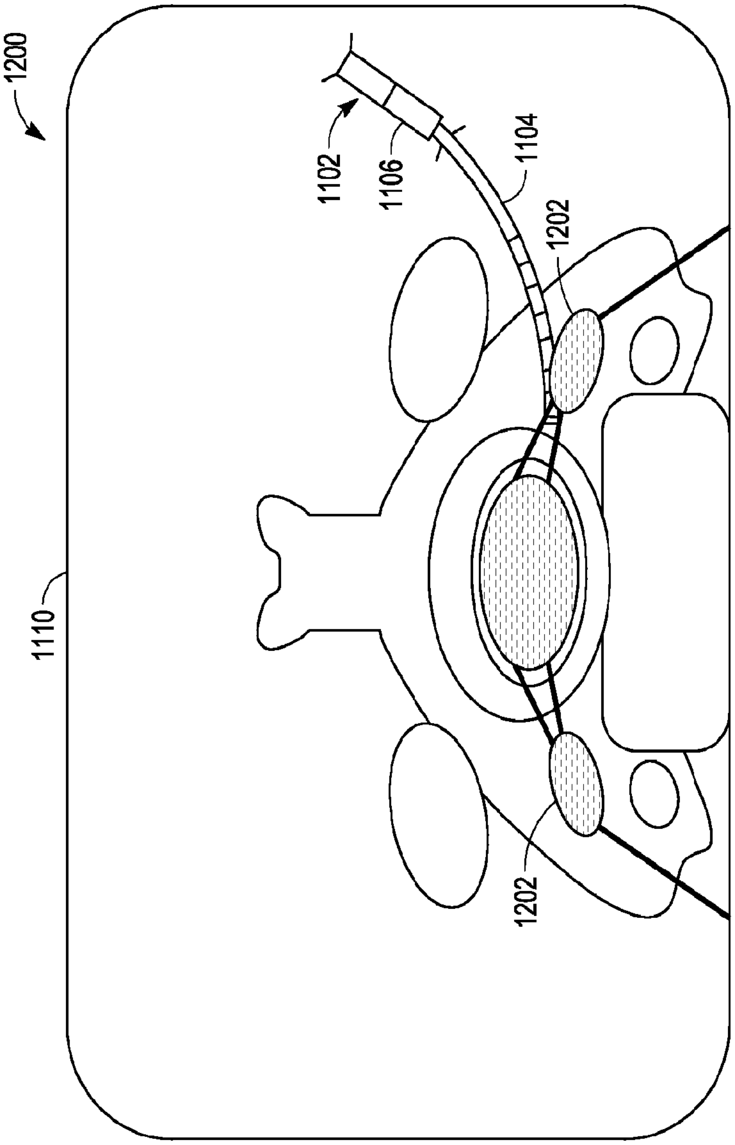
FIG. 12 illustrates generally another example of an implanted device.

FIG. 12 illustrates generally a second example 1200 of an implanted device. In the second example 1200, the device 1102 is implanted using a lateral transforaminal approach. In this example, the housing portion 1106 is implanted at or in a muscle layer 1110, while the electrode portion 1104 extends laterally, e.g., through a neural foramen, toward a second neural target 1202 such as a dorsal root ganglion.

Figure 13:
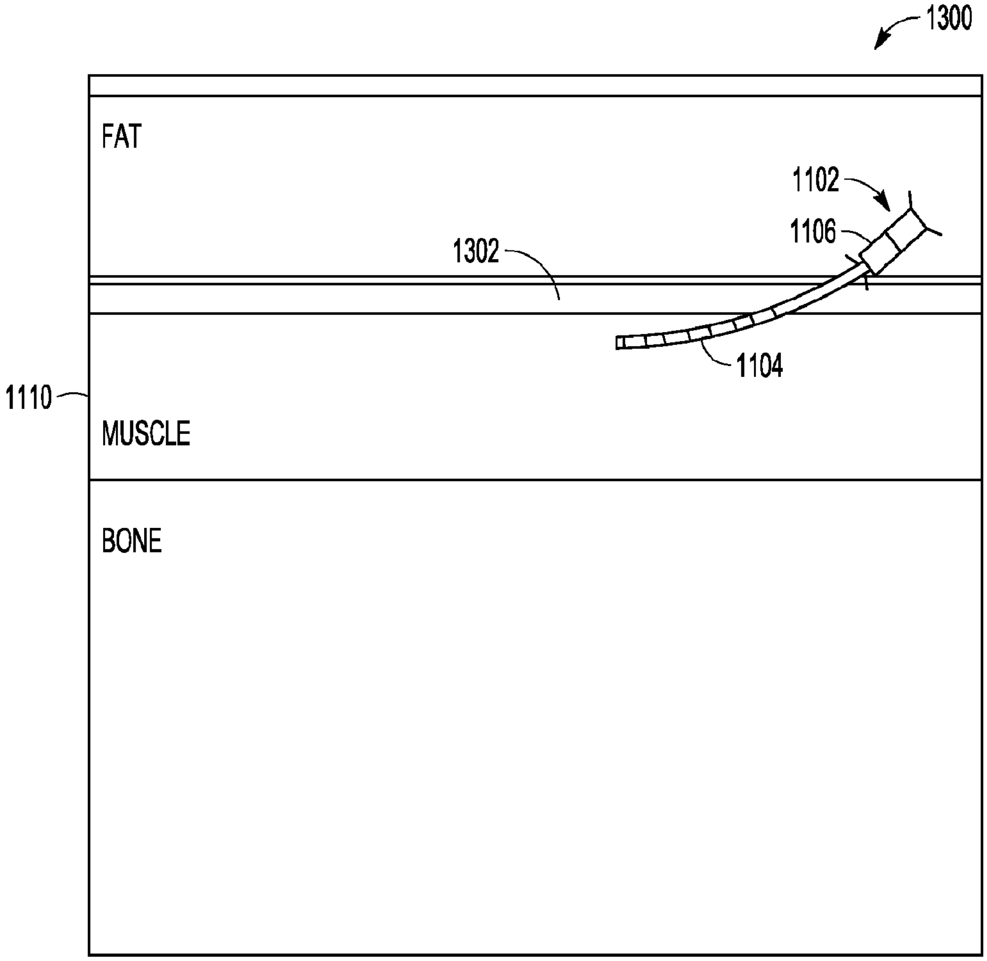
FIG. 13 illustrates generally yet another example of an implanted device.

FIG. 13 illustrates generally a third example 1300 of an implanted device. In the third example 1300, the device 1102 is implanted using a superficial peripheral approach. In this example, the housing portion 1106 can be at least partially installed at or in a fat or fascia layer, while the electrode portion 1104 extends into a muscle region, and toward or through a third neural target 1302.

Figure 14:
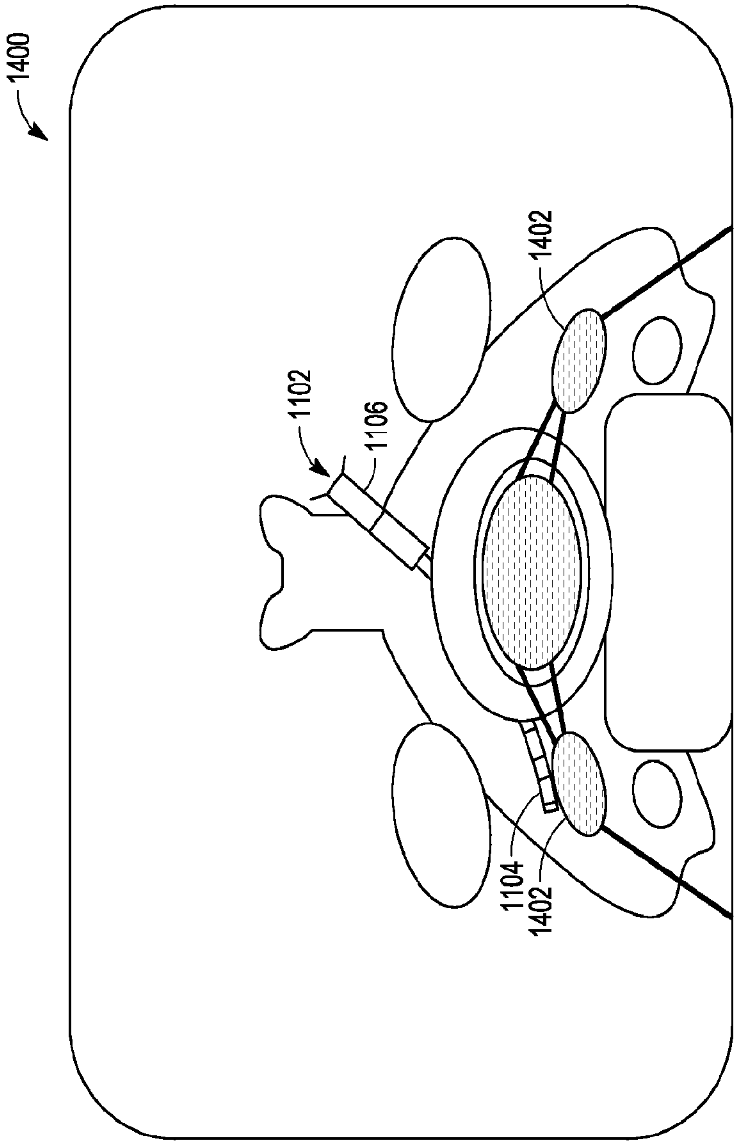
FIG. 14 illustrates generally yet another example of an implanted device.

FIG. 14 illustrates generally a fourth example 1400 of an implanted device. In the fourth example 1400, the device 1102 is implanted using a transepidural approach. In this example, the electrode portion 1104 of the device 1102 can be provided in an epidural space. In an example, the electrode portion 1104 can be provided through the epidural space, via a neural foramen, and can be positioned at or near a fourth neural target 1402 such as a dorsal root ganglion.

Figure 15:
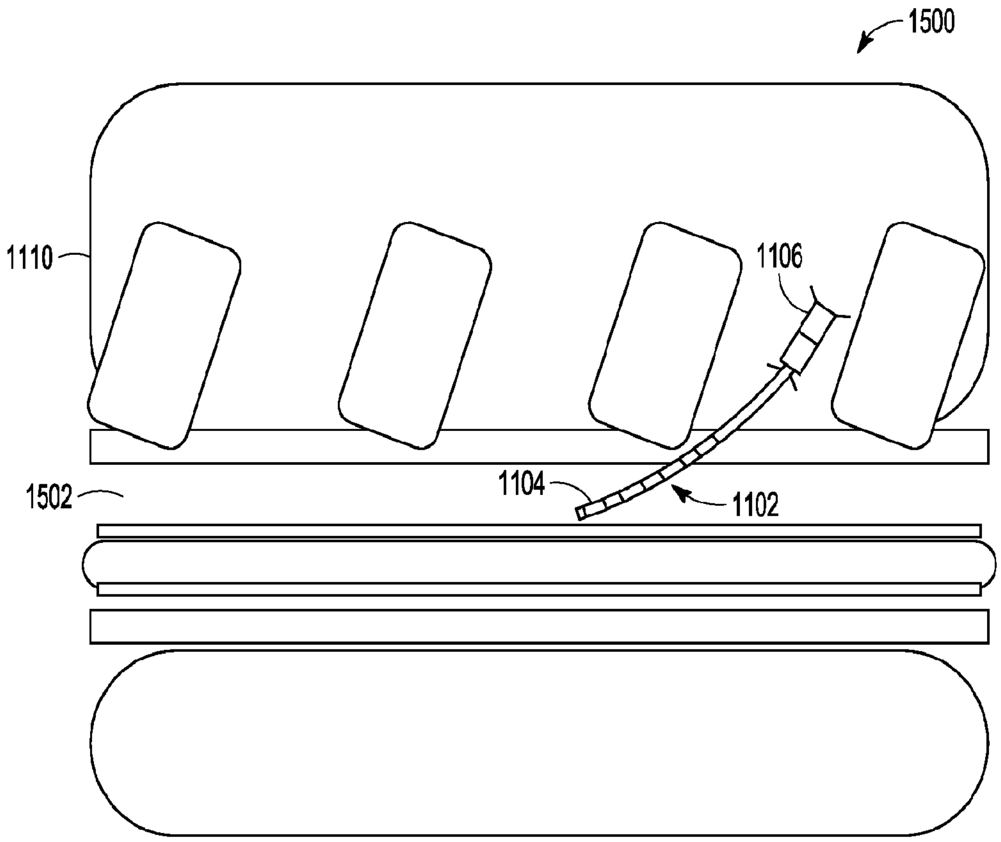
FIG. 15 illustrates generally yet another example of an implanted device.

FIG. 15 illustrates generally a fifth example 1500 of an implanted device. In the fifth example 1500, the device 1102 is implanted at least partially at or in an epidural space 1502. In the fifth example 1500, the housing portion 1106 of the device 1102 can be disposed in a muscular portion of the patient's back. In an example, retention devices such as tines can be provided at or on the housing portion 1106 and can be disposed in the muscle 1110 to help secure or retain the device 1102 in a particular position or orientation. That is, at least a portion of the housing portion 1106 and/or the tines can be provided outside of the epidural space 1502, while the electrode portion 1104 can extend inside of the epidural space 1502.

The present inventor(s) has recognized that a problem with prior devices configured for spinal stimulation can include long tunneling leads that extend through an epidural space. When a patient with such a tunneled lead bends or flexes, the spine curves and bends, which in turn can lead to inconsistent stimulation, such as can result in under-stimulation (i.e., insufficient signal) or over-stimulation (i.e., shocks or other discomfort).

A solution to these and other problems can include or use a unitary implantable device, such as the midfield device discussed herein and in the appendices. The device can be miniaturized such that it can be partly or entirely implanted at the same location or level of the spinal column at which stimulation is to be provided. Accordingly, it can be untethered to other housings or long leads that can otherwise cause shifting or dislocation of electrodes in response to patient movement.

In an example, the solution can include an external midfield transmitter, such as the source 102, configured to provide power and/or data signals to the device 1102 when it is implanted in a patient body. In an example, multiple different devices 1102 can be implanted at different locations along the spinal column, and the same or different midfield transmitter can provide power and/or data signals to the devices 1102. In an example, the external midfield transmitter can be worn by a patient such that it can be positioned against or near the spinal column, such as using a chest strap, belt, girdle, or necklace.

Stable Placement

Generally discussed herein are devices, methods, and systems for retaining a wireless implantable device at an implant site without migration away from a therapy target. The example therapy target discussed is a sacral nerve, but the teachings of this disclosure can be used to help reduce implantable device migration at other targets. The reduction in device migration can be achieved using an implantable device of a specific length or range of lengths. The reduction in device migration can be achieved by locating a portion of the device within an implant tissue window in a patient. The implant window location and size can vary patient to patient as it depends on the anatomical features of the patient. In some examples, the implant window represents a physical depth or location within tissue, and the tissue has a particular density or other characteristic that facilitates implantable device placement and retention. For example, the implant window can include a muscle layer in which tines of an implantable device can be deployed, and from which an electrode array of the device can extend toward a neural target in the same or different tissue layer or tissue type.

Figure 16:
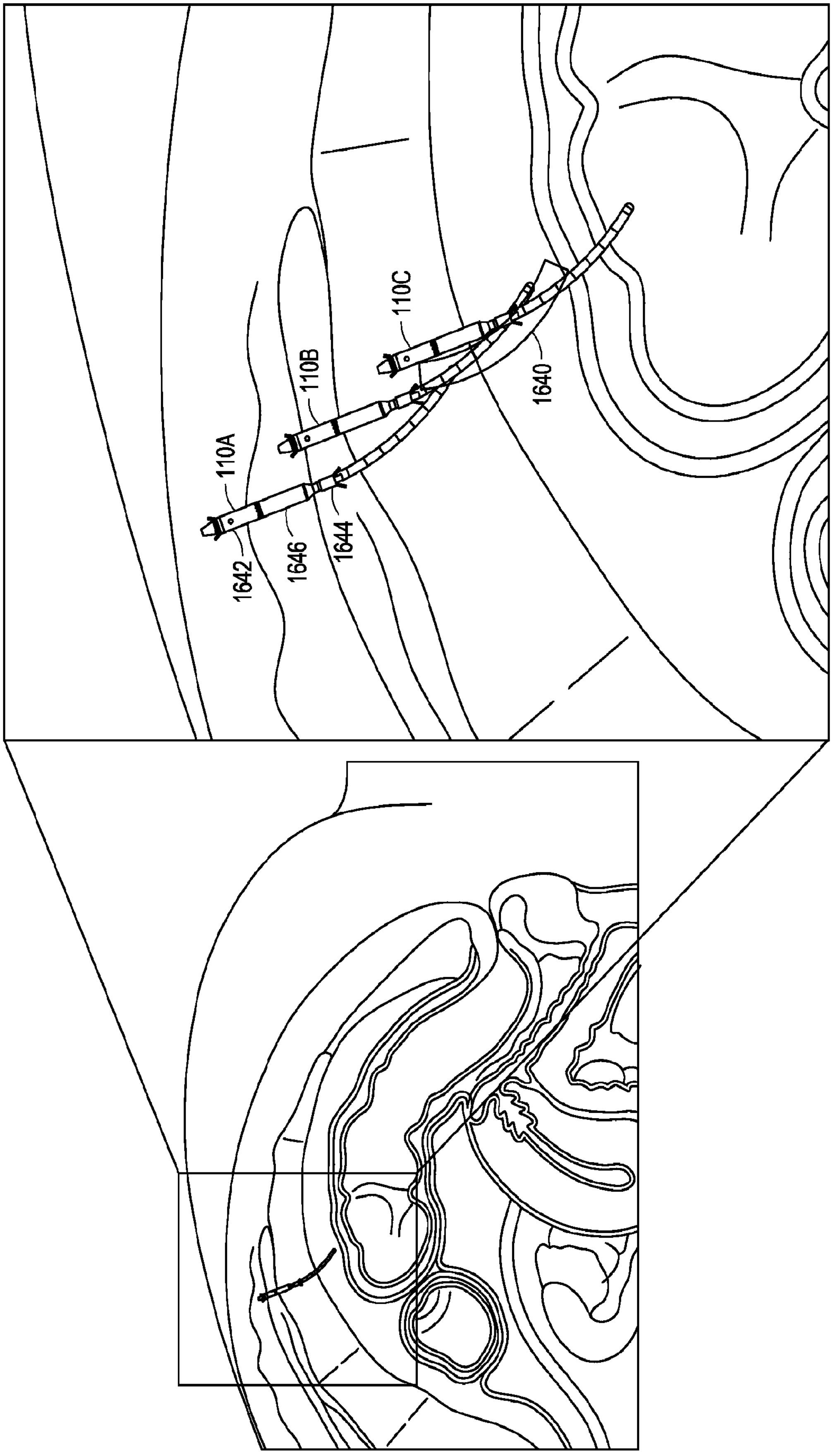
FIG. 16 illustrates, by way of example, a diagram of an implantable device situated at various implant locations.

FIG. 16 illustrates, by way of example, a diagram of the implantable device 110 situated at a variety of implant locations. Each of implantable devices 110A, 110B, 110C represents a different implant location for the implantable device 110. The implantable device 110A is situated such that a most distal electrode (e.g., E0) of the implantable device 110A is situated within a zone of target capture 1640, while other electrodes of the implantable device 110A are outside of the zone. The zone of target capture 1640 can represent an area within which an electrode (or electrodes) can be placed to deliver a particular neurostimulation therapy to reach or activate a particular nerve or neural target. In some examples, the implantable device 110A can migrate out of position or out of the patient body, such as due to normal patient activity. The migration can occur, for example, because tines 1642 of the implantable device 110A are situated in tissue of insufficient density to retain the implantable device 110A in its implant location.

The implantable device 110B is situated such that all of its electrodes are at least partially inside of the zone of target capture 1640. Compared to the implantable device 110A, the implantable device 110B is less likely to migrate out of the patient (and out of the zone of target capture 1640). is the implantable device 110B can be less likely to migrate because the implantable device 110B is situated with tines 1644 in tissue of sufficient density to retain the implantable device 110B. In other words, the tines 1644 of the implantable device 110B can be more likely to catch on to the surrounding tissue and prevent the implantable device 110B from migrating away from the zone of target capture 1640.

The anatomy at or around the sacrum makes it more likely that the device 110A, 110B, 110C will migrate out of the body (towards the skin through which the device 110A, 110B, 110C was implanted). Further, the tissue more distal than the device 110A, 110B, 110C is generally denser and has not been penetrated, unlike the tissue that is more proximal than the device 110A, 110B, 110C.

The implantable device 110C, compared to the devices 110A, 110B, is implanted more distal from an implant site, or deeper within the patient body. The implantable device 110C is situated such that a most proximal electrode (e.g., E3) is situated in the zone of target capture 1640 while one or more other electrodes of the device are outside of the zone. The implantable device 110C can be less likely to migrate or wander away from the implant site, such as toward the skin of the patient, than the implantable devices 110A, 110B, because of its implantation depth and the tissue type in which the device is implanted.

In an example, a neural target includes a sacral nerve, and an implantable device can be situated internal to the patient and proximate the sacrum. A distance between a posterior edge, or surface of the sacrum facing a back of a patient, of the sacrum and a tine 1644, such as situated between electrodes and a circuitry housing 1646, can indicate a likelihood of migration or movement of the implantable device. For example, if the tine 1644 is within about 0.5 centimeters (cm) of the posterior edge of the sacrum, the implantable device 110 will predictably not wander. Further, examples of the implantable device 110, such as situated within about 0.5 cm of the posterior edge of the sacrum, can have an electrode array that affords more flexibility in stimulating the therapy target because more electrodes can be disposed at, in, or near the zone or target capture 1640.

Figure 17:
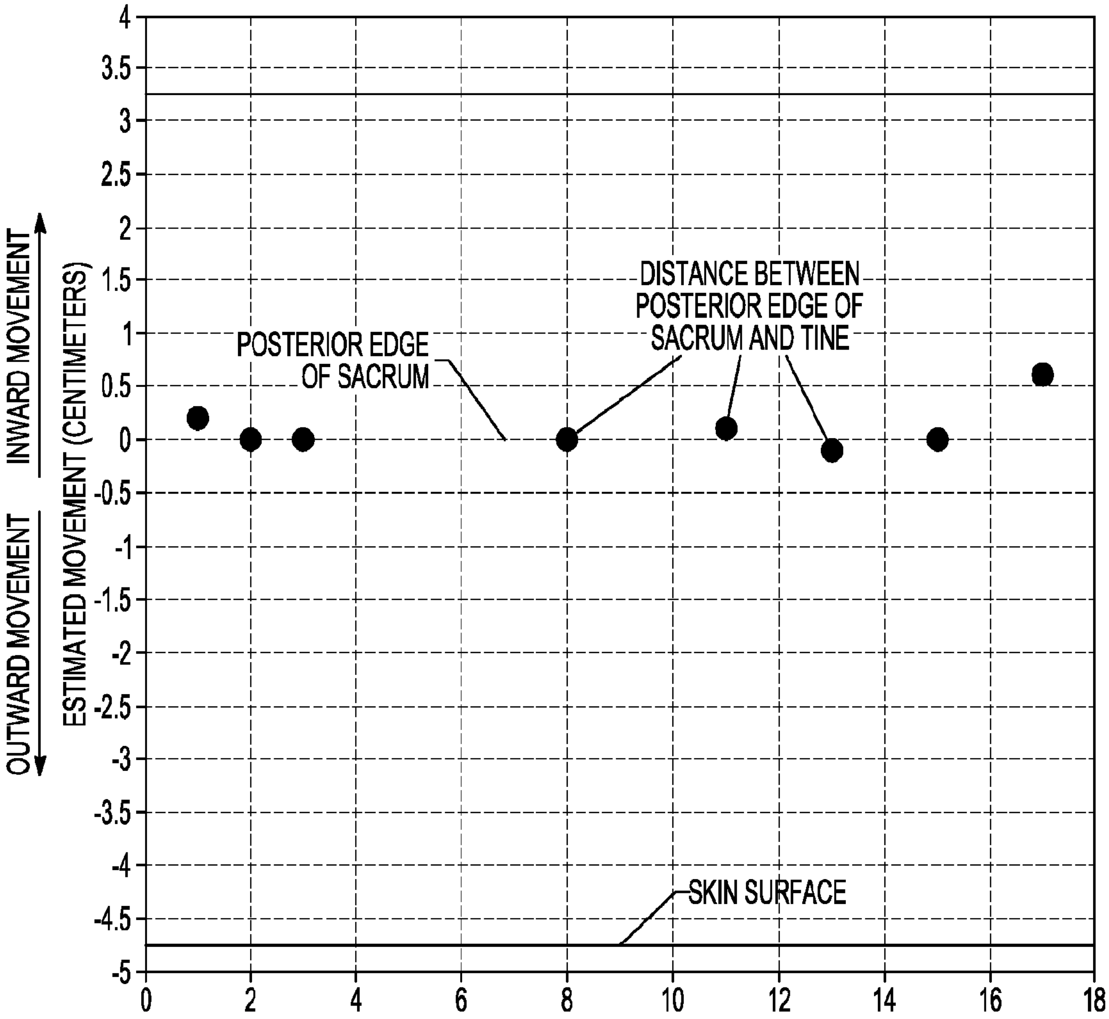
FIG. 17 illustrates, by way of example, a graph of estimated device movement based on implant depth for a number of implantable devices.

FIG. 17 illustrates, by way of example, a graph of estimated movement based on implant depth for a number of implantable devices. Each implantable device is represented by a dot. The dot indicates the distance between the posterior edge of the sacrum and the tine 1644 of the implantable device 110. As can be seen, more inward movement is expected as a distance between a tine and the posterior edge of the sacrum is increased.

Figure 18:
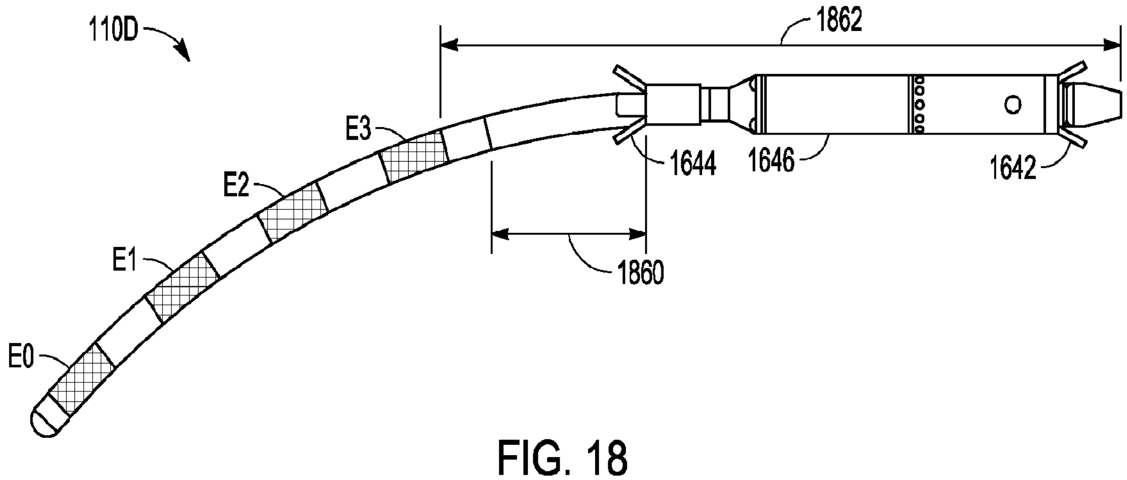
FIGS. 18 and 19 illustrate, by way of example, diagrams of embodiments of implantable devices.
Figure 19:
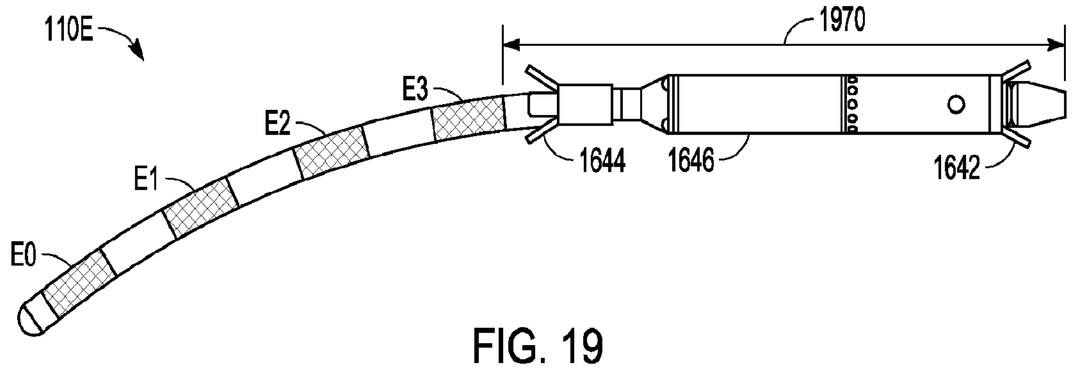

FIGS. 18 and 19 illustrate, by way of example, respective diagrams of embodiments of implantable devices 110D, 110E. The implantable devices 110D, 110E are similar devices, however, the implantable device 110E is shorter in length than the implantable device 110D. The difference in length is indicated by arrows 1862 and 1970. The implantable device 110D includes an elongated portion 1860, while the implantable device 110E omits a similar elongated portion. The implantable devices 110D and 110E can be used to reach different neural targets, such as in the same or different patients. For example, the implantable device 110D can be used to provide therapy deeper into the human body than the implantable device 110E. In another example, the implantable device 110E can be used to provide therapy in a patient that has a thinner sacrum (i.e., has a sacral bone with less distance between its anterior and posterior sides). In some examples, the device 110E can be implanted deeper into the patient to reach same therapy treatment depth as the device 110D. In some examples, the device 110E can be more deeply implanted than the device 110D and can therefore be less likely to migrate out of the patient as it can be situated in more dense tissue.

Figure 20:
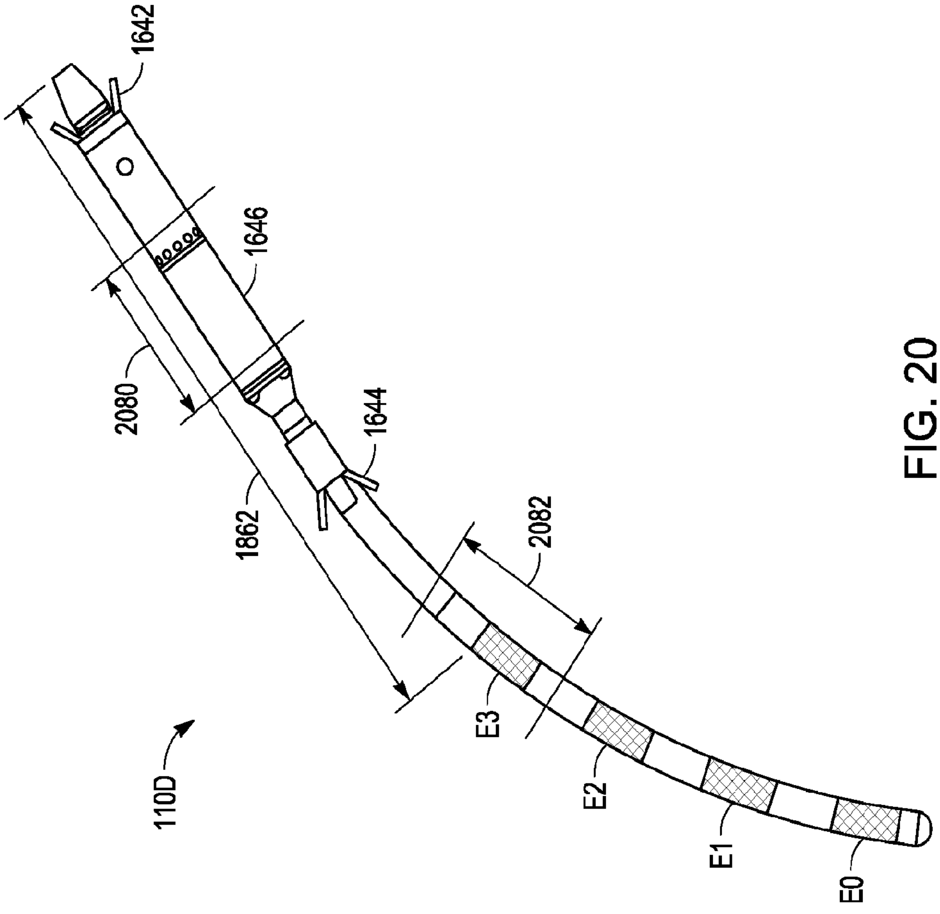
FIG. 20 illustrates, by way of example, a diagram of an implantable device with implant location indicia.

FIG. 20 illustrates, by way of example, a diagram of the implantable device 110D with target implant locations marked. An arrow 2080 indicates a location, or range of locations, at which or within which to situate a posterior edge of a sacrum, such as to reduce a chance that the device 110D wanders after implant. Another arrow 2082 indicates a location, or range of locations, at which or within which to situate an anterior edge of a sacrum, such as to reduce a chance that the device 110D wanders after implant.

Figure 21:
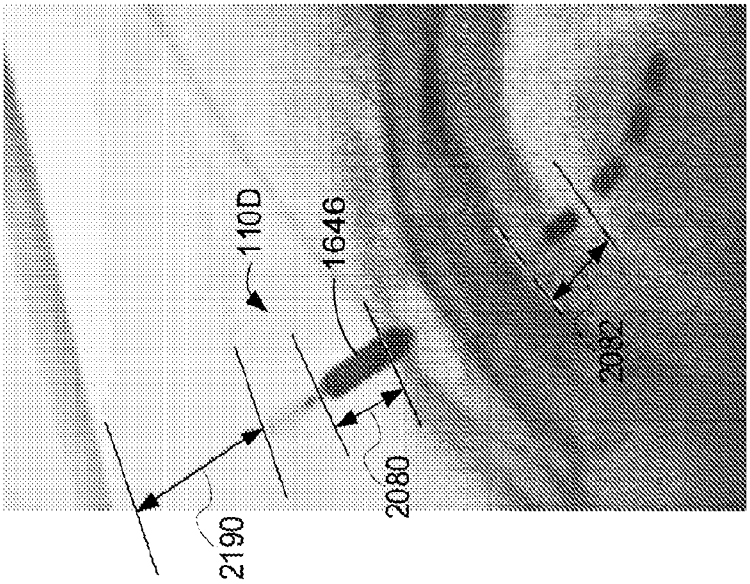
FIG. 21 illustrates, by way of example, a line-art diagram of an implanted device.

FIG. 21 illustrates, by way of example, a line art diagram of the device 110D implanted at a location or position where the device is less likely to wander after implant. The device 110D in FIG. 21 includes a proximal edge of the circuitry housing 1646 situated at about the posterior edge of the sacrum. The device 110D in FIG. 21 further includes the electrode E3 proximate the anterior edge of the sacrum. An arrow 2190 indicates that the device 110D is implanted at a depth of about a centimeter or more from an exterior surface of the skin. The locations of the implant device 110D, the circuitry housing relative to the posterior edge of the sacrum, and the electrode E3 relative to the anterior edge of the sacrum, can be prioritized, such as to help reduce the chances the implant device 110D wanders. The priority can be, in the following order: (1) implant depth>1 cm; (2) posterior edge of sacrum in area indicated by arrow 2080; and (3) anterior edge of sacrum in area indicated by arrow 2082. Situating the posterior edge of the sacrum in the area indicated by arrow 2080 can help guarantee that the tines 1642 are situated in tissue having a tissue type that helps the device resist migration.

Figure 22:
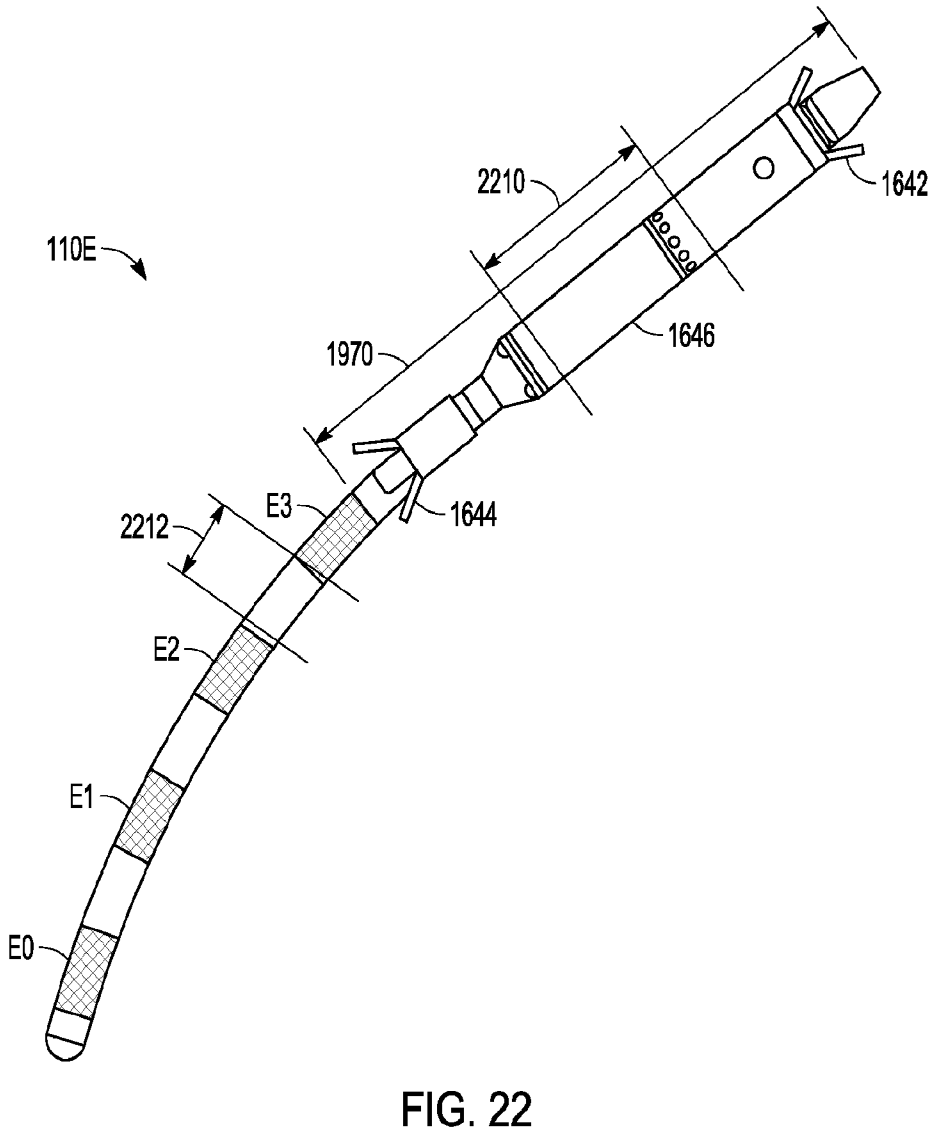
FIG. 22 illustrates, by way of example, a diagram of an implantable device with implant location indicia.

FIG. 22 illustrates, by way of example, a diagram of the implantable device 110E with target implant locations marked. An arrow 2210 indicates a location at which to situate a posterior edge of a sacrum, such as to reduce a likelihood that the device 110E wanders after implant. Another arrow 2212 indicates a location at which to situate an anterior edge of a sacrum, such as to reduce a likelihood that the device 110E wanders after implant. The device 110E, when implanted at a specified location or tissue depth to reduce wandering, includes the circuitry housing 1646 situated at about the posterior edge of the sacrum. The device 110E, when implanted at the specified location or tissue depth, can be positioned such that the anterior edge of the sacrum is between electrodes E2 and E3. In an example, the device 110E, when implanted properly, is implanted a centimeter or more below an exterior surface of the skin. The locations of the depth of the implant device 110E, the circuitry housing 1646 relative to the posterior edge of the sacrum, and the electrodes E2 and E3 relative to the anterior edge of the sacrum, can be prioritized, such as to help reduce a likelihood that the implantable device 110E wanders. The priority can be, in the following order: (1) implant depth>1 cm; (2) posterior edge of sacrum in area indicated by arrow 2210; and (3) anterior edge of sacrum in area indicated by arrow 2212. Situating the posterior edge of the sacrum in the area indicated by arrow 2210 can help guarantee that the tines 1642 are situated in tissue having a tissue type that helps the device resist migration.

Strain Relief

Generally discussed herein are devices, methods, and systems for decreasing strain on a wireless implantable device. In an example, as a patient moves, the device can move, putting strain on one or more portions of the device. The strain can cause the device to bend in an undesirable manner. The bending can make the device sit in an uncomfortable or unintended orientation, thus making the device susceptible to further bending or strain or compromising an efficacy of a therapy provided by the device.

Figure 23:
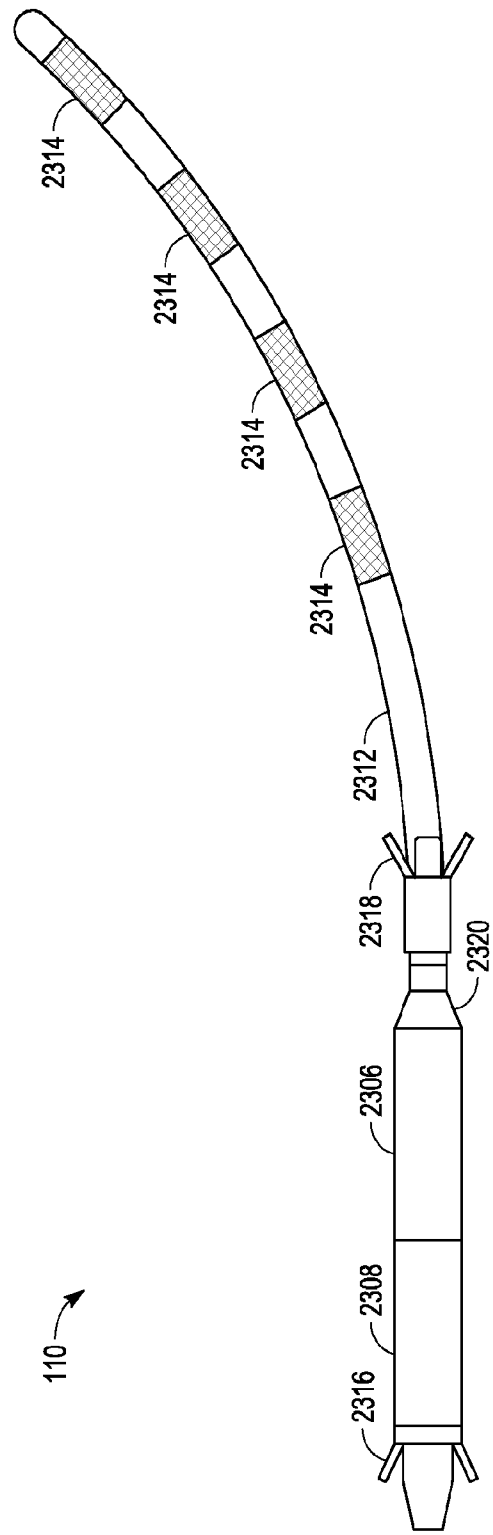
FIG. 23 illustrates, by way of example, a diagram of an embodiment of an implantable device.

FIG. 23 illustrates, by way of example, a diagram of an embodiment of the implantable device 110. The implantable device 110 includes a circuitry housing 2306, an elongated body portion 2312, electrodes 2314, an antenna housing 2308, reverse tines 2316 (e.g., one or more tines extending away from a body of the device in a proximal direction), forward tines 2318 (e.g., one or more tines extending away from a body of the device in a distal direction), and a connector 2320. In the example of FIG. 23, the connector 2320 is frustoconical, however, other shapes or configurations can similarly be used. The circuitry housing 2306 and the elongated body 2312 can be connected to opposing ends of the connector 2320.

The body portion 2312 can include conductive material extending therethrough. The conductive material can electrically connect a conductive feedthrough of the circuitry housing 2306 to a respective electrode 2314.

The body portion 2312 can be formed from or coated with a material having a specified outer-facing surface friction characteristic. For example, the body portion 2312 can comprise a smooth, lower-friction silicone surface or surface portion, or can comprise a rough or textured higher-friction silicone surface or surface portion. Additionally, or alternatively, a rough or textured surface finish can be applied to the outer-face surface, or a portion of the outer-facing surface, of the body portion 2312. A friction-increasing material and/or surface finish can increase friction of the implant relative to the biological tissue in which the implantable device 2310 can be implanted. Increasing friction can help the implantable device retain its implanted position within the tissue. In one or more embodiments, other small-scale features, such as protrusions (e.g., bumps, fins, barbs, rings, braids, or the like) can be added to increase friction in one or more directions. Increasing friction can help improve chronic fixation so that the implantable device is less likely to move (e.g., in an axial direction) while implanted.

The frustoconical connector 2320 includes a proximal side coupled to the circuitry housing 2306. The frustoconical connector 2320 includes a distal side coupled to the body portion 2312 of the implantable device 110. The distal side is opposite the proximal side.

After implant, the implantable device 110 is subject to bending in accord with movement of the patient in which the device 110 resides. The implantable device 110 can tend to bend at the frustoconical connector 2320. The tines 2316, 2318 on each side of the frustoconical connector 2320 can retain a bend in frustoconical connector 2320 or even exacerbate a bend in the frustoconical connector 2320. One could replace a flexible frustoconical connector 2320 with a rigid connector. While this will reduce strain at the connector 2320, such a solution can increase strain between more flexible and more rigid portions of the implantable device 110. When the patient moves, strain can build up between a more rigid circuitry housing portion and a more flexible electrode array portion. This strain can lead to fatigue failure or delamination between the two portions. A better solution is provided in FIGS. 24 and 25.

Referring to FIG. 16 again, each of implantable devices 110A, 110B, 110C represents a different implant location. The implantable device 110A is situated such that only a most distal electrode of the implantable device 110A is situated within a zone of target capture 1640. Under some circumstances, the implantable device 110A can tend to migrate out of the patient, for example because tines 116 of the implantable device 110A are not situated in tissue of sufficient density to retain the implantable device 110A in its implant location.

The implantable device 110B is situated such that all the electrodes 2314 are in the zone of target capture 1640. Compared to the implantable device 110A, the implantable device 110B is less likely to migrate out of the patient (and out of the zone of target capture 1640). This is, at least in part, because the implantable device 110B is situated such that the tines 1642 are in more dense tissue material. This means the tines 1642 are more likely to catch on the surrounding tissue and prevent the implantable device 110B from migrating away from the zone of target capture 1640. Note that the anatomy around the sacrum makes it much more likely that the device 110A, 110B, 110C will migrate out of the body (towards the skin through which the device 110A, 110B, 110C was implanted). The tissue more distal from the tissue surface is generally denser and has not been penetrated, unlike the tissue that is more proximal to the tissue surface.

The implantable device 110C, compared to the devices 110A, 110B, is implanted more distal, or deeper into the tissue. The implantable device 110C is situated such that only a most proximal electrode is situated in the zone of target capture 1640. The implantable device 110C is less likely to wander towards the skin of the patient than the implantable devices 110A, 110B at least because of the characteristics or composition of the tissue in which the implantable device 110C is disposed.

Figure 24:
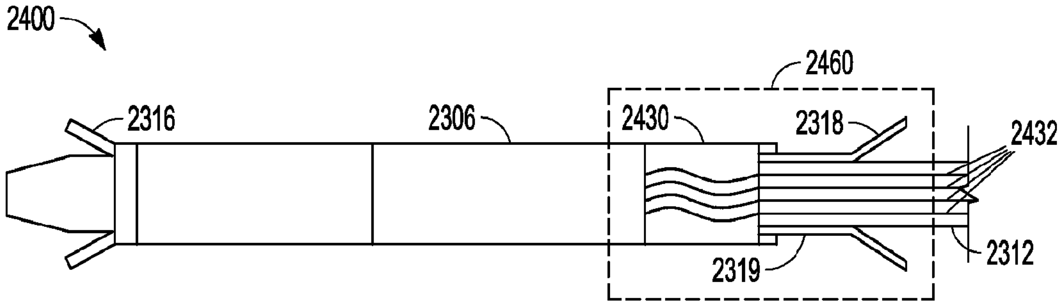
FIG. 24 illustrates, by way of example, a cross-section diagram of a portion of an implantable device that includes a strain relief.

FIG. 24 illustrates, by way of example, a cross-section diagram of an embodiment of an implantable device 2400 that includes one or more components configured to mitigate strain or provide strain relief. The strain relief can be provided in part by reducing an amount of strain in the implantable device 110 by changing a material at a location at which the implantable device 110 is configured to bend. The strain relief can be at least in part provided by a particular shape or configuration of a connector 2430 between the circuitry housing 2306 and the body portion 2312. In an example, the connector 2430 can be generally cylindrical, or otherwise configured to wrap around or enclose at least a portion of the circuitry housing 2306 or another portion of the implantable device. In an example, the connector 2430 can include or comprise a band or collar, such as can extend around some or all of the implantable device. The connector 2430 can include a material, such as polyether ether ketone (PEEK), polyetherimide (PEI), or the like.

Using the connector 2430, the implantable device 110 is designed to bend at the body 2319 of the tine assembly 2318. The body 2319 can made of a material with a flexibility that is more rigid than the body 2312 of the electrode 2314 array and more flexible than the connector 2320. This allows the implantable device 2400 to be affected less by movement of the patient as compared to the implantable device 110.

Figure 25:
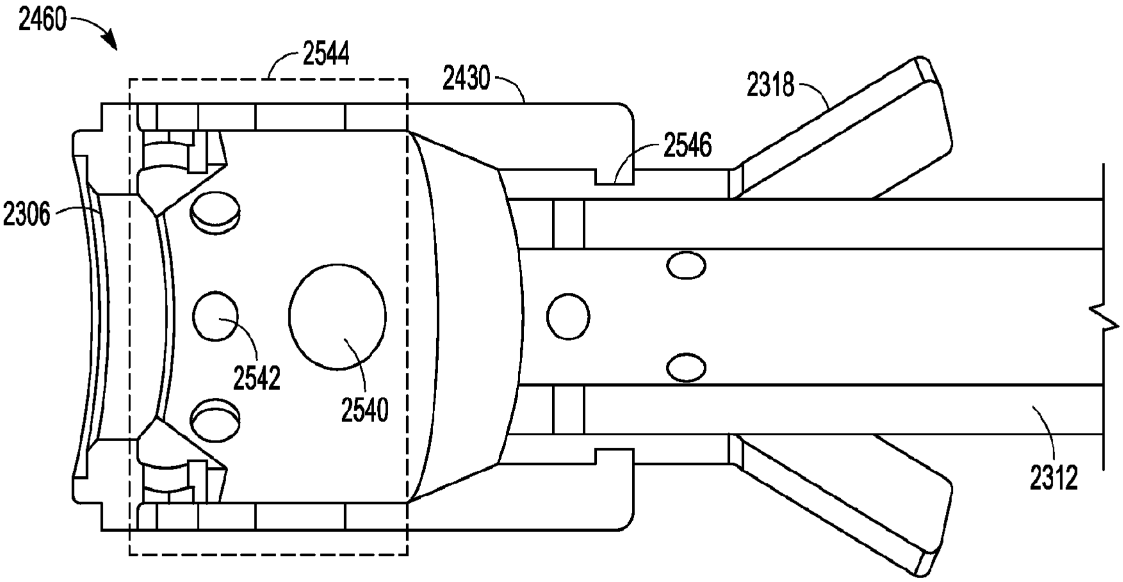
FIG. 25 illustrates, by way of example, a cross-section diagram of a fillable portion of an implantable device.

FIG. 25 illustrates, by way of example, an exploded view diagram of a portion 2460 of the implantable device 2400. A connection 2546, such as provided between the connector 2430 and the tine assembly 2318, includes a tab or protrusion on the connector 2430 coupled with a detent on the tine assembly 2318. The connection 2546 can retain the tine assembly 2318 in place.

A portion of the connector 2430 between the circuitry housing 2306 and the tine assembly 2318 or body portion 2312 can bend to allow for patient movement. The connector 2430 can be difficult to break and can tend to remain unbent (i.e., remain in the position shown in FIG. 25).

The connector 2430 can include a hole 2540 through which a polymer or other dielectric filler material can be injected. The dielectric filler material can provide additional electrical separation or isolation between the conductive wires 2432. The dielectric filler material can increase a rigidity of the connector 2430, such as to reduce bending of the connector, while still allowing for the patient movement.

The connector 2430 can include a sight hole 2542. The conductive wires 2432 can be connected, by a laser weld or the like, to the circuitry housing 2306. The welding, or visual verification of the connections formed by welding, can be provided using the sight hole 2542.

The connector 2430 can include a lumen, or otherwise be hollow, such as to allow the conductive wires 2432 to travel therethrough. The lumen can be filled, at least partially, with dielectric filler. The connector 2430 can include a proximal portion 2544 that includes a first wall thickness. A portion of the connector 2430 more distal than the proximal portion 2544 can include a wall that includes a second wall thickness. The second wall thickness can taper to be thinner closer to the proximal portion 2544. The second wall thickness can be thicker than the first wall thickness. The second wall thickness can taper from the first wall thickness to a third thickness. The third thickness can be generally uniform beginning at about the tine assembly 2318 or the body portion 2312 and until about the connection 2546.

Figure 26:
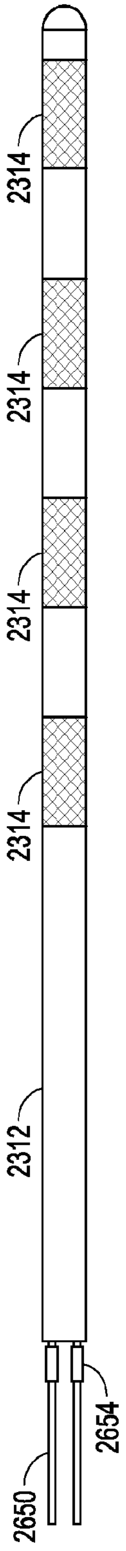
FIGS. 26, 27, 28, 29, 30, 31, 32, and 33 illustrate, by way of example, respective diagrams of respective operations for assembling an implantable device with improved strain relief.

FIGS. 26, 27, 28, 29, 30, 31, 32, and 33 illustrate, by way of example, respective diagrams of respective operations of a technique to assemble an implantable device with strain relief. FIG. 26 illustrates an electrode assembly that includes proximal conductive extensions 2650, conductive collars 2654 electrically connected to the conductive extensions 2650, an electrode assembly body 2312, and electrodes 2314 situated on, or at least partially in, the electrode assembly body 2312. Respective electrodes 2314 are electrically connected to respective conductive extensions 2650. For ease of illustration, only two of the conductive extensions 2650, corresponding to two of the electrodes, are shown.

Figure 27:
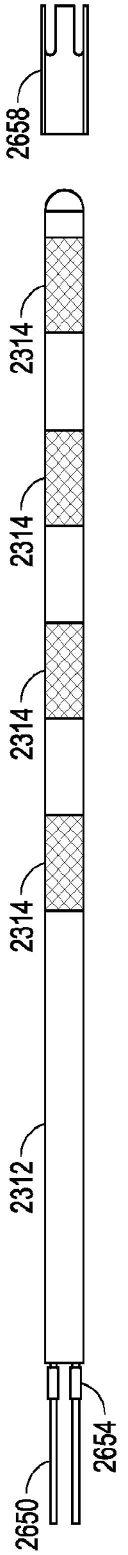
Figure 28:
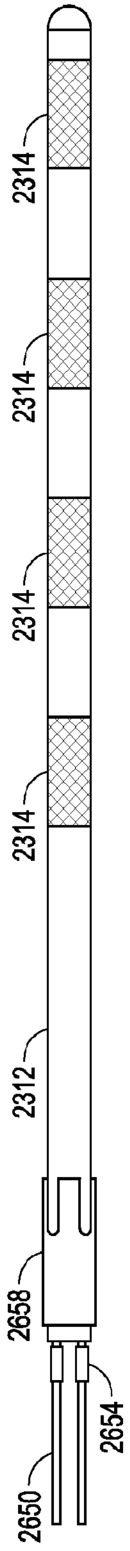

In FIG. 27, a molded fixation component 2658 is about to be situated over the electrode body 2312. FIG. 28 illustrates the fixation component 2658 situated on the electrode body 2312 at a location more proximal than the electrodes 2314. The fixation component 2658 can be heat bonded or otherwise mechanically coupled with the electrode body 2652.

Figure 29:
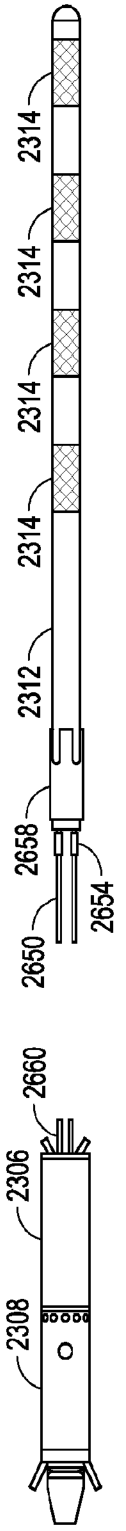

FIG. 29 illustrates a circuitry assembly including the circuitry housing 2306 and the antenna housing 2308 situated proximate the electrode assembly of FIG. 28. The circuitry housing 2306 houses electrical components of the implantable device and protects the electrical components from a surrounding environment. The antenna housing 2308 houses one or more antennas (e.g., one or more of the antennas 108 of the implantable device 110) and protects the antenna(s) therein from the surrounding environment. The circuitry housing 2306 can include conductive extensions 2660 extending from a distal end thereof.

Figures 30, 31, 32, 33:
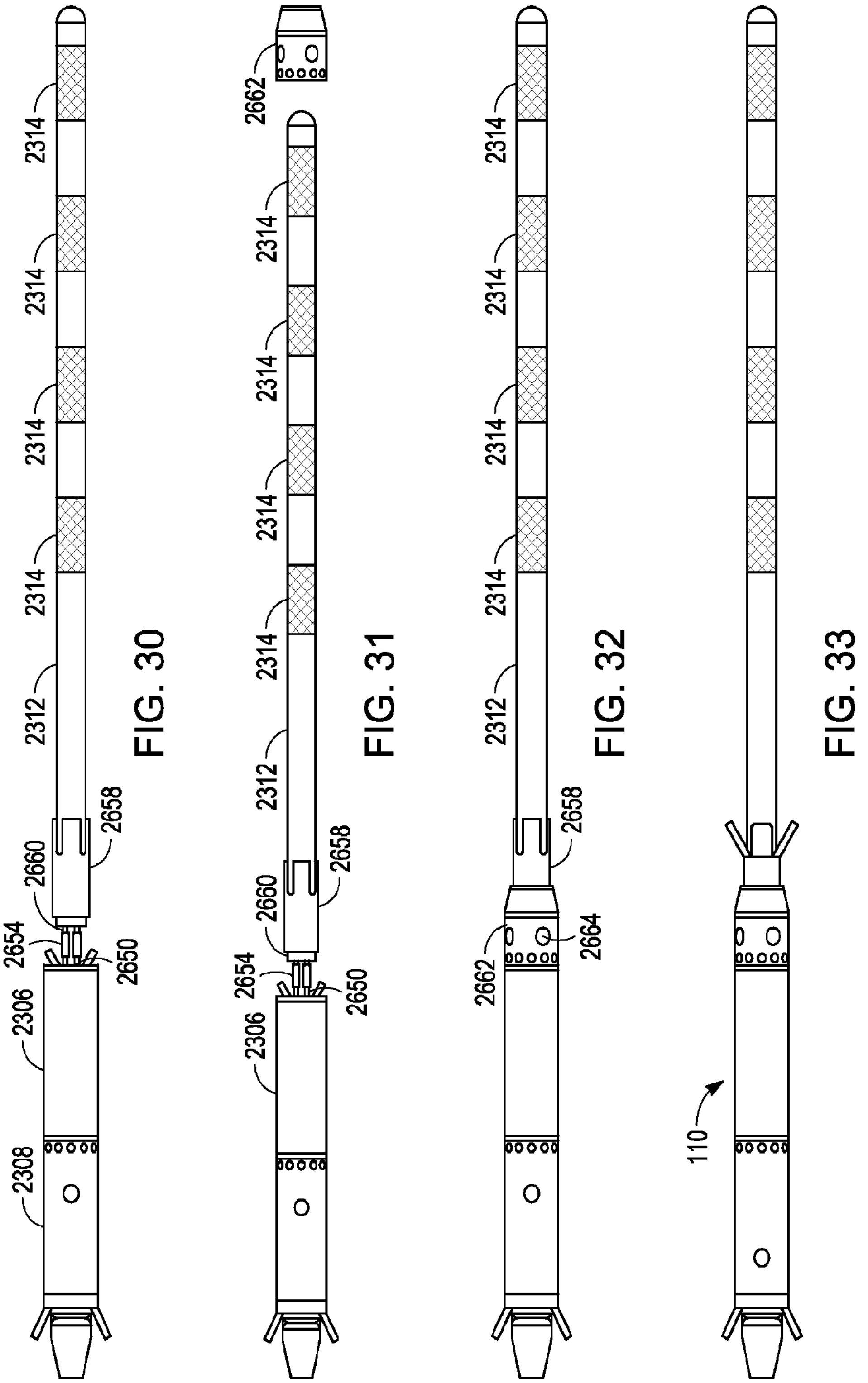

FIG. 30 illustrates the electrode assembly and the circuitry assembly of FIG. 29 electrically and mechanically coupled. The conductive extensions 2660 can be situated (at least partially) in the conductive collar 2654. Respective conductive extensions 2660 can then be welded, soldered, or otherwise electrically and mechanically connected to respective conductive extensions 2650.

In FIG. 31, a strain relief cap 2662 is being situated over the electrode body 2312. The strain relief cap 2662 can be mechanically coupled to a distal end of the circuitry housing 2306. The mechanical coupling can include a groove mating with a wheel, an indent mating with a protrusion, or other mechanical coupling. The strain relief cap 2662 can cover a location at which the conductive extensions 2650 and 2660 are electrically and mechanically connected. The strain relief cap 2662 can cover the conductive collar 2654. FIG. 32 illustrates the strain relief cap 2662 mechanically coupled to the distal end of the circuitry housing 2306.

Epoxy or other polymer can be injected through an eye hole 2664 in the strain relief cap 2662. The epoxy can be compressible, moldable, or otherwise deformable to form around the conductive extensions 2650 and 2660 and provide mechanical stability to the conductive extensions 2650 and 2660. FIG. 33 illustrates a fully formed embodiment of the implantable device 110 with strain relief. FIG. 33 illustrates a fully formed embodiment of the implantable device with strain relief and a tine assembly.

Garment

Figure 34:
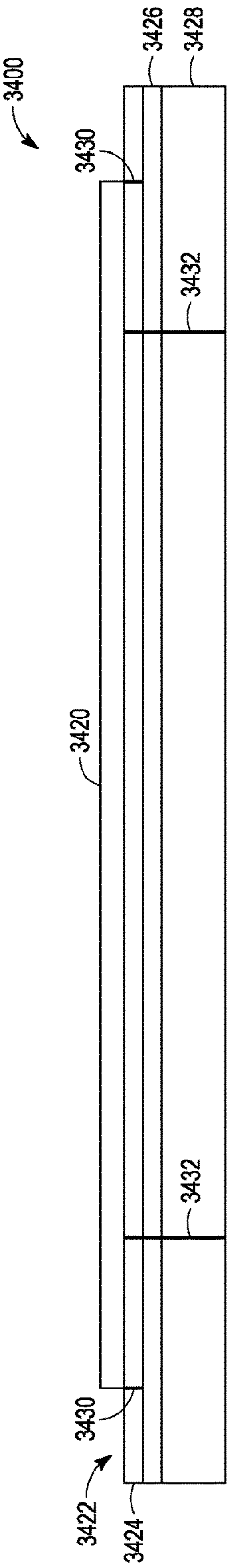
FIG. 34 illustrates, by way of example, a perspective view diagram of an embodiment of a system that includes components of an external source device.

FIG. 34 illustrates, by way of example, a perspective view diagram of an embodiment of a system 3400 that includes components of the source 102, such as the control hardware and the electromagnetic transmission element, on a single board 3422 or substrate. The system 3400 as illustrated includes the control hardware and the transmission element on a top layer of the substrate (not illustrated). The transmission element is separated from the control hardware by a faraday cage 3420 or other element that excludes or inhibits ingress of electrostatic or electromagnetic energy, such as to shield the control hardware from electromagnetic radiation of the transmission element and vice versa.

The faraday cage 3420 can be a part of the electromagnetic transmission element that radiates. The control components are fully integrated within a conductive surface of the transmission element using the faraday cage 3420. In such embodiments, the faraday cage 3420 is acting both as a shield (for the control components) and as a radiating element of the transmission element. Due to the skin depth of the material used for the faraday cage 3420, the electromagnetic currents at the outer surface of the faraday cage that induce radiation do not penetrate more than several microns at gigahertz frequencies. Thus, the internal components can advantageously be shielded from the electromagnetic fields induced by the faraday cage 3420 radiating as part of the transmission element, in accordance with one or more embodiments.

In one or more embodiments, the board 3422 can include multiple layers, such as a first layer 3424, a second layer 3426, and a third layer 3428. The third layer 3428 can be thicker than the first layer 3424 and the second layer 3426. In one or more embodiments, the board 3422 can be made of an FR4 substrate (e.g., a glass-reinforced epoxy laminate comprising a composite material composed of woven fiberglass cloth with an epoxy resin binder that is flame resistant), a silicon substrate, Ajinomoto build-up film (ABF), a dielectric, or other material. The control hardware can be situated on a top surface of the first layer 3424 along with routing (e.g., traces) between components of the control hardware. The components of the control hardware (e.g., high power components) may have thermally conductive material applied to conduct heat to the faraday cage 3420.

A ground plane can be situated on the second layer 3426. The faraday cage 3420 can be shorted to the ground plane by one or more vias 3430. One or more vias 3432 can provide a signal to a port of a slot 3434 or another resonating element on the third layer 3428. The signal to the port can be from one of the power amplifiers. The faraday cage 3420 and the ground plane can be configured with corresponding slots (a slot pattern).

In one or more embodiments, the control hardware components are placed on a surface layer of the board 3422 with a majority of the routing provided on the same surface layer. In the embodiment of FIG. 34, the control hardware and most of the routing are on a top surface of the first layer 3424 (e.g., the surface on which the faraday cage 3420 is mounted).

In one or more embodiments, the slot mid-field pattern (e.g., ground plane) can be printed on, or at least partially in, the second layer 3426 (e.g., the layer immediately below the first layer 3424). In one or more embodiments, the second layer 3426 can also serve as a ground plane. One or more vias 3430 can be included that connect the first layer 3424 with the second layer 3426, such as to short the faraday cage 3420 at the top layer to ground. In one or more embodiments, the vias 3430 can be at or near the edges of the mid-field pattern and/or the edges of the slots which form the midfield element. Layers between the ground plane and excitation ports along a bottom surface of the third layer 3428 may be used for limited traces. In some embodiments, microstrip excitation slots or feeds are positioned along or adjacent a bottom surface of the third layer 3428.

Figure 35A:
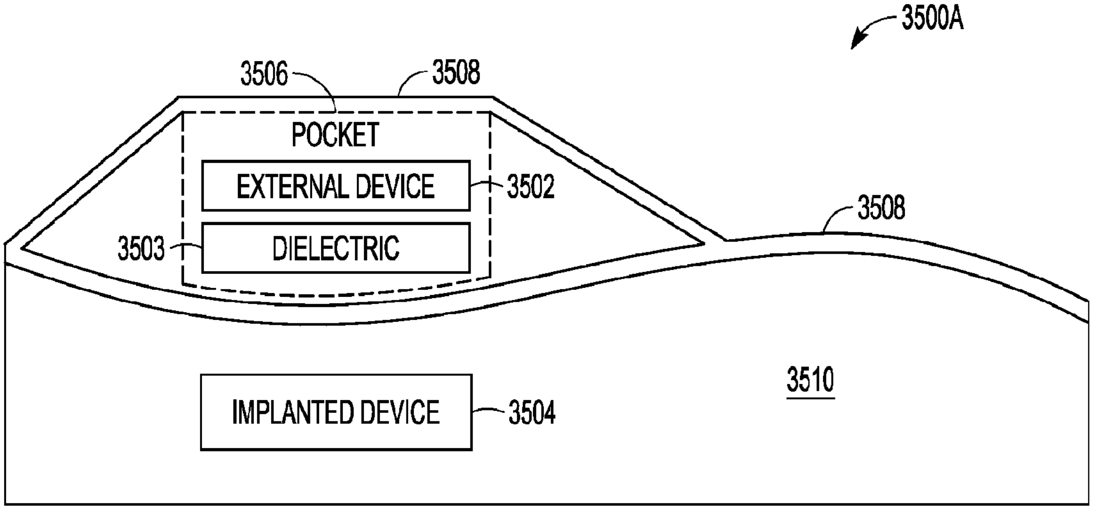
FIGS. 35A and 35B illustrates, by way of example, respective embodiments of a system for communication of one or more signals between an implanted device and an external device.

FIG. 35A illustrates, by way of example, an embodiment of a system 3500A for communication of one or more signals between an implanted device 3504 and an external device 3502. The implanted device 3504 can be similar to or the same as any of the implantable devices discussed herein, such as the implantable device 110, or another implantable device. The external device 3502 can be similar to or the same as any of the external devices discussed herein, such as the source 102, the antenna 300, or the like. The external device 3502 can be situated in and/or affixed at a position within a pocket 3506. The implanted device 3504 can be implanted under the surface a user's skin, such as to be internal to a body 3510 of a user. The external device 3502 can transfer power and/or data to the implanted device 3504. In one or more embodiments, the external device 3502 is positioned in a sleeve or other affixation or retention feature of a wearable garment. In an example, the system 3500A includes a dielectric member 3503 provided between the external device 3502 and the user's body 3510 or tissue surface.

The pocket 3506 can be internal to, or coupled to, a wearable element 3508, such as an undergarment, pants, shirt, panty hose, shorts, bodysuit, wearable elastic band, and so forth. In the example of FIG. 35A, the pocket 3506 is drawn using dashed lines to indicate the boundaries of the pocket 3506. In various embodiments, boundaries of the pocket 3506 or other receptacle can be fixed or adjustable and can be configured to accommodate one or several different types of external devices. The boundaries or walls of the pocket 3506 can be rigid or compliant (e.g., elastic), and can be configured to receive and retain the external device 3502 in a particular location relative to other portions or features of the wearable element 3508. For example, when the wearable element 3508 includes an underwear or underpants garment, the pocket 3506 can be provided in a fixed location relative to an elastic waistband or to leg holes of the garment. A position of the pocket 3506 relative to one or more of the other features of the wearable element 3508 can depend on, or can be related to, an overall size of the wearable element 3508, as further discussed herein.

In an example, the dielectric member 3503 is configured to facilitate or enhance wireless communication between the external device 3502 and the implanted device 3504. The dielectric member 3503 can include a material having a dielectric or relative permittivity characteristic that is the same or similar to that of air (e.g., having a K value of approximately 1). In an example, relative permittivity of the dielectric member 3503 is the same or similar to that of air at one or more particular frequencies or frequency bands of interest. For example, a frequency band of interest can include a band from about 300 MHz to about 5 GHz.

In an example, the dielectric member 3503 includes or comprises one or more of a polychloroprene rubber (e.g., neoprene), a urethane (e.g., PORON MSRS), a foam, or other natural or composite material, generally provided in a sheet, rectangular cuboid, cylindrical, or other shape having non-negligible width, height, and depth or length dimensions. Generally, the dielectric member 3503 has low thermal conductivity and is resistant to mild acids and bases.

The dielectric member 3503 can be elastic or compressible to enhance user comfort when a garment comprising the dielectric member 3503 is worn. A dielectric characteristic (e.g., relative permittivity value) can be substantially unchanged when the member is in compressed and uncompressed (e.g., relaxed) states. In an example, the dielectric member 3503 can receive a first force or pressure over a first area on a first side of the member and distribute the force or pressure over a greater second area on at least a second side of the member, such as to enhance user comfort.

In an example, the dielectric member 3503 is configured to provide an effect similar to an airgap between the external device 3502 and the tissue, or tissue interface, of the user. The dielectric member 3503 can have a relative permittivity characteristic that is less than a relative permittivity of a substrate of the source, is less than a relative permittivity of a housing that encloses the source and is less than a relative permittivity of tissue at the tissue interface (e.g., tissue in which the implanted device 3504 is implanted). The dielectric member 3503 so configured provides a tunneling effect for energy provided by the external device 3502 and avoids a strong coupling between the tissue itself and the external device 3502. In other words, instead of providing a matching layer that enhances coupling between the external device 3502 and the tissue in which the implanted device 1404 is implanted, the dielectric member 3503 is configured to provide a relative permittivity mismatch at the tissue interface, which in turn facilitates energy tunneling from the midfield external device 3502 to the implanted device 3504.

Figure 35B:
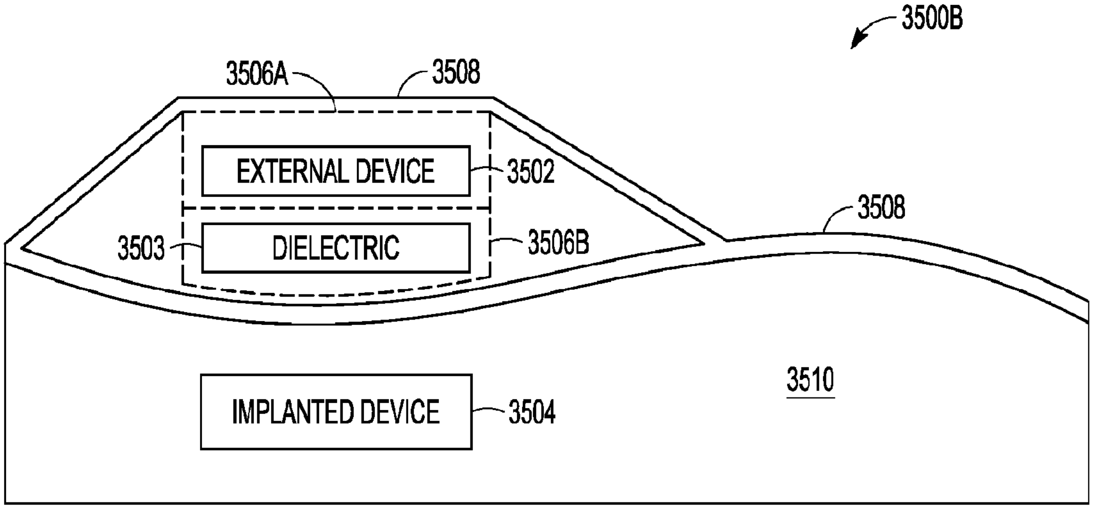

In the example of FIG. 35A, the dielectric member 3503 and the external device 3502 are co-located in a common cavity of the pocket 3506. FIG. 35B illustrates, by way of example, an embodiment of a system 3500B for communication of one or more signals between the implanted device 3504 and the external device 3502. The system 3500B includes first and second receptacles 3506A and 3506B. The first and second receptacles 3506A and 3506B can be affixed or attached to a common wearable element 3508. In the example of FIG. 35B, the first receptacle 3506A is configured to receive the external device 3502 and the second receptacle 3506B is configured to receive the dielectric member 3503. A sidewall (e.g., comprising one or more of the same materials as used in the constructions of the wearable element 3508, or a different material) can be provided between the first and second receptacles 3506A and 3506B, for example, to facilitate better or more accurate placement of each of the external device 3502 and the dielectric member 3503 relative to the wearable element 3508 and therefore to the body 3510. In other words, the first and second receptacles 3506A and 3506B can share a common sidewall. The size, shape, and volume of each of the first and second receptacles 3506A and 3506B can be the same or different; generally, dimensions or elasticity characteristics of the one or more receptacles can be selected or configured according to the device and/or dielectric member that is intended for use therein.

In an example, one or more materials that comprise the wearable element 3508 and the pocket (e.g., the pocket 3506, and/or the first or second receptacles 3506A or 3506B) can have a dielectric characteristic or relative permittivity that is the same or different than a permittivity characteristic of the dielectric member 3503. In an example, different portions of the wearable element 3508 can comprise different materials having respective different permittivity characteristics. For example, a portion of the wearable element 3508 configured for placement between the dielectric member 3503 and the body 3510 of the user can include a material having a relative permittivity characteristic that is substantially the same as the permittivity of the dielectric member 3503.

Various other benefits can be realized when the external device 3502 is used together with the dielectric member 3503. For example, the dielectric member 3503 can provide thermal insulation between the user's body 3510 and the external device 3502. Thus, heat generated by the external device 3502 can be inhibited from reaching the body 3510 of the user. In some examples, a garment configured to hold the external device 3502 and/or the dielectric member 503 can be configured to sink heat away from the external device 3502 to additionally shunt heat away from the body 3510 of the user.

The dielectric member 3503 can have a height characteristic (e.g., a thickness) that is configured to provide a specified minimum separation distance or standoff between the external device 3502 and a tissue interface of the user's body 3510. In an example, the minimum separation distance is about 2 mm. The specified minimum separation distance can be selected to reduce loading on a transmission antenna of the external device 3502, and thereby enhance or improve the longevity of the external device 3502 per charge. In other words, the separation distance between the external device 3502 and a tissue interface can be tuned or selected to avoid exceeding a defined maximum loading condition of a transmission antenna of the external device 3502. Loading of the transmission antenna can be a function of, among other things, operating frequency, which can be separately or additionally tuned by circuitry on the external device 3502.

In an example, the specified minimum separation distance can be selected to reduce a rate at which electromagnetic energy is absorbed by tissue, that is, by the body 3510 of the user, such as at or near the tissue interface. In other words, the dielectric member 3503 can help reduce a specific absorption rate at the body 3510 of the user from energy originating from the external device 3502. In some embodiments, a specific absorption rate can be sufficiently low that no additional standoff is needed or desired.

Figure 36:
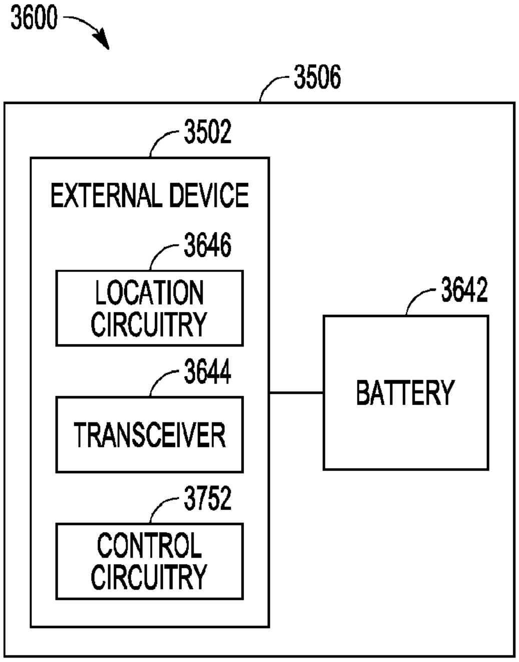
FIG. 36 illustrates, by way of example, a block diagram of an embodiment of a system that includes multiple discrete external components.

FIG. 36 illustrates, by way of example, a block diagram of an embodiment of a system 3600 that includes multiple discrete external components (e.g., the external device 3502 and a battery 3642). The battery 3642 is external to the external device 3502 and situated near the external device 3502 in the pocket 3506 (or in the sleeve). In one or more embodiments, the battery 3642 can be situated outside the pocket 3506 or sleeve. In one or more embodiments, the battery 3642 includes one or more of a lithium polymer battery, a generally flat, flexible battery, a rechargeable battery (e.g., a wired battery charging capability or a wireless battery charging capability, such as through an inductive power link). The battery 3642 can provide electric power to the electric and electronic components (e.g., the internal circuitry, such as can include a transceiver 3644 and other components, such as circuitry of the external device, the source 102, or the like).

The location circuitry 3646 includes electric or electronic components (e.g., resistors, transistors, inductors, capacitors, diodes, sensors, logic gates, oscillators, multiplexers, antennas, radios, ADCs, DACs, speakers, haptic actuators, or the like) that aid the user in situating the external device 3502 in a proper or suitable location for data and/or power communication with an implanted device. The location circuitry 3646 can include components to determine a received signal strength (RSS) of a signal from the implanted device 3504. The RSS can be used to create a tone, such as using a loudspeaker or the location circuitry 3646. The tone created can be modulated based on the value of the RSS to indicate to a user a relative value of the RSS. The user can then situate the external device 3502 at a location corresponding to a relatively high RSS (a tone that indicates a relatively high RSS). In one or more embodiments, the location circuitry 3646 includes a button that a user can press to initiate a placement operation and detection process. The location circuitry 3646 can provide the user with an indication (e.g., a tone or mechanical feedback, such as a vibration or pulse). The location circuitry 3646 can beep in response to the RSS dropping below a threshold value, such as to indicate to the user that the external device is not properly located. The location circuitry 3646 can refrain from beeping in response to determining the RSS is greater than (or equal to) a threshold value.

Figure 37:
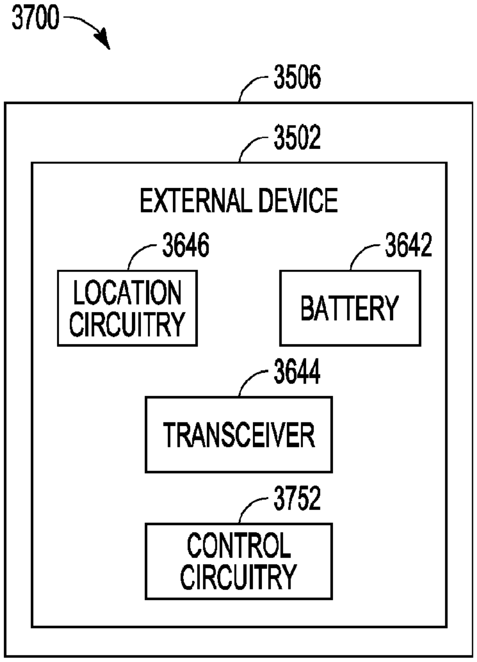
FIG. 37 illustrates, by way of example, a block diagram of an embodiment of a system that includes an external device in a pocket.

FIG. 37 illustrates, by way of example, a block diagram of an embodiment of a system 3700 that includes a single external device (the device 3502) in the pocket 3506. As is illustrated in FIG. 37, the battery 3642 can be included internally to a housing of the external device 3502, such as to be located between a top cover and a bottom cover of the housing.

Figure 38:
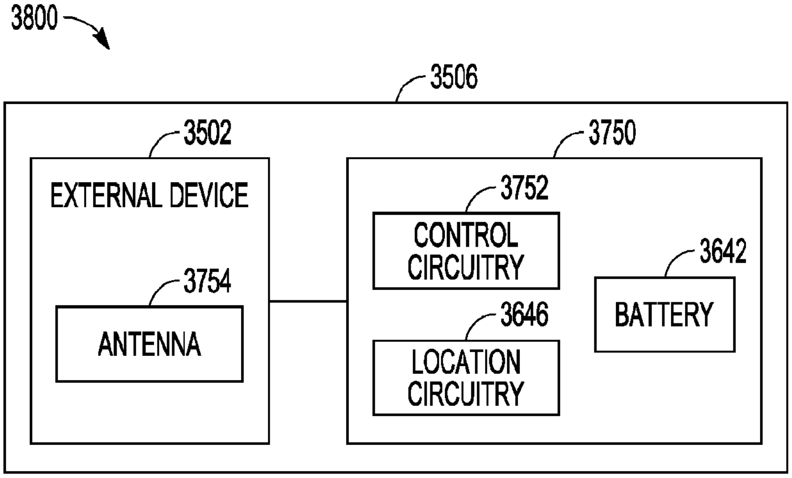
FIG. 38 illustrates, by way of example, a block diagram of an embodiment of a system that includes multiple external devices in a pocket.

FIG. 38 illustrates, by way of example, a block diagram of an embodiment of a system 3800 that includes multiple discrete external devices (the device 3502 and another circuitry 3750) in the pocket 3506. The system 3700 is similar to the system 3700, with the system 3800 including an antenna 3754 in the external device 3502, with some or all of the remaining circuitry external to the external device 3502. The antenna 3754 can be a component of a transceiver of the source 102, such as along with other circuitry. The control circuitry 3752 can be configured to provide one or more signals to the transceiver or antenna to cause the antenna to radiate electromagnetic energy, such as to the implanted device 3504. In one or more embodiments, the battery 3642 and/or the circuitry 3750 can be housed between a top cover and a bottom cover, such as to help radiate heat away from a user's body.

The antenna 3754 and/or the circuitry 3750 can provide an indication of the location of the external device 3502 relative to the implanted device 3504. The circuitry 3750 can include a motor that can cause a vibration to modulate as the external device 3502 gets closer to/farther from the implanted device 3504. The circuitry 3750 can provide an alert to the patient if the implanted device 3504 inside the patient shifts relative to the external device 3502, such as can be detected by monitoring the RSS. The frequency at which the antenna 3754 radiates electromagnetic energy can be programmable. The circuitry 3750 can monitor an amount of energy available from the battery 3642 and provide a low battery warning (e.g., a sound or vibration) if the amount of energy available from the battery 3642 drops below a specified threshold. The circuitry 3750 can provide an indication to turn on an implanted device 3504 for treatment. The circuitry 3750 can be connected to a network, such as to provide alerts from a mobile phone or by email.

Devices that include a power transmitter, such as the external device 3502, can "overheat" and cause discomfort or burn human skin unless they are carefully designed, especially when the device needs to be near the human body to operate properly. Data from at least one study indicates a "safe" heat absorption level of approximately 40 $mW/cm^2$. Near the overheating point, skin temperature increases approximately 0.80° C. for each additional 10 $mW/cm^2$ of absorbed power. During normal operation, the external source 102 heats as a side effect of performing its intended function. Touching a heated device to human skin initiates a thermal transient transfer followed by a steady state. Using a pocket or sleeve around a device, or a device including an external housing, as discussed herein, such as can be used along with a device configured to transfer heat away from the body, can avoid user discomfort and/or skin burns.

Considering steady-state and to verify thermal safety, a designer can place a finished device in ambient air, heat the device to steady state, measure a device's surface temperature, and compare the surface temperature to a "known-safe" temperature, such as 41° C. If the measured temperature is less than the "known-safe" or threshold temperature, the designer can conclude that the device will not cause pain or burning of the skin. Although checking the thermal safety of a device by comparing the surface temperature to the "known safe" temperature may be convenient, the following factors may limit its applicability: 1) when compared to human skin, the ambient air presumably provides a higher thermal resistance to heat moving from the tested device; and 2) the higher thermal resistance forces the device to reach a higher temperature than it reaches when in direct contact to a material or skin. Using ambient air, the thermal load likely produces conservative test results. However, device performance generally improves with increasing power dissipation, so the test may be unjustifiably conservative. Knowing skin-temperature response and the heat output per area of the external device 3502, the resulting skin temperature can be calculated without calculating or measuring an actual device temperature.

A problem solved by one or more embodiments discussed in this subsection can include a wearable element (e.g., a garment or other body-fitting apparatus or accessory) with a form factor that will conveniently and discretely situate an external device, such as a wireless power transmitter, over a desired anatomical target (e.g., at a desired location on or near the body). Another problem solved by one or more embodiments discussed in this subsection can include an external housing for the power transmitter that will not burn, heat, and/or generally be felt by the patient.

An undergarment with a pocket or other mechanism in which an external device can be situated near the desired anatomy and therefore the implanted device. An external power transmitter device and/or pocket/sleeve can dissipate heat, such as produced by the power transmitter, away from the body. In some examples, the form factor can include the wearable element, a battery to power the external device 3502, an antenna and other related electronics, a housing for the antenna and circuitry, and/or a sleeve or pocket in which to situate the housing.

As previously discussed, human skin can be sensitive to the heat dissipated through a surface of a power transmitter device. Accordingly, the skin or body surface temperature at or near the external device, or other components near the human body, can be an important constraint. A temperature at a surface of an external device may become too hot to touch, thus leading to an uncomfortable user experience. For example, a high temperature at a housing surface may cause a user to stop using the device altogether. Further, high temperature surfaces can become a safety hazard due to localized skin burning or irritation. Thus, reducing a maximum temperature of an external device can be an important consideration.

An advantage of one or more embodiments discussed herein can include increased user comfort, for example when a user wears an external device using a wearable element. The systems discussed herein can be ventilated to help with heat and moisture regulation. The wearable element can have a material layer, configured for use at or adjacent to skin, that has particular characteristics that optimize for air and water vapor permeability, rapid moisture absorption and conveyance capacity, mitigation of or resistance to dampness, rapid drying, and/or water or other fluid absorption. The systems discussed herein can have dimensional stability when wet, can be made of durable or resilient materials, can be relatively easy to clean, can be lightweight, soft, and generally pleasant to the touch. The systems can include a high heat transfer characteristic away from the human body.

In accordance with several embodiments, the external device 3502 can be positioned (that is, retained in a chronic or static position relative to the body) above the left or right S3 foramen using a wearable element, such as near an implanted device. The S3 foramina are usually located about 11 cm from the anal verge or 9 cm cephalad to the tip of the coccyx. The S3 foramina are usually located 1.5-2 cm lateral to the midline at the level of the sacral notches or about 9 cm above the coccygeal drop-off. The external device 3502 can include the location circuitry 3646 that will help the patient determine when the external device 3502 is placed at or over a proper location relative to the implanted device. The S3 foramina are located generally one finger breadth above and below the S4 and S2 foramina, respectively. In an example, a garment configured to hold or position the external device 3502 can be provided in multiple sizes to accommodate different user body types and sizes. In an example, relative dimensions of the garment can be adjusted depending on body type. For example, a distance between a waistband of an underpants garment and an external device pocket can be different between large and small versions of the garment to better position the pocket, and therefore the external device 3502, relative to a target by S3.

The external device 3502, such as can include the battery 3642 and/or other circuitry, can be placed in a garment pocket or in a sleeve that includes layers similar to those discussed herein. A polymer coating can be used to line an inside of a sleeve or pocket, such as to make it waterproof In one or more embodiments, the wearable element can include a compression band, or other extensible and retractable member, or elastic band, configured to compress or bias the external device 3502 toward a desired location relative to a body feature or skin surface location when the element comprising the pocket or sleeve is worn. The compression band can be integrated into the wearable element. The compression band can include conduits (e.g., through-holes) large enough to allow for heat dissipation and breathability. The compression band can have multiple channels or channels of different sizes. The compression band can have a variety of elasticity properties. The compression band can be about 0.5 mm-2 mm thick (e.g., 0.5-1 mm, 1 mm-1.5 mm, 1.5 mm-2 mm, 1 mm-2 mm, 0.5 mm-1.5 mm, overlapping ranges thereof, or any value within the recited ranges). The compression band can include conduits that are larger in a y direction (e.g., parallel to a height of a user) compared to an x-direction (e.g., perpendicular to the height of the user). Such a configuration can help conserve an elasticity of the band, while allowing for ventilation in the band.

In some embodiments, more than one pocket 3506 can be used, such as to provide a means to place an external device, such as for multiple different implanted device locations in one garment. In one or more embodiments, there can be a pocket for the external device 3502. The pocket can be configured to be positioned above the sciatic notch. The pocket can span a width starting from about 30 mm lateral from the center of the left S3 foramen to about 30 mm right from the center of S3 foramen. In one or more embodiments, the pocket can have a total width of about 140 mm (about 70 mm to the right of the midline, and about 70 mm to the left of the midline). Other dimensions may be used as desired and/or required (e.g., length of between 60 mm and 200 mm, between 60 mm and 100 mm, between 70 mm and 150 mm, between 90 mm and 180 mm, between 100 mm and 160 mm, between 120 mm and 180 mm, between 130 mm and 150 mm, between 140 mm and 200 mm, overlapping ranges thereof, or any value within the recited ranges). In one or more embodiments, there can be a left pocket and a right pocket, each above and on opposite sides of the sciatic notch, such as can include a back pocket on the back left side above the left S3 foramen and another back pocket that sits directly above the S3 foramen. Each pocket can be about 60 mm in width by 60 mm in height. Other dimensions or shapes may be used as desired and/or required (e.g., 50 mm×50 mm, 70 mm×70 mm, 60 mm×50 mm, 50 mm×60 mm).

As previously discussed, mechanisms can be used to keep the external device 3502 at a proper location within the pocket 3506. Such mechanisms can help users remove or replace the external device 3502, such as without compromising functionality of the external device 3502 or the implantable device 3504. The attachment mechanisms discussed herein can include, among other things, a mechanical fastener such as a fabric hook and loop fastener (e.g., a VELCRO® fastener), a SCOTCH® fastener, or magnets on the unit to secure to a corresponding fastener (e.g., another VELCRO® fastener in the pocket), a zipper, gussets, bellows, layers with off-set slits, or extra material that folds over the pocket 3506 can be used to close off the pocket 3506 from the external environment. A bottom layer of a pocket or sleeve can be covered with a sticky or tacky material, such as to help hold the device in place and/or to keep the pocket closed. In some examples, the pocket 3506 can comprise one or more layers at least partially covered in a rubber/silicone/sticky type gel or similar material to help hold the external device 3502 in place. The wearable element can be placed over the external device 3502 with, e.g., a rubber or gel lining covering substantially all of an inside surface of the pocket, to hold the external device 3502 in place. In an example, a sleeve for the external device 3502 can include spandex or SPANX® material that can cover or surround the external device 3502. The sleeve for the external device 3502 can include a flap, such as to help encapsulate or retain the external device 3502 in a specified location relative to a garment.

In one or more embodiments, a system can include a wearable element configured to be worn by a patient, and having an external device coupled thereto and configured to send and/or receive a wireless signal to communicate with an implanted device. The wearable element can include an attachment mechanism to situate the external device near (e.g., directly above, below, or to the side of) the S3 foramen so the external device will be in proximity to the implantable element. The external device 3502 can be placed at multiple locations on the wearable element. The external device 3502 can include an antenna configured to be positioned in proximity to the implanted device and configured to receive data from the implanted device or send power to the implanted device 3504. The external device 3502 can include location circuitry that provides an audible or tactile indication of a proper location of the external device 3502 on the wearable element, such as relative to the implanted device when the wearable element is worn. The external device 3502 can be a first external device and the system can include a second external device, wherein the first and second external devices are optionally coupled and configured to be positioned at respective spaced apart locations on the wearable element. The second external device can be configured to provide power to the first external device. The second external device can include a flexible battery adapted to flex in response to motion of a user wearing the flexible battery. The wearable element can include one or more elastic straps. The wearable element can accommodate a variety of patient sizes and shapes. The wearable element can include one or more of an undergarment, a pouch, a belt, and an adhesive patch. The wearable element can include at least one pocket formed therein. In one or more embodiments, the position of at least one pocket can be movable relative to a body portion of the wearable element.

Examples of different shapes, sizes, and styles of wearable elements include tight or non-tight shorts, such as mid-thigh shorts, high-thigh shorts, high-waist shorts, and/or mid-thigh shorts, briefs, such as high-waist briefs and/or retro briefs, hipsters, such as hi-hipster panty, panty boy shorts, and/or girl shorts, thongs, such as high-waisted thong, a bodysuit, such as an open bust bodysuit, a closed bust bodysuit, and/or a mid-thigh bodysuit suit, and pantyhose, such as a high waist and/or a no-show panty hose.

Some patients may not need or use constant stimulation from an implanted device but can use stimulation intermittently, such as can be controlled or administered using the external device 3502 in communication with the implanted device 3504. This can be due, at least in part, to carryover effects of the electrostimulation. For example, a patient may only need stimulation one hour every 24 hours for continued efficacy of the therapy.

In an example, therapy control circuitry in an external device can include a timer. The control circuitry can provide an indication to the user (e.g., noise, vibration, pulse, or other indication) in response to the timer beginning or expiring, such that the user can know how long to wear or use the external device 3502. The control circuitry can track a dosage the patient has received. The control circuitry can calculate a decay of the dosage to inform the patient when a subsequent stimulation dose is to be administered.

The external device 3502 can inform the user how long the device has been stimulating or has been turned on, such as using the control circuitry. The control circuitry can automatically stop providing electrical power to the antenna in response to determining an appropriate stimulation dosage is reached.

The control circuitry informs a user when stimulation begins or ends, such as using noises and/or vibrations. The control circuitry can alert the user to indicate when the user is to remove the external device 3502 and/or when the user is to place the external device 3502 near the implanted device 3504. The control circuitry can remind or provide an alarm to a user to indicate that the user should put the external device 3502 near the implanted device 504, such as in response to determining the external device 3502 is not sufficiently close to the implanted device 3504. In one or more embodiments, the control circuitry may constantly or intermittently remind the user to position the device for therapy delivery, such as until the external device 502 is correctly placed for stimulation. The reminder can have a “snooze” feature such as to remind the user after a specific amount of time has elapsed. The control circuitry can include a Bluetooth®, Wi-Fi®, Zigbee®, or other short range connection circuitry that can interface with a phone, through which a user can program the control circuitry, such as to customize alarm settings.

There can be a setting for a user who wears the external device 3502 all day regardless of whether the stimulation is on or off. The external device 3502, such as through the control circuitry, can inform the patient when stimulation begins, ends, and/or can provide the patient with information about a duration of stimulation. The external device 3502 can send an alert (e.g., an email, text, or other audible, visual, or textual reminder) that a user can access via a mobile device (e.g., smartphone, tablet, computer via a software application program or a web browser). The alert may be sent over a wireless network. There can be a setting to insert the reminder on the user's calendar, such as through the control circuitry.

The external device 3502 can provide various audible alerts to indicate different alarms. These alarms can be programed through a software application (app) on a mobile device (e.g., smartphone or computing device). The external device can be allowed to store a certain amount of data in its memory before it would have to be connected to the mobile device (e.g., mobile phone), software application on the mobile device, or network, such as to upload the data before it is overwritten. The memory can track how long, for how many days, hours, etc. a user has received stimulation from an implanted device, such as by using the software application.

The external source 3502 can be pre-programmed with a selection of therapy regimes, such that the user can select using the software application. The user defined regimes may also be customized by the user, such as to allow the user to define their own timing settings, reminders, sounds, vibrations, power on, power off, settings, stimulation schedule, etc.

The control circuitry can include a safety feature which prevents over-heating of the external device 3502, such as can include monitoring a temperature of the external device 3502 itself and removing power to the external device 3502 if a threshold temperature is met or exceeded.

A password or other security mechanism can be required by the control circuitry 3752 or the app to adjust stimulation settings, such as power of stimulation, duration, etc., of the stimulation. The control circuitry 3752 can include a Light Emitting Diode (LED) or other light that can be red or green, or whichever color to indicate the device is on, off, or searching for the implanted device, for example.

Figure 39:
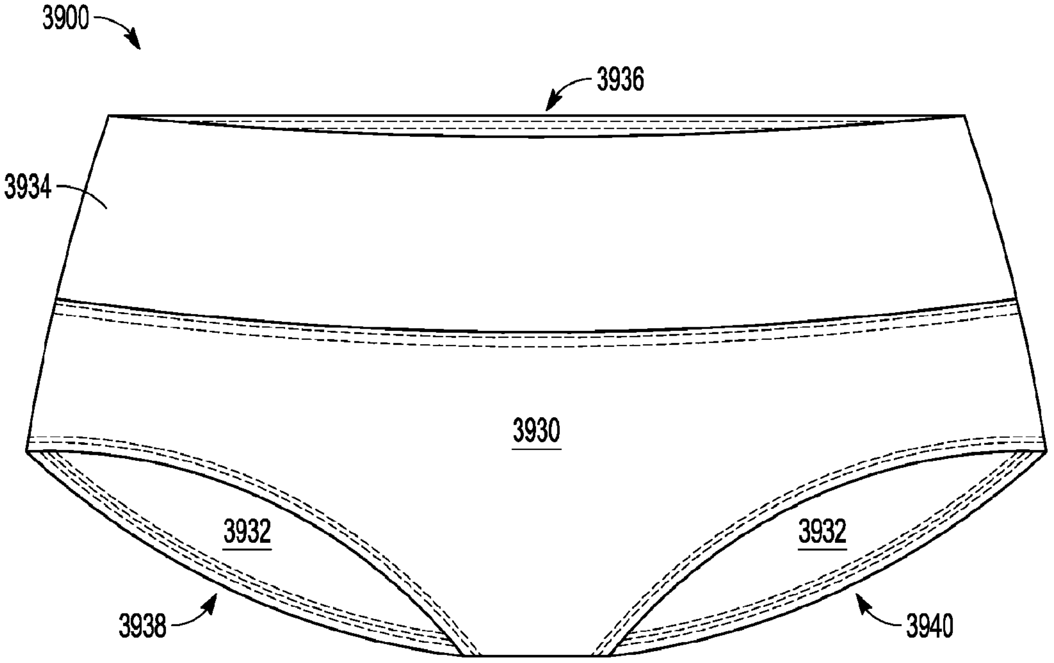
FIG. 39 illustrates, by way of example, a front-view diagram of an embodiment of a garment.

FIG. 39 illustrates, by way of example, a front-view diagram of garment 3900. The garment 3900 includes multiple layers of fabric 3930, 3932. The multiple layers of fabric 3930, 3932 can be of a same or different fabric 3930, 3932. The fabric can include a stretchable, bendable fabric, such as can be elastic. The fabric 3930, 3932 can include a mesh weave or a non-woven fabric. The fabric 3930, 3932 can include one or more materials, such as nylon, cotton, denim, silk, polyester, linen, wool, rayon, chiffon, spandex, a combination thereof, or the like. These are just some examples of types of fabric and the fabric 3930, 3932 can include one or more of these materials or other fabric material.

The garment 3900 includes a waistband 3934. The waistband 3934 can include a material that is same or different from the material 3930, 3932. The waistband 3934 is generally configured to sit on or about the hips of a user when in normal use. The user can slide their legs through a hole 3936 at the waistband 3934. The user can then move respective legs through respective leg holes 3938, 3940, and slide the waistband 3934 over their hips. The waistband 3934 can include a bendable and stretchable fabric that extends over less than half the waistband 3934 and a different fabric or fabrics that extend over the remainder of the waistband 3934.

Figure 40:
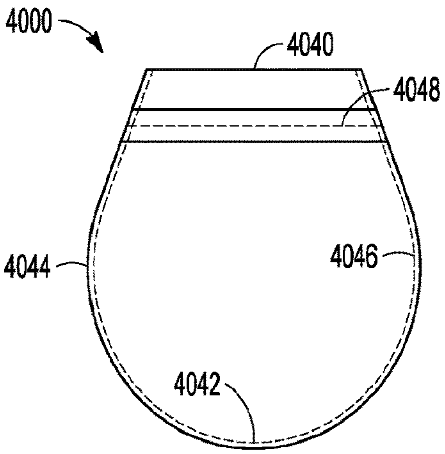
FIG. 40 illustrates, by way of example, a pocket that can comprise a portion of a garment.

FIG. 40 illustrates, by way of example, a pocket 4000 that can comprise a portion of the garment 3900 or another wearable element. The pocket 4000 can include a first edge 4040 and an opposing second edge 4042. The first edge 4040 can be situated closer to a first edge marked by a first fiducial marker 4052 than a second edge marked by a second fiducial marker 4042. The garment 3900 includes sides 4044, 4046 that extend between the top edge 4040 and the bottom edge 4042. The side 4044 opposes the side 4046.

The pocket 4000 can include multiple layers of fabric. A user can access a space between the layers of fabric through a device access port 4048. The device access port 4048 can include an opening between the layers of fabric. The pocket 4000 can comprise a material having the same composition or material type as the material of the fabric 3930, 3932, or can comprise one or more other materials. The device access port 4048 of the pocket 4000 can be offset from a pocket access port 4050 of the garment 3900. The device access port 4048 of the pocket 4000 can be situated closer to a top edge 4056 of the garment 3900 than the pocket access port 4050 of the garment 3900. Having the device access port 4048 of the pocket 4000 offset from the pocket access port 4050 of the garment 3900 reduces the chances that an item in the pocket 4000 inadvertently falls out of the pocket 4000 and out of the pocket access port 4050.

The pocket 4000 can be attached to a garment, such as the garment 3900. The pocket 4000 can be attached at a location on the garment 3900 such that the pocket 4000 rests on or directly above a point on a surface of a user's skin that is closest to a specified foramen of the user. Since foramen are generally symmetric about a longitudinal axis of a spinal column, the pocket 4000 can be attached offset from a center point of the garment.

Figure 41:
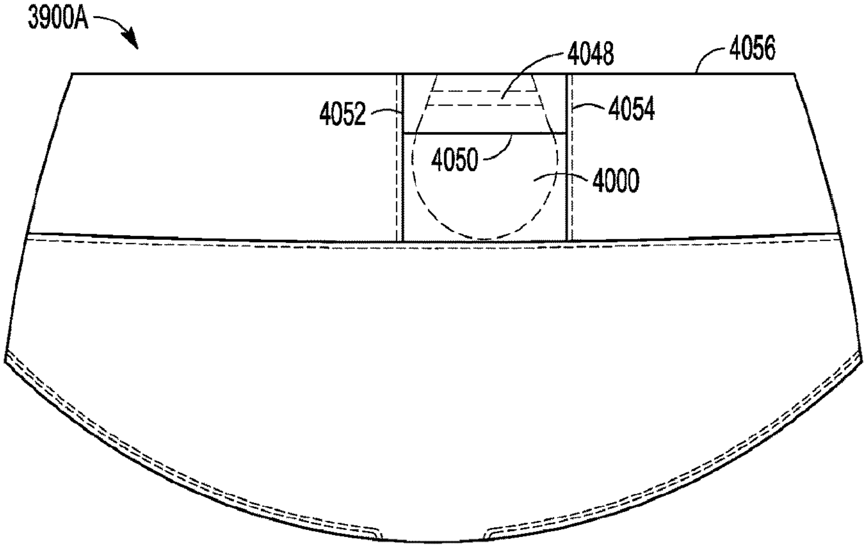
FIG. 41 illustrates, by way of example, an embodiment of underwear with a pocket attached thereto and situated to retain an item, such as an external power unit (EPU), at foramen on a first side of a body.

FIG. 41 illustrates, by way of example, an underwear garment 3900A with the pocket 4000 attached thereto and situated to retain an item, such as an external power unit (EPU), directly over a foramen on a first side of a body. The example in FIG. 41 situates the pocket 4000 on a right-hand side of the user's body and proximate a foramen on the right side of the patient's body. The pocket 4000 is illustrated in dashed lines to indicate that it is provided partially or entirely between other layers of the garment 3900A.

The pocket 4000 can be accessed by a user through the pocket access port 4050 in the garment 3900A. The pocket access port 4050 in the example of FIG. 41 includes an envelope pocket opening where one fabric piece overlaps another fabric piece to create a pocket. Alternatively, to the envelope pocket opening can include a welt pocket opening, a trim closure (e.g., one or more of a zipper, hook and loop fastener, patch pocket with or without a flap, envelope opening, pocket bag, or the like). The pocket 4000 can be sewn, fastened, buttoned, or otherwise attached to the garment 3900 in a space that is accessible through the pocket access port 4050.

The garment 3900A in the example of FIG. 41 includes the first and second fiducial markers 4052, 4054 that indicate respective left and right boundaries of a desired location for the pocket 4000. The fiducial markers 4052, 4054 can be provided to help ensure that the pocket is situated such that the pocket 4000 rests on directly above a point on a surface of a user's skin that is closest to a specified foramen of the user when the garment 3900A is worn.

In a particular illustrative example, an enclosure can be different from a pocket. An enclosure can include an area that is sealed. In contrast, a pocket can include a small bag or retaining compartment that is sewn into or otherwise coupled to a garment and the pocket is generally not sealed. For example, a pocket in a pair of pants or jeans can be considered to be other than an enclosure because such a pocket may not include a sealing mechanism. Example sealing mechanisms include a hook and loop fastener, a button, stretchable and bendable fabric with a taper, situating a pocket in an envelope pocket (making the pocket in the envelope pocket opening an enclosure), compressing a pocket between layers of fabric making the pocket an enclosure (as in some example teachings of this disclosure), a zipper, or the like.

Figure 42:
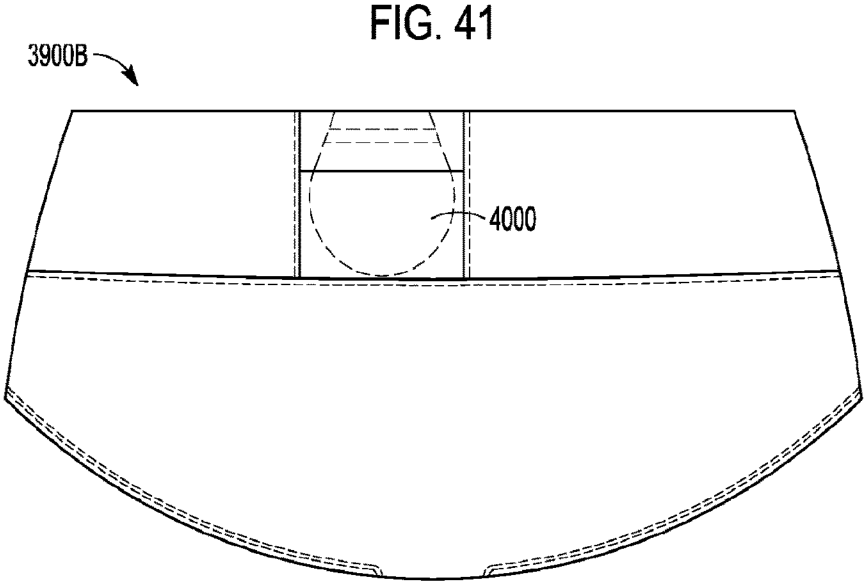
FIG. 42 illustrates, by way of example, an embodiment of a garment with a pocket attached thereto and situated to retain an item, such as an external power unit (EPU), at foramen on a second, opposite side of a body.

FIG. 42 illustrates, by way of example, another underwear garment 3900B with the pocket 4000 attached thereto and situated to retain an item, such as an external power unit (EPU), at or near a foramen on a second, opposite side of a body. The example in FIG. 42 situates the pocket 4000 on a left-hand side of the body of the patient and proximate a foramen on the left side of the body of the patient.

Figure 43:
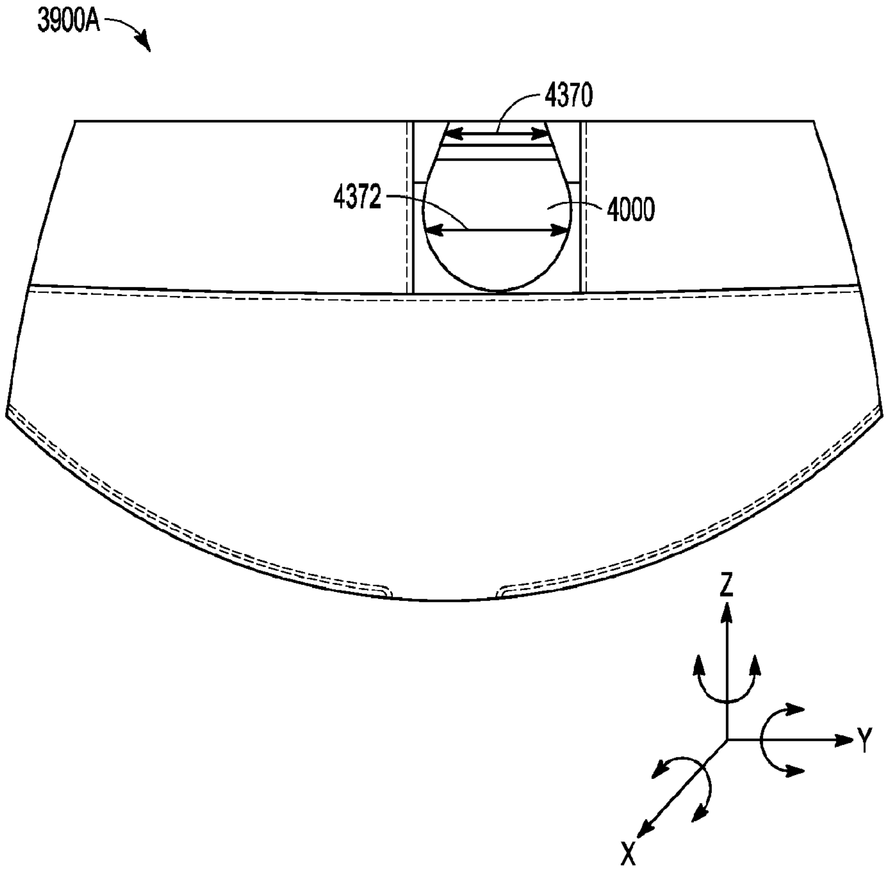
FIG. 43 illustrates, by way of example, the garment of FIG. 41 with the pocket situated external to the garment and attached to the garment.

FIG. 43 illustrates, by way of example, the garment 3900A of FIG. 41 with the pocket 4000 situated outside of the pocket access port 4050, such as external to the garment 3900A while still attached to the garment 3900A. The pocket 4000 can be removed by a user, such as by penetrating the space between the fabric 3930, 3932 through the pocket access port 4050 (e.g., an opening in the example illustrated in FIG. 41). The user can grasp the pocket 4000 and slide it out of the space between the fabric 3930, 3932 through the pocket access port 4050. The pocket 4000 is then substantially external to the garment 3900A as illustrated in FIG. 40 and contents of the pocket 4000 can be more easily accessed by a user, such as to access or service an EPU configured for use in the pocket 4000.

The orientation of the edges 4040, 4042 (see FIG. 40) and sides 4044, 4046 relative to each other and the hole 3936 (see FIG. 39) can be the same regardless of whether the pocket 4000 is situated internal or external to the garment 3900A. In other words, the edge 4040 can be closer to the hole 3936 than the edge 4042, regardless of whether the pocket 4000 is inside or outside of the pocket cavity in the garment 3900, or between material layers of the garment 3900. The orientation being the same can be understood to mean that the shape of the pocket 4000 does not change whether it is internal or external to the garment 3900. The orientation being the same can be understood to mean that an item in the pocket 4000 remains in the pocket 4000 through the process of removing the pocket 4000 from, or situating the pocket 4000 inside of, the space between the fabric 3930, 3932 layers of the garment 3900. In some prior garments, a pocket of this disclosure (as opposed to an enclosure) can be situated outside the garment, but the edges of the pocket are no longer oriented the same relative to the garment, or the pocket is deformed or emptied when removed from the garment.

When the pocket 4000 is outside the garment 3900A it can have three or more degrees of freedom in its motion. The pocket 4000 illustrated in FIG. 43 is free to move with motion along pitch, yaw, roll, x-axis, and y-axis. This freedom of motion allows the user more freedom in removing the pocket 4000 from the space between the fabric without adversely affecting the attachment to the garment 3900. The axes are labelled relative to the body such that the x-axis corresponds to forward and backward motion, the y-axis corresponds to left and right motion, and the z-axis corresponds to up and down motion. Rotation about the x-axis is roll, about the y-axis is pitch, and about the z-axis is yaw.

The pocket 4000 can be tapered such that it includes a narrower neck region relative to a body region thereof. For example, the pocket 4000 can be narrower about or near its opening than it is elsewhere, such as at its widest point, at a body portion thereof, wherein the pocket 4000 is configured to hold an EPU. In the example of FIG. 43, width is understood to be along the y-axis. An arrow 4370 indicates that the pocket 4000 is narrower about its opening region than it is at its body region, which is indicated by another arrow 4372. The taper of the pocket 4000 can help the pocket 4000 retain an item therein even while the pocket 4000 is transitioned between outside and inside of a space between the fabric 3930, 3932 layers of the garment 3900A.

Figure 44:
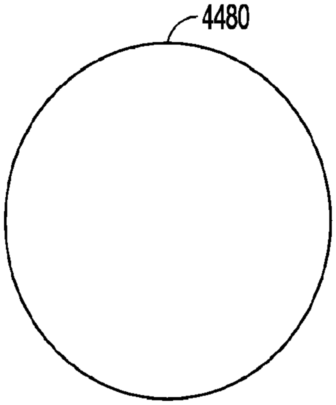
FIG. 44 illustrates, by way of example, a top view diagram of an embodiment of a standoff.

FIG. 44 illustrates, by way of example, a standoff 4480. The standoff 4480 can include foam, polymer, rubber, or other breathable material. The standoff 4480 provides a gap between an item situated in the pocket 4000 and the fabric 3932 in contact with the skin of the user. The standoff 4480 can help the source 102 form a propagating wave that propagates to a therapy target in the user. The standoff 4480, from the perspective of the source 102, can provide an air gap through which an electromagnetic wave can propagate.

Figure 45:
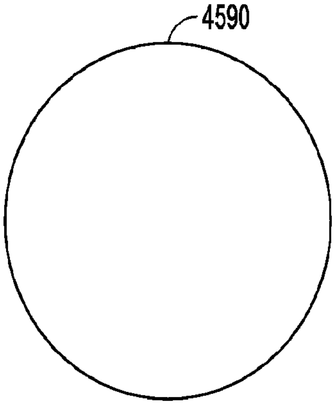
FIG. 45 illustrates, by way of example, a top view diagram of an embodiment of a thermal protective material.

FIG. 45 illustrates, by way of example, a thermal protective material 4590. The thermal protective material 4590 can include a high-temperature reusable surface insulation (HRSI), fibrous refractory composite insulation (FRCI), toughened unipiece fibrous insulation (TUFI), low-temperature reusable surface insulation (LRSI), reinforced carbon-carbon (RCC), among other materials. The thermal protective material 4590 can reflect thermal energy towards a body-external side of the fabrics 3930, 3932. The thermal protective material 4590 can be situated in the pocket 4000 and closer to a patient's skin than the standoff 4480 (see FIG. 44). The orientation of thermal protective material 4590 and the standoff 4480 relative to the patient's skin can remain the same through the process of removing the pocket 4000 from the space or inserting the pocket 4000 in the space. That is, the thermal protective material 4590 can remain closer to the patient's skin while the pocket 4000 is in the space, outside the garment 3900, or while transitioning from within the space to external to the garment 3900.

Figure 46:
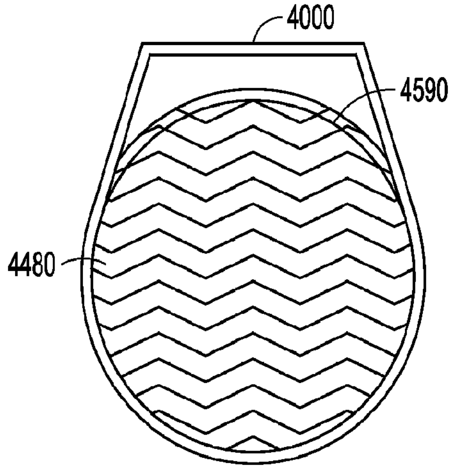
FIG. 46 illustrates, by way of example, an embodiment of a pocket with the standoff and the thermal protective material of FIGS. 44 and 45, respectively.

FIG. 46 illustrates, by way of example, the foam standoff 4480 and the thermal protective material 4590 of FIGS. 44 and 45, respectively, situated in the pocket 4000. The thermal protective material 4590 is illustrated as being behind the standoff 4400 in FIG. 46. In the example view of FIG. 46, the user's skin would be behind the thermal protective material 4590 in normal use.

Figure 47:
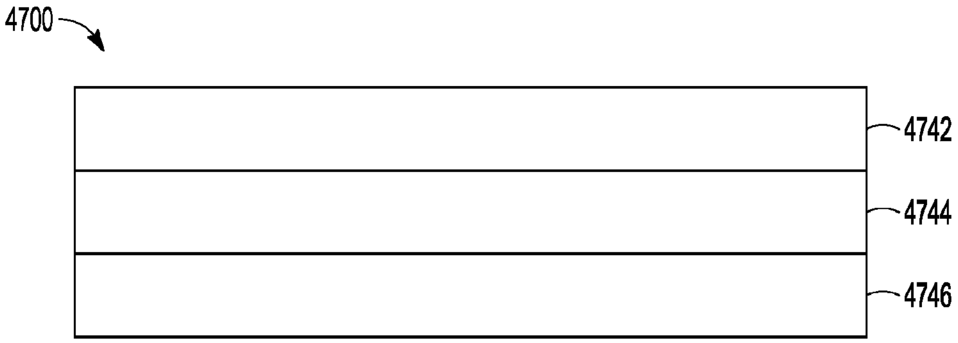
FIG. 47 illustrates, by way of example, an embodiment of a fabric stack.

FIG. 47 illustrates, by way of example, an embodiment of a fabric stack 4700, at least a portion of which can help increase comfort for a user with incontinence, for example. The stack 4700 as illustrated includes three layers of fabric 4742, 4744, and 4746. The fabric 4742, when the garment is worn, is closer to the skin of the user than the layers of fabric 4744 and 4746. The fabric 4744 is situated between the fabric 4742 and the fabric 4746. The fabric 4746 can be in view when the garment is worn.

The fabric 4742 can be configured to wick moisture to the fabric 4744. The fabric 4742 can include Polyethylene terephthalate (PET) (POLYESTER); Polyurethane fabrics, including Lycra (SPANDEX/ELASTANE). The fabric 4744 can absorb and retain the moisture wicked from the fabric 4742. The fabric 4744 can include Cotton/Polyester blend fabrics; Polyethylene terephthalate (PET) (POLYESTER); Polyurethane (PU). The fabric 4746 can help the garment retain shape and visual appeal. The fabric 4746 can include Polyethylene terephthalate (PET) (POLYESTER); Polyurethane fabrics, including Lycra (SPANDEX/ELASTANE); Polyamide fabrics, including (NYLON).

Figure 48:
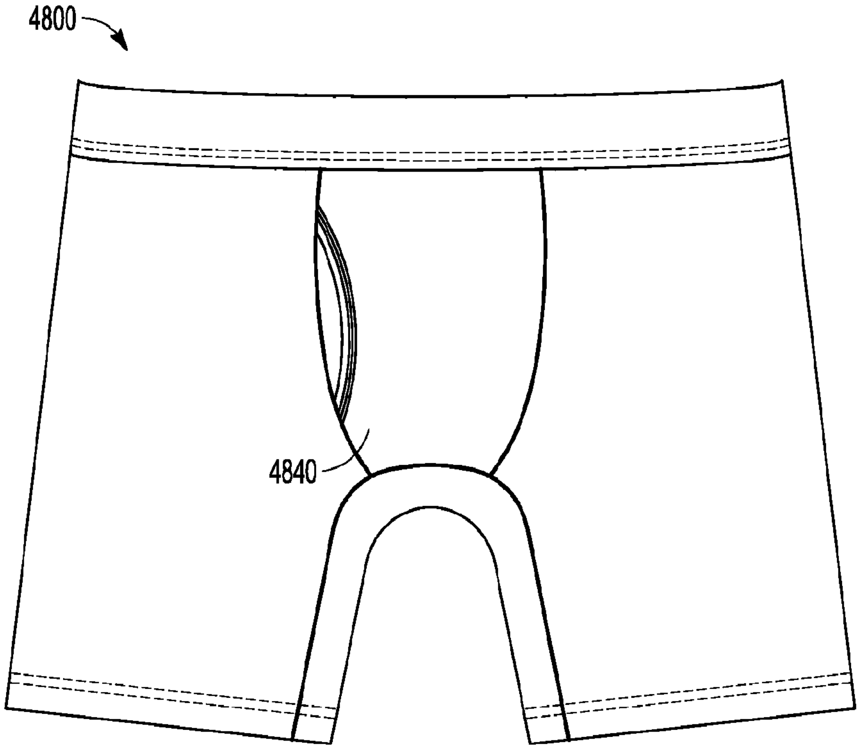
FIG. 48 illustrates, by way of example, a front-view diagram of an embodiment of a boxer brief.
Figure 49:
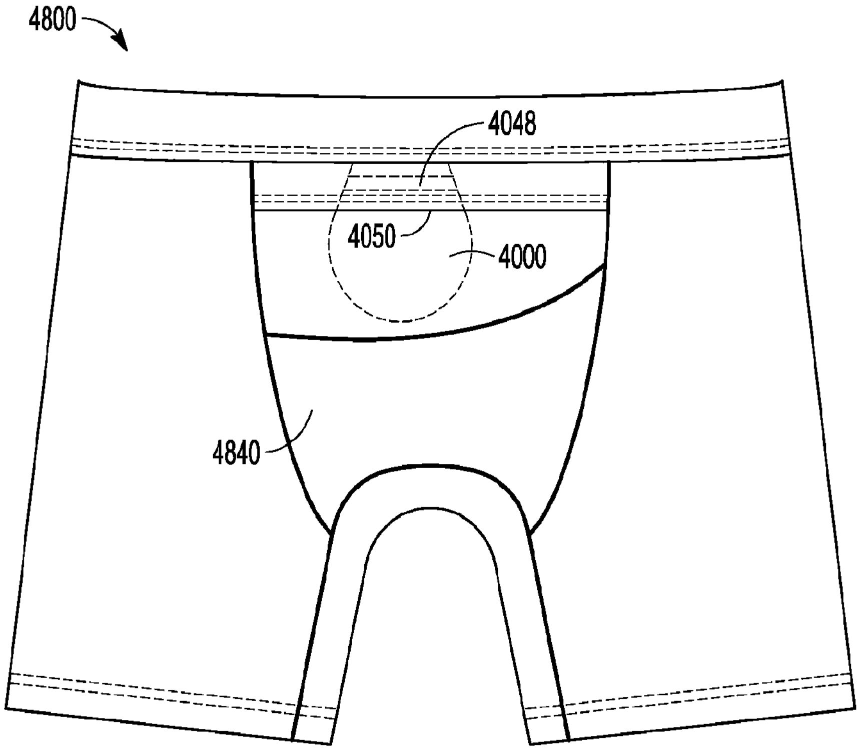
FIG. 49 illustrates, by way of example, a back-view diagram of the boxer brief illustrated in FIG. 48.

FIG. 48 illustrates, by way of example, a front-view diagram of an embodiment of a boxer brief 4800. FIG. 49 illustrates, by way of example, a back-view diagram of the boxer brief 4800 illustrated in FIG. 48. Similar to the garment 3900, the boxer brief 4800 can comprise, or can be coupled with, the pocket 4000, such as between layers of fabric of the boxer brief 4800. The layers of fabric for the boxer brief 4800 can include two layers of fabric between which the pocket 4000 can be situated. In a crotch region 4840 of the boxer brief 4800, two of the layers of the stack 4700 can be used to help move moisture away from the skin of the user. The layers can include the fabric 4742 and 4744. The user can access the pocket 4000 through a pocket access port 4050 in the boxer brief 4800 in a manner similar to that described above in the discussion of the garment 3900.

Figure 50:
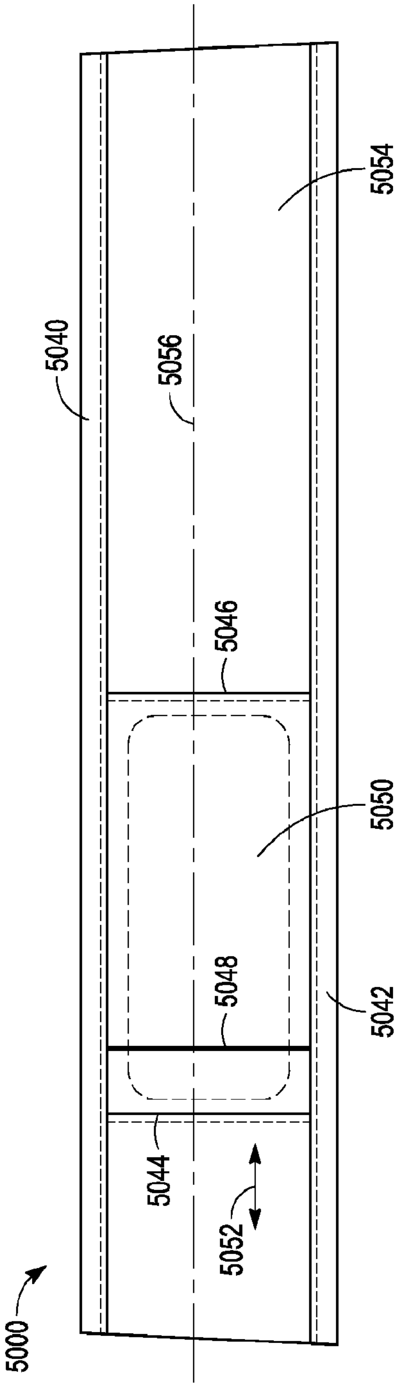
FIG. 50 illustrates, by way of example, a front-view diagram of an embodiment of a band garment.

FIG. 50 illustrates, by way of example, a front-view diagram of an embodiment of a band garment 5000. The band garment 5000 includes two or more layers of a same or different fabric 5054. The two or more layers of fabric 5054 are stitched or otherwise secured at opposing top and bottom edges 5040 and 5042, respectively. An access port 5048 can be formed in one of the layers of fabric 5054. The access port 5048 can be oriented perpendicular to a longitudinal axis (indicated by dashed line 5056) of the band garment 5000. A space between the layers of fabric 5054 can be accessed through the access port 5048. The space that can be accessed can be constrained by seams 5044, 5046 oriented generally parallel to the access port 5048 and extending between stitching on the top edge 5040 and stitching on the bottom edge 5042. One or more items 5050 can be stored in the space formed by the stitches and accessible through the access port 5048. Items can be placed in and removed from the access port 5048 in a direction indicated by arrow 5052 (generally parallel with the longitudinal axis of the band garment 5000). In an example, the access port 5048 includes partially overlapping layers or portions of the fabric 5054 layers. In an example, the pocket 4000 can be coupled at or near the access port 5048.

Figure 51:
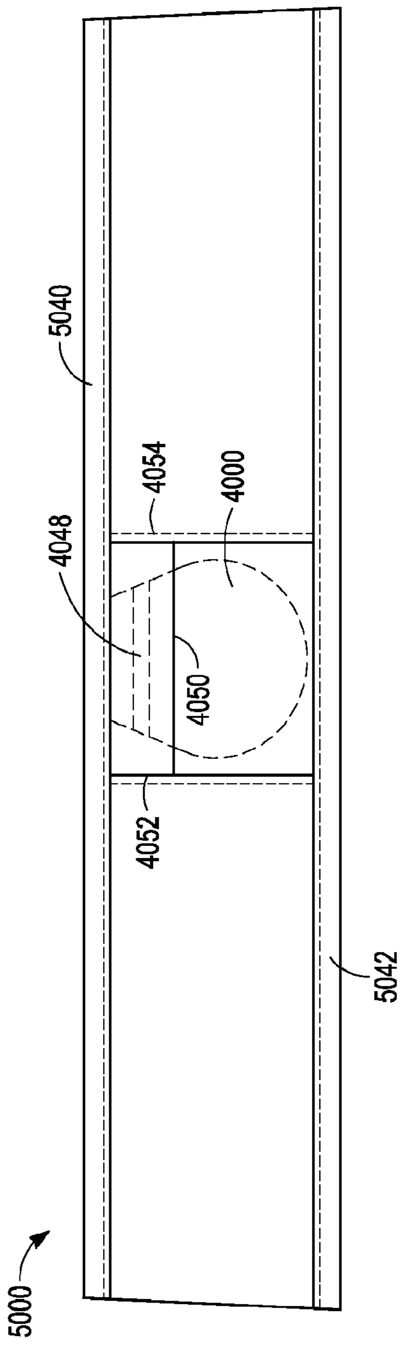
FIG. 51 illustrates, by way of example, a back-view diagram of an embodiment of the band garment of FIG. 50.

FIG. 51 illustrates, by way of example, a back-view diagram of an embodiment of the band garment 5000 of FIG. 50. The band garment 5000 as illustrated includes the pocket 4000 accessible through the pocket access port 4050 similar to the garment 3900. The pocket 4000 is accessed and functions in the same way the pocket 4000 operates in the garment 3900.

Improved Fixation of Implant

As mentioned elsewhere, the implantable device 110 can wander, migrate, or otherwise move after implantation. What is desired is improved fixation structures and methods to help reduce the amount of motion after implantation. Embodiments discussed herein can provide an increased tensile resistance that must be overcome to cause an implant to move after placement. The increased tensile resistance reduces a likelihood that the implantable device 110 moves after implantation.

Some embodiments can provide a tissue-agnostic fixation method. Embodiments can provide a fixation technique that improves implant mechanical integrity and/or reduces a susceptibility of the implant to movement or migration.

For incontinence or other foramen-adjacent therapies, an implantable device fixation element that is deployed via or within the foramen, such as beneath or within a muscle or ligament layer, can help the device resist migration or outward movement. Some components of the implantable device 110 can be less likely to fracture when the implantable device 110 interfaces are contained or disposed anterior to the foramen. This can beat least in part because deeper tissues can be more dense or fibrous and can provide more resistance against outward implantable device 110 movement. An ambulatory movement can cause tissue movement that in turn applies a force to a proximal portion of an implanted body. A deeper positioning, such as into the foramen, can help reduce an impact of applied forces due to ambulatory movement or other external forces.

Figure 52:
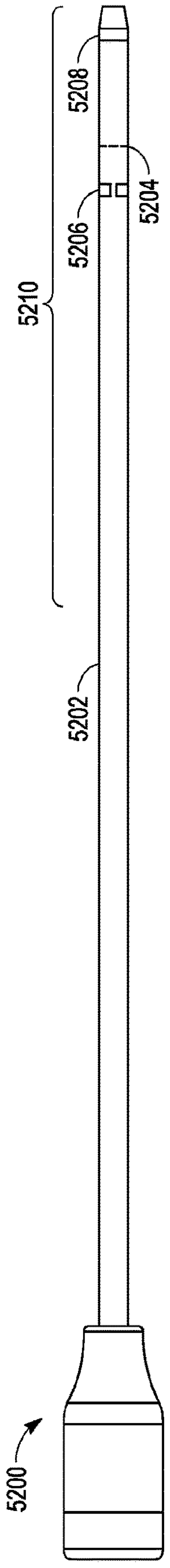
FIG. 52 illustrates, by way of example, a side view diagram of an embodiment of a sheath.

FIG. 52 illustrates, by way of example, a side view diagram of an embodiment of a sheath 5200 that can be used for implantation of the implantable device 110. In an example, the sheath 5200 is or comprises an introducer for use in implanting the implantable device 110 to a target implant site or location inside of a patient body. The sheath 5200 as illustrated includes a shaft 5202. The shaft 5202 includes a sidewall that forms a lumen through which the implantable device 110 can travel. An inner diameter 5216 of the shaft 5202 is thus greater than a largest outer diameter 5218 of the implantable device 110. In an example, an outer diameter of the sidewall of the shaft 5202 can be about the same as an outer diameter of a device migration mitigation component that can be coupled to the implantable device 110.

The sheath 5200 further includes radiopaque markers 5206, 5208. The radiopaque marker 5206, under fluoroscopy, can provide an indication of a location of a breakaway portion 5204. The radiopaque marker 5208, under fluoroscopy, can provide an indication of a proximal portion of an electrode array of the implantable device 110. In one orientation, when in a position proper for implanting the implantable device 110, the radiopaque marker 5208 can be anterior to the sacrum and the radiopaque marker 5206 can be posterior to the sacrum.

The breakaway portion 5204 can be at a location at which a distal portion 5210 of the shaft 5202 is configured to separate from a proximal portion of the shaft 5202. In an example, when a sufficient force is applied to the breakaway portion 5204, the distal portion 5210 of the sheath 5200 separates from the shaft 5202 and is retained about the implantable device 110 (see FIG. 55). The breakaway portion 5204 can indicate a location of a perforation or other feature in the shaft 5202 that makes a portion of the shaft mechanically weaker or separable or severable at the breakaway portion 5204.

Figure 53:
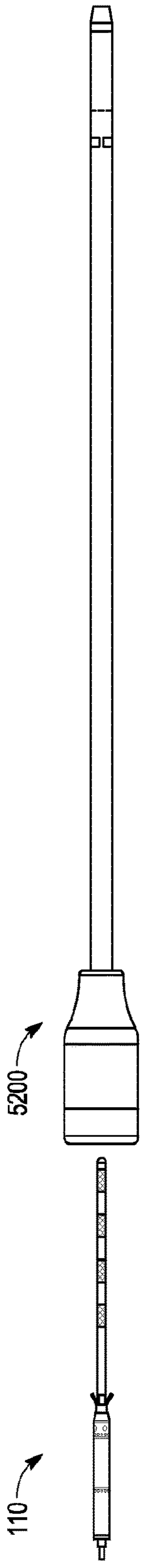
FIG. 53 illustrates, by way of example, a side view diagram of an embodiment of an implantable device and the sheath.

FIG. 53 illustrates, by way of example, a side view diagram of an embodiment of the implantable device 110 traversing into the sheath 5200. The implantable device 110 can move into the lumen of the sheath 5200 such that the electrode array, circuitry housing, frustoconical connector, antenna housing, or a combination thereof, can move at least partially past or through the distal portion 5210 and the breakaway portion 5204.

Figure 54:
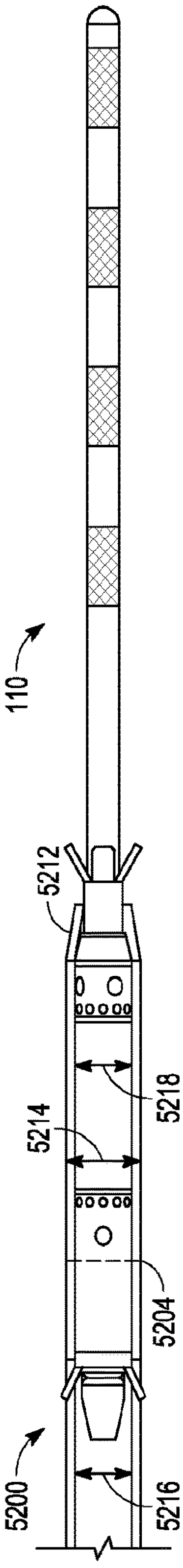
FIG. 54 illustrates, by way of example, a partial cutaway view diagram of an embodiment of an implantable device situated in a distal portion of a shaft portion of a sheath.

FIG. 54 illustrates, by way of example, a side view diagram of an embodiment of the implantable device 110 situated in the distal portion 5210 of the shaft 5202. The distal portion 5210 of the shaft 5202 includes or is adjacent to the breakaway portion 5204. The implantable device 110 as illustrated includes a frustoconical connector 2320 (see, e.g., FIG. 23) that includes a tapered outer diameter. The frustoconical connector 2320, when pushed against a corresponding frustoconical portion 5212 of the distal portion 5210 of the shaft 5202, can apply a force along the shaft 5202 including at the breakaway portion 5204. When the force between the frustoconical connector 2320 and the frustoconical portion 5212 exceeds a strength of connection provided at the breakaway portion 5204, the distal portion 5210 of the shaft 5202 can separate at the proximal end of the breakaway portion 5204 from the remainder or proximal portion of the shaft 5202. The distal portion 5210 of the shaft 5202 breakaway portion 5204 can then move together with the implantable device 110 away from the portion of the shaft 5202 more proximal than the breakaway portion 5204.

Figure 55:
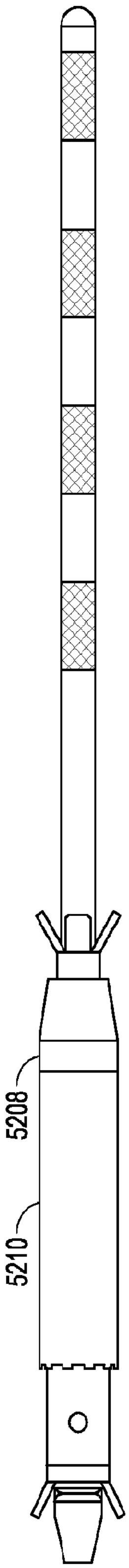
FIG. 55 illustrates, by way of example, a side view diagram of an embodiment of an implantable device and a distal portion of a sheath separated from a shaft portion of the sheath.

FIG. 55 illustrates, by way of example, a side view diagram of an embodiment of the implantable device 110 with the distal portion 5210 of the sheath 5200 separated from the shaft 5202. The distal portion 5210 can include the radiopaque marker 5208. The radiopaque marker 5206 can be more proximal than the breakaway portion 5204 leaving the radiopaque marker 5206 on the shaft 5202 after separation.

The implantable device 110 with the distal portion 5210 has a larger outer diameter 5214 than the implantable device 110 without the distal portion 5210 (the outer diameter 5218). This increased outer diameter 5214 decreases the chances the implantable device 110 migrates. This is, at least in part because the breakaway portion 5204 increases the outermost surface area of the implantable device 110, a force required to move or dislodge the implanted implantable device 110 can be increased. Note that FIGS. 52-55 regard an embodiment in which the distal portion 5210 comprises a portion of the sheath 5200. In some embodiments, the distal portion 5210 can be a discrete component formed separately from and couplable to the sheath 5200. Such a discrete distal portion 5210 is sometimes called a "migration mitigation component" because, when situated about the implantable device 110, the migration mitigation component increases the effective outer diameter of a proximal portion of the implantable device 110. A breakaway junction is formed between where the breakaway portion and more proximal portion of the shaft are coupled.

Figure 56:
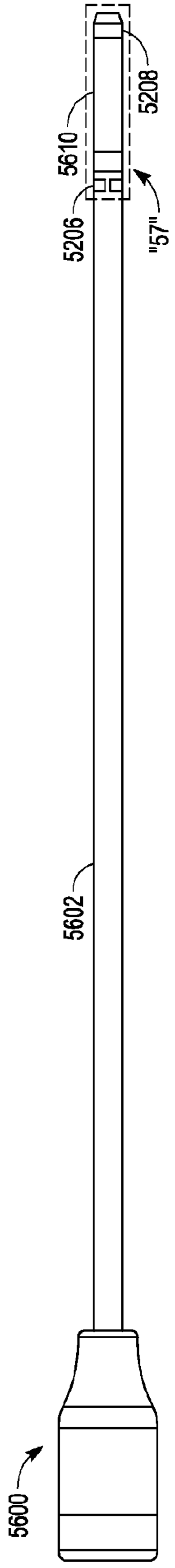
FIG. 56 illustrates, by way of example, a diagram of an embodiment of a sheath system.

FIG. 56 illustrates, by way of example, a diagram of an embodiment of a sheath system 5600. The sheath system 5600 includes a sheath with a shaft 5602 mechanically coupled to a migration mitigation component 5610. The shaft 5602 is similar to the shaft 5202 with the shaft 5602 not including the breakaway portion 5204 or the radiopaque marker 5208. Instead, the shaft 5602 includes the migration mitigation component 5610 and the radiopaque marker 5208 is on the migration mitigation component 5610. The shaft 5602 also differs from the shaft 5202 in that it does not include the frustoconical portion 5212. The shaft 5602 includes an inner diameter that forms a lumen that is generally uniform through its entire length.

Figure 57:
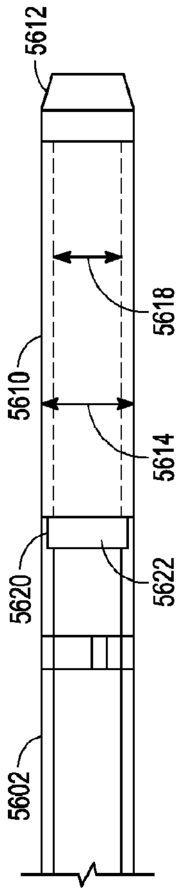
FIG. 57 illustrates, by way of example, a schematic diagram of a portion of the sheath system labeled "57" in FIG. 56.

FIG. 57 illustrates, by way of example, a partial cutaway diagram of a portion of the sheath system 5600 labeled "57" in FIG. 56. The migration mitigation component 5610 can include a lumen extending therethrough. An inner diameter 5618 of the migration mitigation component 5610, up to a frustoconical portion 5612, allows the outer diameter 5218 of the implantable device 110 to traverse therethrough. The frustoconical portion 5612 tapers both the outer diameter 5614 and the inner diameter 5618 of the migration mitigation component 5610 from larger to smaller. The larger diameter of the frustoconical portion 5612 is closer to the end of the shaft 5602 and the smaller diameter of the frustoconical portion 5612 is further from the end of the shaft 5602.

The shaft 5602 can include an end 5620 configured to mechanically couple with the migration mitigation component 5610. The end 5620 can include a stepped configuration or can be otherwise configured to receive a corresponding end 5622 of the migration mitigation component 5610 internal to the shaft 5602. Alternatively, the end 5620 can be tapered or otherwise configured to be inserted into the end 5622 of the migration mitigation component 5610.

Figure 58:
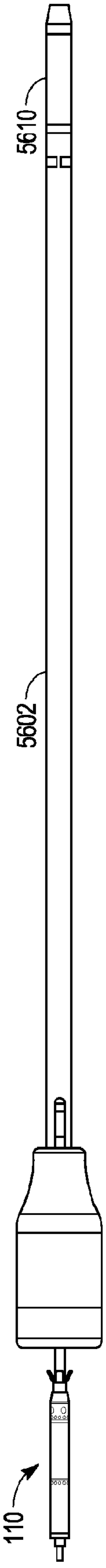
FIGS. 58, 59, and 60 illustrate, by way of example, respective diagrams of an embodiment of an implantable device being inserted into a lumen of a shaft at various stages.
Figure 59:
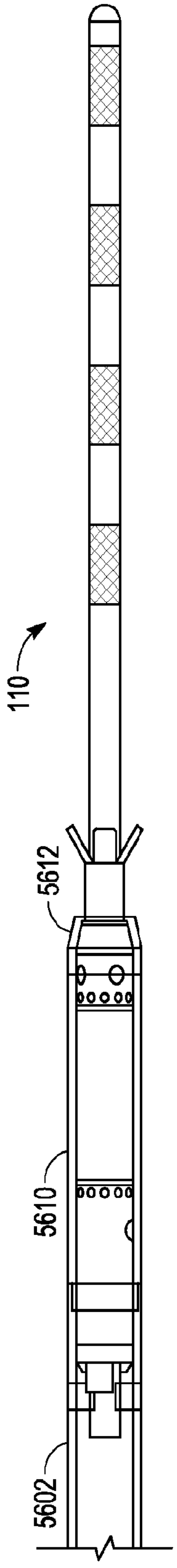
Figure 60:
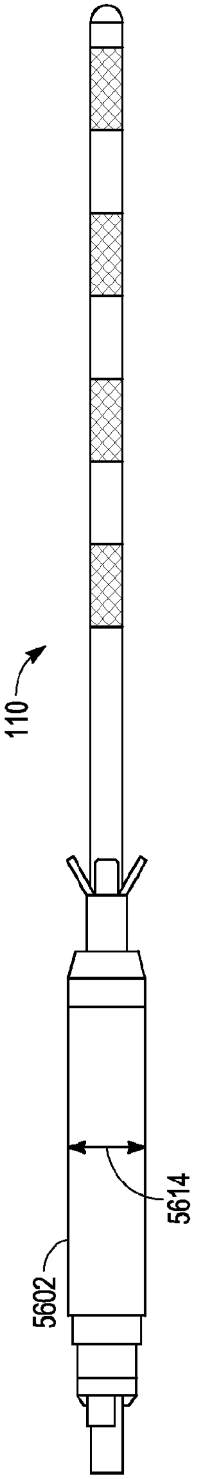

FIGS. 58, 59, and 60 illustrate, by way of example, respective diagrams showing insertion of the implantable device 110 into the lumen of the shaft 5602 at various stages. In FIG. 58, the implantable device 110 is inserted into a proximal side of the shaft 5602 and traverses towards the migration mitigation component 5610. In FIG. 59, the implantable device 110 has traversed the shaft 5602 such that electrodes of the implantable device 110 extend distally out of the migration mitigation component 5610. In the configuration in FIG. 59, a frustoconical connector 2320 of the implantable device 110 abuts against the frustoconical portion 5612 of the migration mitigation component 5610. The frustoconical connector 2320, when pushed against the frustoconical portion 5612, applies a force. When the applied force exceeds a strength of the mechanical coupling (e.g., exceeds a friction coefficient or overcomes another retention feature) between the shaft 5602 and the migration mitigation component 5610, then the migration mitigation component 5610 separates from the shaft 5602. In other words, according to an embodiment, the frustoconical portion 5612 can arrest travel of at least a portion of the implantable device 110 through the shaft 5602, such that continued application of force on the implantable device 110 (e.g., using a push rod) causes a corresponding force on the migration mitigation component 5610. When the force on the migration mitigation component 5610 exceeds a threshold force amount, the migration mitigation component 5610 can separate from a more proximal portion of the shaft 5602.

Figure 61:
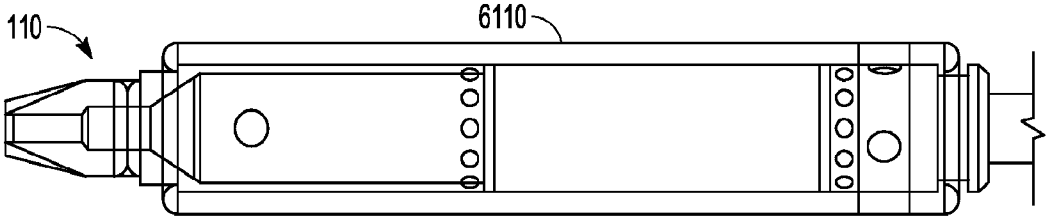
FIGS. 61, 62, and 63 illustrate, by way of example, respective diagrams of embodiments of systems that include a migration mitigation component.
Figure 62:
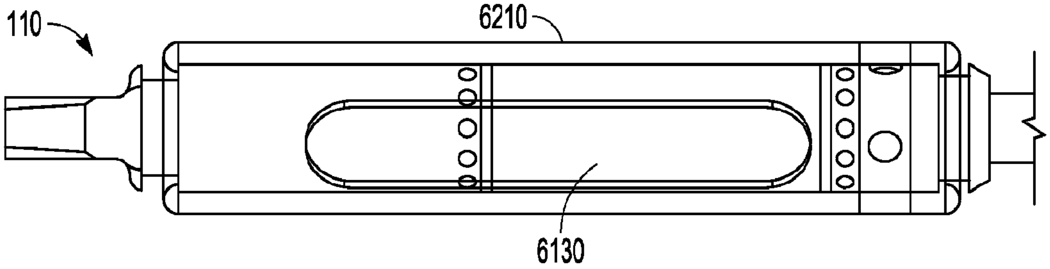
Figure 63:
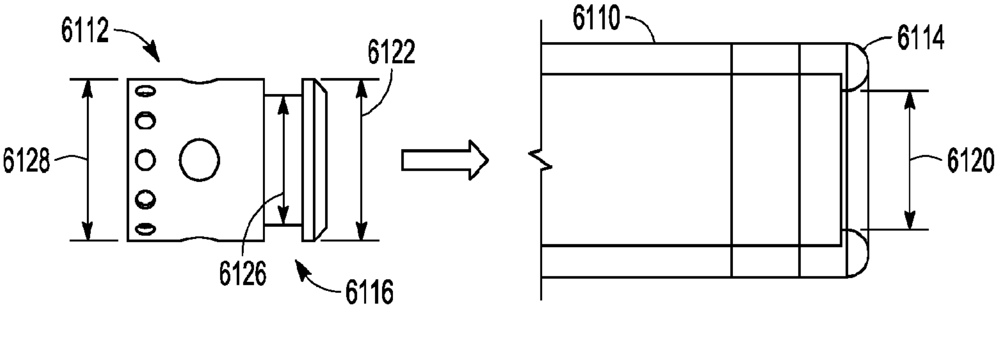

FIG. 60 illustrates the migration mitigation component 5610 separated from the shaft 5602 and situated about the implantable device 110. The implantable device 110 with the migration mitigation component 5610 situated therearound has a larger outer diameter 5614 than the implantable device 110 without the distal portion 5210 (the outer diameter 5218). This increased outer diameter 5614 helps retain the implantable device 110 in an implanted location and withstand migration. migration mitigation component FIGS. 61, 62, and 63 illustrate, by way of example, respective diagrams of embodiments of systems that include respective other examples of migration mitigation components 6110 and 6210. In the examples, the migration mitigation components 6110 and 6210 include various means for mechanically coupling with, receiving, or retaining the implantable device 110. For example, the implantable device 110 can include a connector component 6112 (see FIG. 63) that is configured to mechanically couple with the migration mitigation component 6110. In an example, the connector component 6112 comprises a portion of or can be used in place of the frustoconical connector described elsewhere herein. The connector component 6112 can include a circular groove 6116 or recessed portion. The groove 6116 can extend partially or completely around the connector component 6112. A portion 6114 of the migration mitigation component 6110 can include an overhang portion, such as with a reduced inner diameter 6120 relative to the rest of the migration mitigation component 6110. The groove 6116 can include a recess with an outer diameter 6126 that is less than the inner diameter 6120 of the portion 6114 of the migration mitigation component 6110. A first sidewall, such as adjacent to a first side of the groove 6116, can have an outer diameter 6122 that is larger than the outer diameter 6126. In an example, a second sidewall, such as adjacent to a proximal second side of the groove 6116, can have an outer diameter 6128 that is larger than the outer diameter 6122. This configuration with larger diameter sidewalls allows the portion 6114 to reside in, and can be retained by, the groove 6116. The inner diameter 6120 can be less than the outer diameter 6122 and the outer diameter 6128. Such a configuration can help retain the portion 6114 in the recess and thus retain the migration mitigation component 6210 about the implantable device 110. A similar grooved wheel configuration can be provided at a different location along the implant, such as to secure another end portion of the migration mitigation component 6110 and reduce further a potential of the migration mitigation component 6110 releasing or moving off of the implantable device 110.

The migration mitigation component 6210 can include a feature 6130 that helps the migration mitigation component 6210 mechanically couple with tissue of a patient in which the implantable device 110 is implanted. The feature 6130 is illustrated as a through-hole in the migration mitigation component 6210 but could additionally or alternatively include a surface finish, detent, protrusion, or the like.

FIGS. 64, 65, 66, 67, 68, 69, 70, 71, 72, and 73 illustrate, by way of example, various embodiments of migration mitigation components. The migration mitigation components can be provided integrally with a sheath or can be provided as respective discrete migration mitigation components that are couplable with or usable together with a sheath, or the like.

Figure 64:
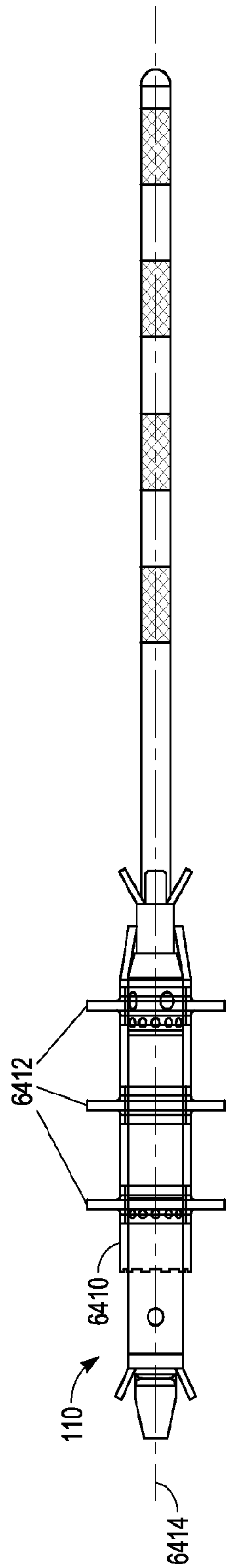
FIGS. 64, 65, 66, 67, 68, 69, 70, 71, 72, and 73 illustrate, by way of example, various respective embodiments of migration mitigation components.

FIG. 64 illustrates an implantable device 110 with a migration mitigation component 6410 that includes elliptical protrusions 6412 radiating outward from a longitudinal axis of the migration mitigation component. The longitudinal axis is indicated by dashed line 6414. The elliptical protrusions 6412 can be made of a semiflexible material. The elliptical protrusions 6412 can deform or collapse, such as to fit inside a lumen of a delivery tool. Then, when the elliptical protrusions 6412 are exposed or settle in an implanted position, they can extend to the form illustrated in FIG. 64 or a similar form.

Figure 65:
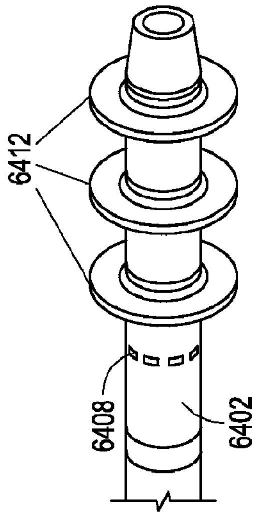
Figure 67:
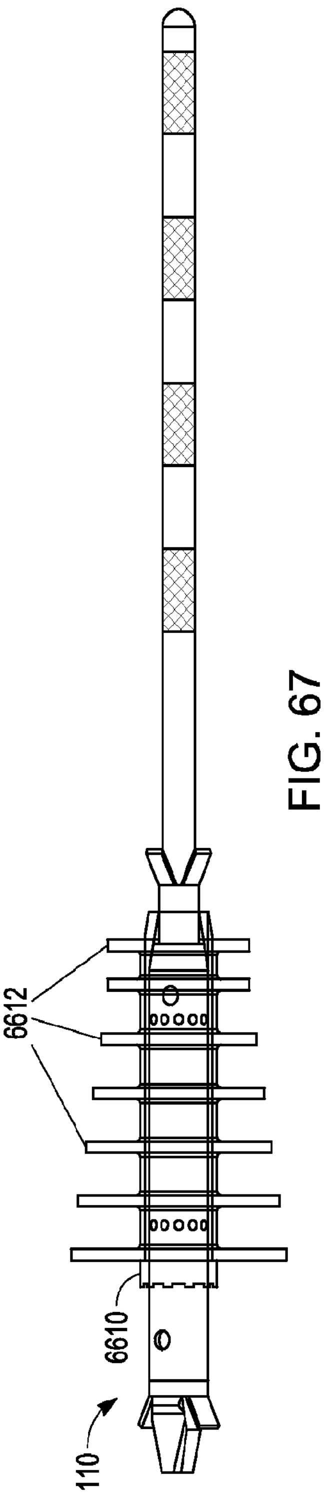

FIG. 65 illustrates the elliptical protrusions 6412 as part of a shaft 6402. The elliptical protrusions 6412 are more distal than a breakaway portion 6408 (similar to breakaway portion 5204), such that the elliptical protrusions 6412 remain situated about the implantable device 110 when force sufficient to break the breakaway portion 6404 from the shaft 6402 is applied. Alternative to the embodiment illustrated in FIG. 65, the elliptical protrusions 6412 can be situated about a discrete migration mitigation component. The elliptical protrusions illustrated in FIGS. 65 and 64 can have similar dimensions. The elliptical protrusions, or other features, on a migration mitigation component can be of same, similar, or different dimensions. FIG. 67, for example, illustrates a migration mitigation component 6610 with elliptical protrusions 6612 that have varying dimensions. The dimensions of the elliptical protrusions 6612 in FIG. 67 have incrementally increasing dimensions, such that a more proximal one of the elliptical protrusions 6612 is larger than a more distal one of the elliptical protrusions 6612.

Figure 66:
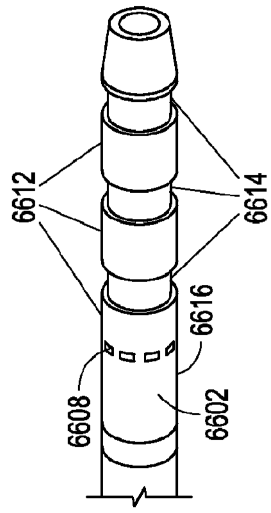

FIG. 66 illustrates an embodiment of a portion of a shaft 6602 that includes retention features more distal than a breakaway portion 6608. The retention features in FIG. 66 include one or more grooves or indents 6614 in an outer surface 6616 of the shaft 6602. The indents 6614 provide extra resistance to movement of the migration mitigation component.

Figure 68:
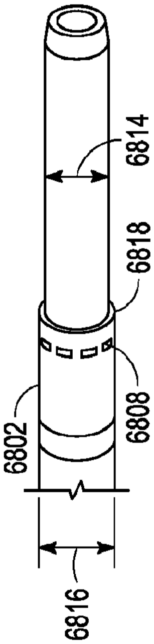
Figure 70:
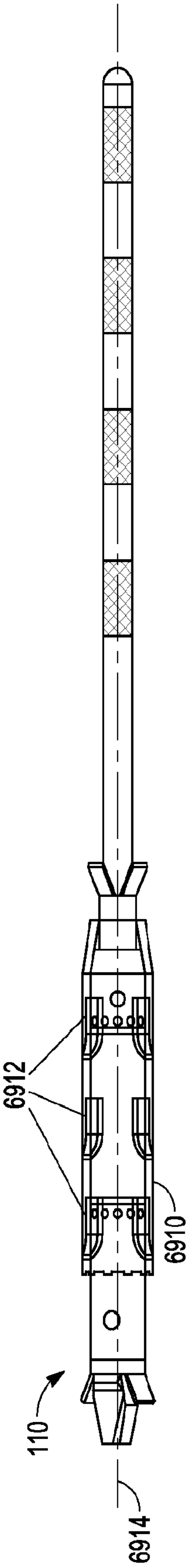

FIG. 68 illustrates an embodiment of a shaft 6802 that includes a retention feature more distal than a breakaway portion 6808. The retention feature in FIG. 68 includes a shaft with a reduced outer diameter 6814 more distal than the breakaway portion 6808. The reduced outer diameter 6814, along with the outer diameter 6816, forms a step feature 6818 that provides extra resistance to motion of the migration mitigation component illustrated in FIG. 68.

Figure 69:
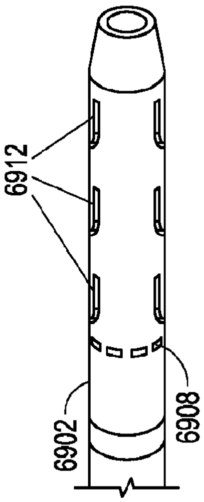

FIG. 69 illustrates an embodiment of a shaft 6902 that includes indent features 6912 situated more distal than a breakaway portion 6908. The indent features as illustrated, extend less than fully around a circumference of the shaft 6902. The indent features 6912 are further illustrated in FIG. 70 as part of a migration mitigation component 6910. The indent features 6912 each can extend towards a longitudinal axis (indicated by 6914) at a more distal portion of the indent feature 6912 and can extend away from the longitudinal axis at more proximal portion of the indent feature 6912. In an example, the indent features 6912 can include through-holes.

Figure 71:
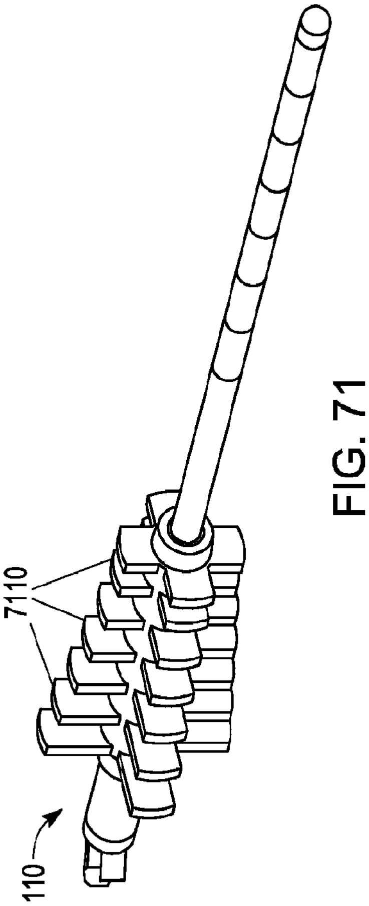

FIG. 71 illustrates a migration mitigation component with fan blade features 7110 extending therefrom. Many other shapes and sizes of features are within the scope of embodiments including other polygon shaped features, irregular shaped features, or the like.

Figure 72:
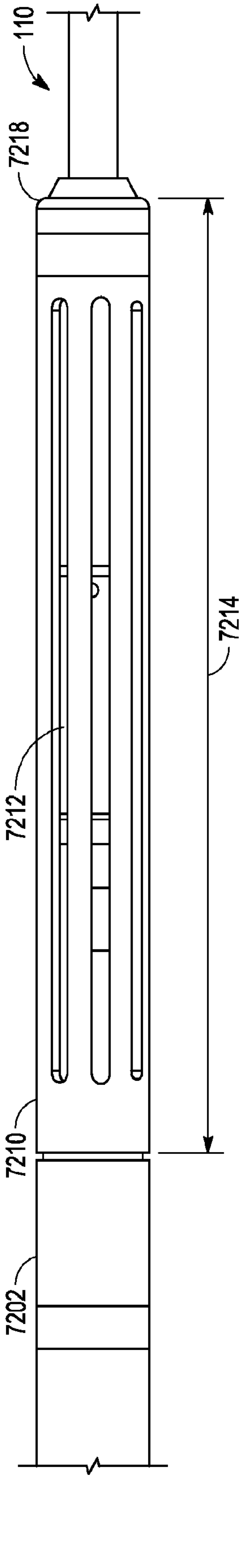
Figure 73:
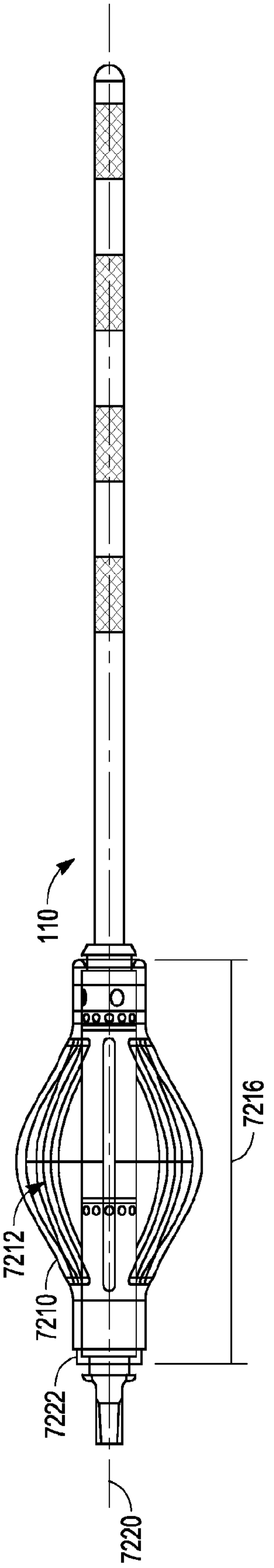

FIG. 72 illustrates an example of a migration mitigation component 7210 that is compressible. The migration mitigation components in FIGS. 52-71 generally include a fixed length (e.g., along the longitudinal axis of the migration mitigation components). The migration mitigation component 7210 can be compressed from a longitudinally expanded or an uncompressed length (indicated by arrow 7214) to a longitudinally contracted or lesser compressed length (indicated by arrow 7216 in FIG. 73). A shaft 7202 can be mechanically coupled to the migration mitigation component 7210. The shaft 7202 and the migration mitigation component 7210, when mechanically coupled, can be slid over a guidewire to an implant location. The implantable device 110 can be moved through a lumen of the shaft 7202 and a lumen of the migration mitigation component 7210 until a first end 7218 of the migration mitigation component 7210 mechanically couples with the implantable device 110. Then the shaft 7202 can be pushed (e.g., while the implantable device 110 is held in place, such as by another guidewire or the like) against the implantable device 110 to compress features 7212 of the migration mitigation component 7210. The compression can be performed until a proximal end 7222 of the migration mitigation component 7210 is mechanically coupled with the implantable device 110. The features 7212 can buckle outwards, away from the longitudinal axis indicated by dashed line 7220, and engage tissue about the feature 7212, thus improving a resistance of the implantable device 110 from migration.

FIGS. 74, 75, 76, 77, 78, and 79 generally discuss techniques for affixing the migration mitigation component of a sheath to an implantable device 110 after the implantable device 110 is implanted but before a guidewire is removed from the implantable device 110.

Figure 74:
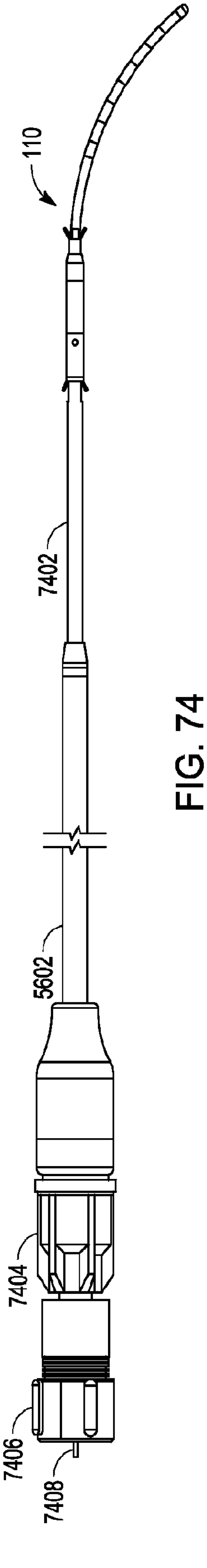
FIGS. 74, 75, 76, 77, 78, and 79 illustrate, by way of example, diagrams of portions of a technique for situating a migration mitigation component about an implantable device after device implantation.

FIGS. 74, 75, 76, 77, 78, and 79 illustrate, by way of example, diagrams of portions of a technique for situating a migration mitigation component 7410 about the implantable device 110 after implantation. FIG. 74 shows the implantable device 110 coupled to a guidewire 7408. A push rod 7402 is mechanically coupled with a proximal end of the implantable device 110. The push rod 7402 includes an outer diameter that is less than a diameter of the lumen of the sheath shaft 5602. The push rod 7402 includes a lumen through which the guidewire 7408 can travel. The push rod 7402 can be inserted into the lumen of the shaft 5602, such as after the implantable device 110 is situated in the lumen of the shaft 5602.

The push rod 7402 can include a luer cap 7406, an attachable and detachable threaded cap 7404, or a combination thereof. The cap 7404 can be situated more distal than the luer cap 7406. The luer cap 7406 can be tightened with a portion of the guidewire 7408 therein, such as to help ensure the guidewire 7408 remains accessible external to a patient during an implant procedure.

Figure 75:
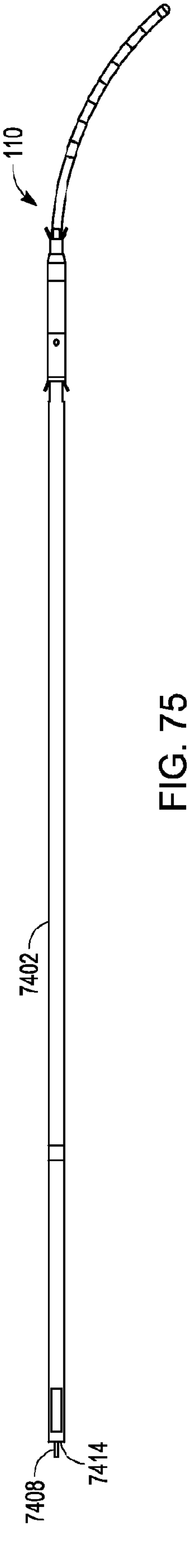

The implantable device 110 can be implanted into position. Then the cap 7404 can be removed from the push rod 7402. FIG. 75 illustrates the push rod 7402 mechanically coupled with the implantable device 110 after the cap 7404 (and the luer cap 7406) are removed. The guidewire 7408 can remain coupled to the luer cap 7406 even if the luer cap 7406 is no longer on the push rod 7402.

Figure 76:
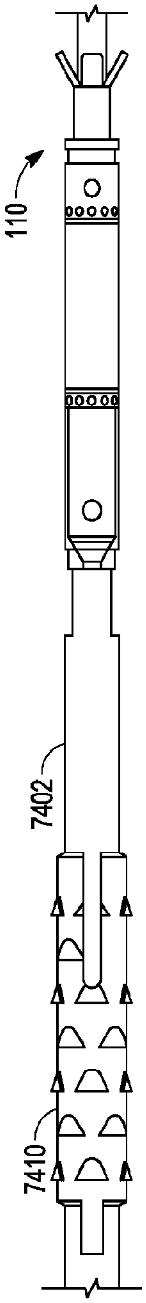
Figure 77:
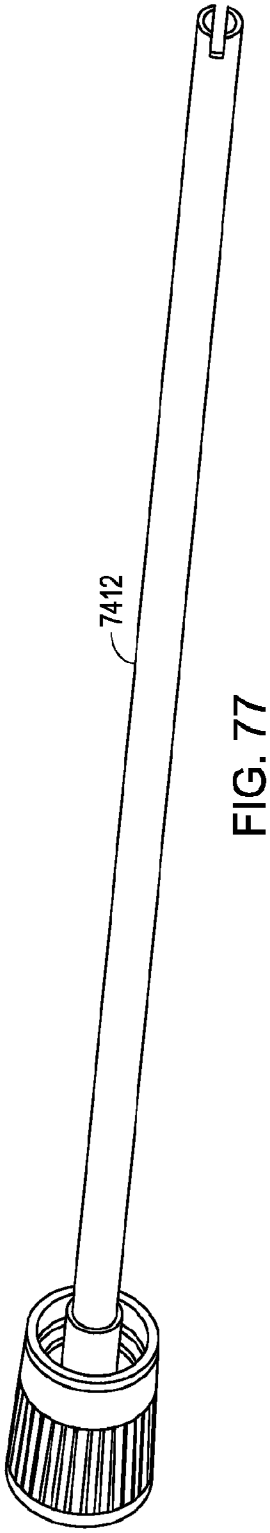

A migration mitigation component 7410 can be slid over the guidewire 7408 and the push rod 7402, such as while the push rod 7402 remains mechanically coupled with the implantable device 110. FIG. 76 illustrates the migration mitigation component 7410 over the push rod 7402 and guidewire 7408 traversing towards the implantable device 110. The migration mitigation component 7410 can be slid over the push rod 7402 towards the implantable device 110, for example, using another push rod 7412. FIG. 77 illustrates the push rod 7412. The push rod 7412 can include a shaft that includes a control knob or other graspable component on a proximal end. The shaft of the push rod 7412 can include an interface on a distal end thereof that is configured to mate with the migration mitigation component 7410. The inner diameter and outer diameter of the push rod 7412 can be about the same as the inner diameter and outer diameter of a lumen of the sheath shaft 5602.

Figure 78:
Figure 79:
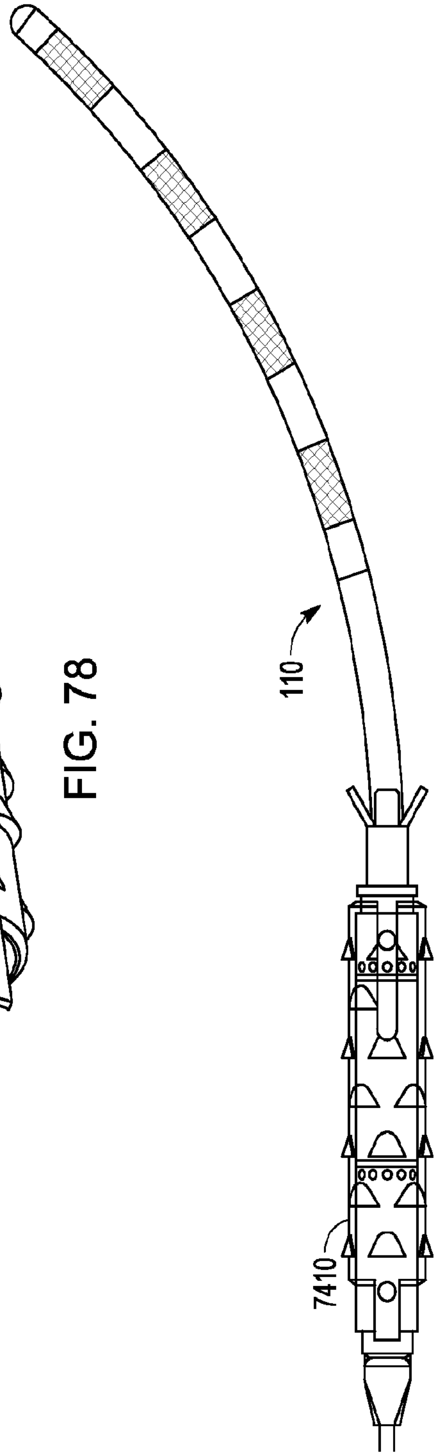

An example of the migration mitigation component 7410 is illustrated in FIG. 78. The migration mitigation component 7410 includes a surface texture configured to help reduce a likelihood that the migration mitigation component migrates after implantation. The migration mitigation component 7410 can include a lip, edge, or other feature that is configured to mate with a corresponding grooved portion or other structure of the implantable device 110. Such a feature allows the migration mitigation component to mechanically couple with the implantable device 110. FIG. 79 illustrates the migration mitigation component 7410 mechanically coupled with the implantable device 110 and mated with grooved portions therein In an example, a migration mitigation component deployment technique can include situating a migration mitigation component proximate the implant site and then implanting an implantable device through the migration mitigation component and then coupling the migration mitigation component with the implantable device 110.

FIGS. 80, 81, 82, 83, 84, 85, 86, 87, and 88 illustrate, by way of example, respective diagrams of an embodiment of a technique for providing a fixation mechanism through which the implantable device 110 can be implanted. The technique of FIGS. 80, 81, 82, 83, 84, 85, 86, 87, and 88 includes implanting a migration mitigation component first, and then implanting the implantable device 110 through the migration mitigation component.

Figure 80:
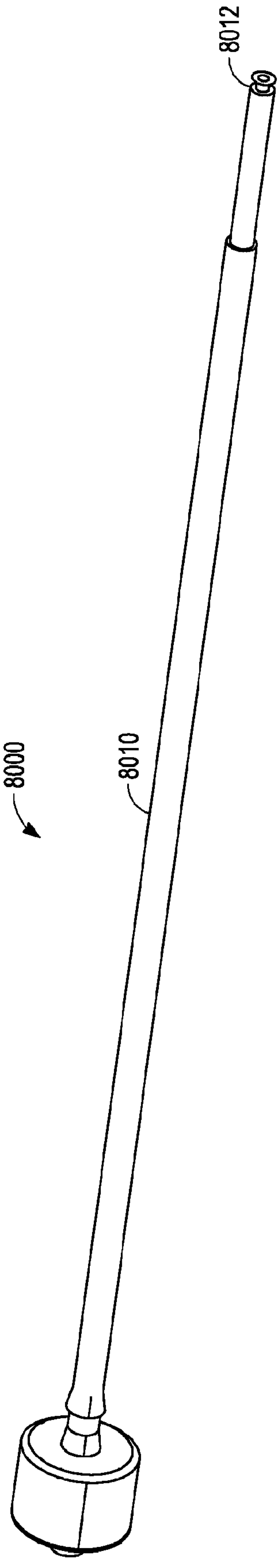
FIGS. 80, 81, 82, 83, 84, 85, 86, 87, and 88 illustrate, by way of example, respective diagrams of an embodiment of a technique for providing a fixation mechanism through which the implantable device can be implanted.

FIG. 80 illustrates a perspective view diagram of an embodiment of a fixation deployment tool 8000. The fixation deployment tool 8000 includes a shaft 8010 with a lumen that can slide over a guidewire. A shaft 8010 of the fixation deployment tool 8000 can be inserted into a lumen of a fixation deployment cover 8100 (see FIG. 81). The shaft 8010 can include a stepped diameter such that a more distal portion of the shaft 8010 has a smaller diameter than a more proximal portion of the shaft 8010. Such a shaft configuration can allow a migration mitigation component to be situated over the proximal end 8012 of the shaft 8010.

Figure 81:
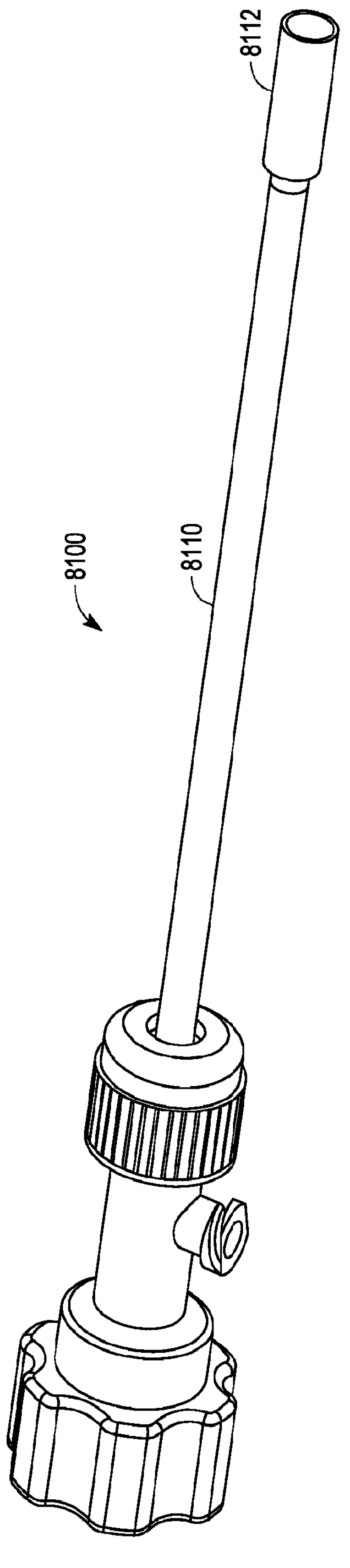

FIG. 81 illustrates a perspective view diagram of an embodiment of a fixation component cover 8100. A migration mitigation component can be situated in a cover 8112 situated on a distal end of a shaft 8110 of the fixation component cover 8100. The fixation component cover 8100 can include a lumen extending therethrough that allows the shaft 8010 of the fixation deployment tool 8000 to traverse therethrough. An inner diameter of the cover 8112 can be larger than an inner diameter of the remainder of the shaft 8110. The inner diameter of the cover 8112 can be larger than an outer diameter of the migration mitigation component.

Figure 82:
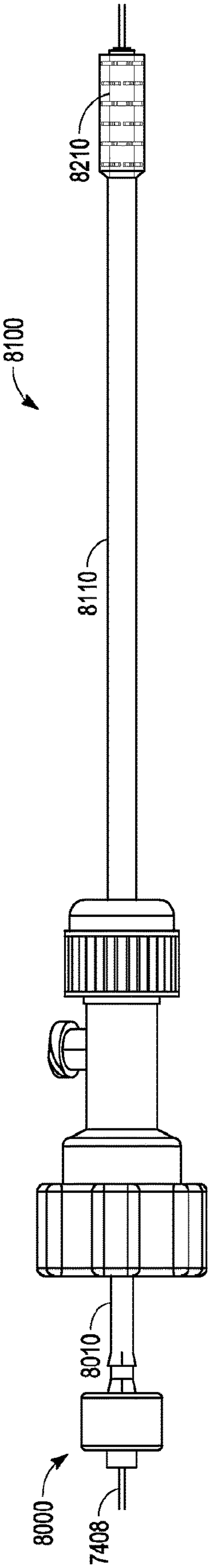

A guidewire 7408 can be situated in a patient. A migration mitigation component 8210 (see FIG. 82) can be situated in the cover 8112 of the fixation deployment cover 8100. Then the fixation deployment cover 8112 can be traversed along the guidewire 7408 to situate the migration mitigation component 8210 near an implant location. The shaft 8010 of the fixation deployment tool 8000 can then be traversed through the lumen of the fixation deployment cover 8112. FIG. 82 illustrates the fixation deployment tool 8000, the fixation deployment cover 8100, and the migration mitigation component 8210 in this configuration.

Figure 83:
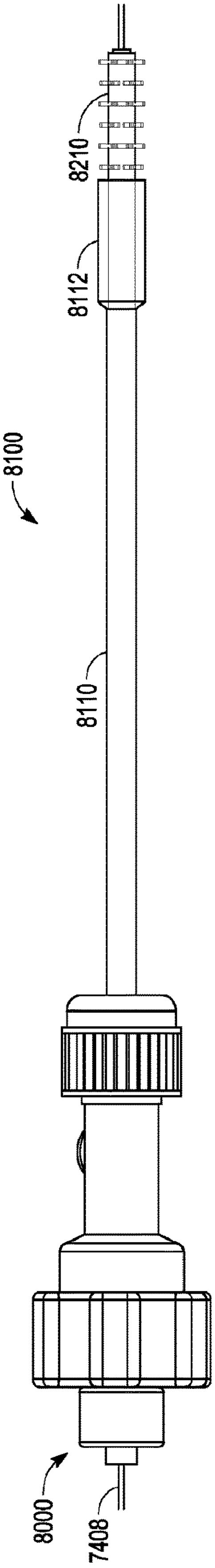
Figure 84:
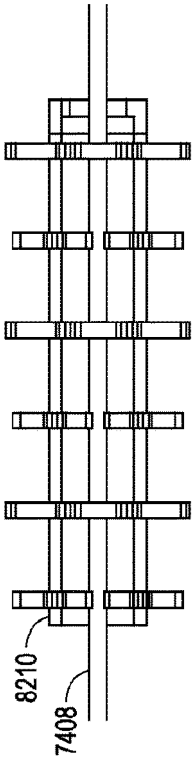

FIG. 83 illustrates the fixation deployment tool 8000 pushing the migration mitigation component 8210 out of the cover 8112 of the fixation deployment cover 8100 or of withdrawing the fixation deployment tool 8000 away from the migration mitigation component 8210 in a proximal direction. Then, the fixation deployment cover 8100 and the fixation deployment tool 8000 can be removed, leaving the migration mitigation component 8210 implanted and still situated about the guidewire 7408 as illustrated in FIG. 84.

Figure 85:
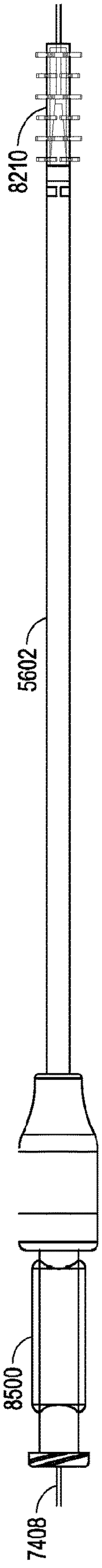
Figure 86:
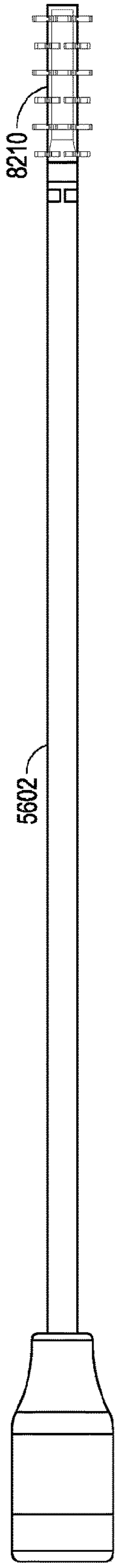
Figure 87:
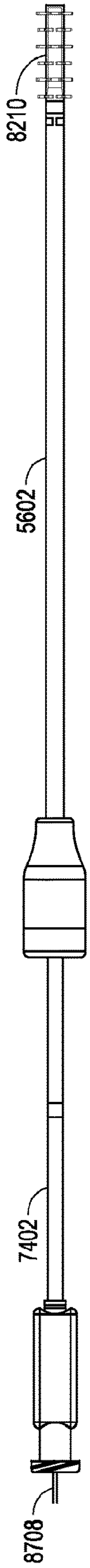

After the migration mitigation component 8210 is properly situated, the sheath shaft 5602 and a dilator 8500 can be traversed along the guidewire 7408 to the migration mitigation component 8210. FIG. 85 illustrates the sheath shaft 5602 and dilator 8500 proximate the migration mitigation component 8210. FIG. 86 illustrates the dilator 8500 and the guidewire 7408 removed from the sheath shaft 5602, leaving the sheath shaft 5602 proximate the migration mitigation component 8210.

Figure 88:
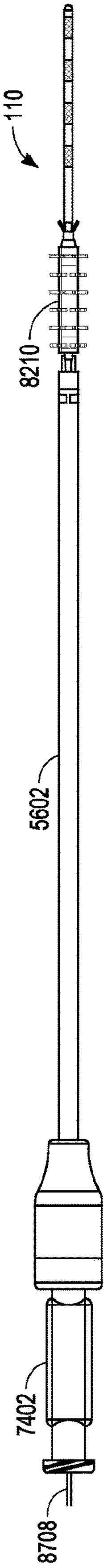

The implantable device 110 (e.g., with a retraction wire 8708 attached to a proximal end thereof) can be situated in the sheath shaft 5602. The push rod 7402 can then be situated to push the implantable device 110 through the sheath shaft 5602, into the migration mitigation component 8210, and at least partially through the migration mitigation component 8210, as illustrated in FIG. 88 wherein the implantable device 110 itself is obscured by the outer surfaces of the shaft 5602 and the migration mitigation component 8210. The implantable device 110 can be pushed further along the guidewire so that electrodes of the implantable device 110 are exposed distal to the migration mitigation component 8210 as illustrated in FIG. 88. The push rod 7402 and the sheath shaft 5602 can be removed leaving the implantable device 110 situated within and mechanically coupled to the migration mitigation component 8210. This technique allows the migration mitigation component 8210 to be inserted before implant of the implantable device 110.

FIGS. 89, 90, 91, 92, 93, 94, 95, 96, 97, and 98 illustrate, by way of example, respective embodiments of fixation mechanisms that can be deployed on or from the implantable device 110.

Figure 89:
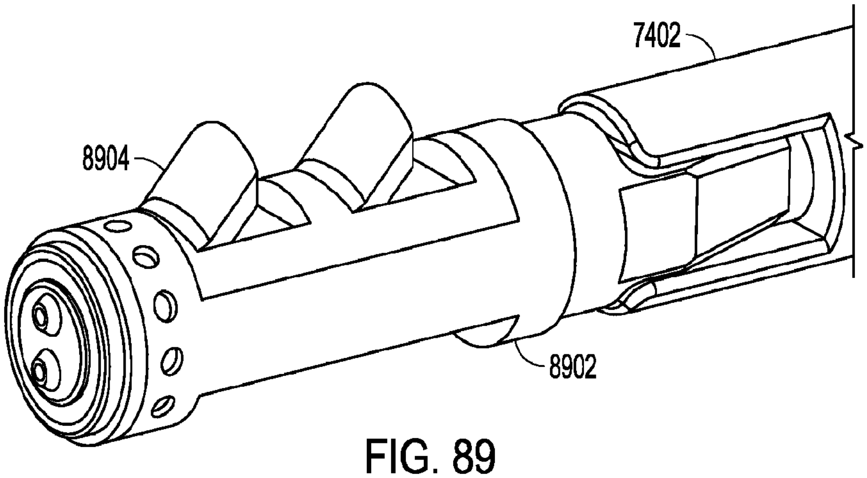
FIGS. 89 and 90, illustrate, by way of example, respective embodiments of deployable fixation mechanisms for an implantable device.
Figure 90:
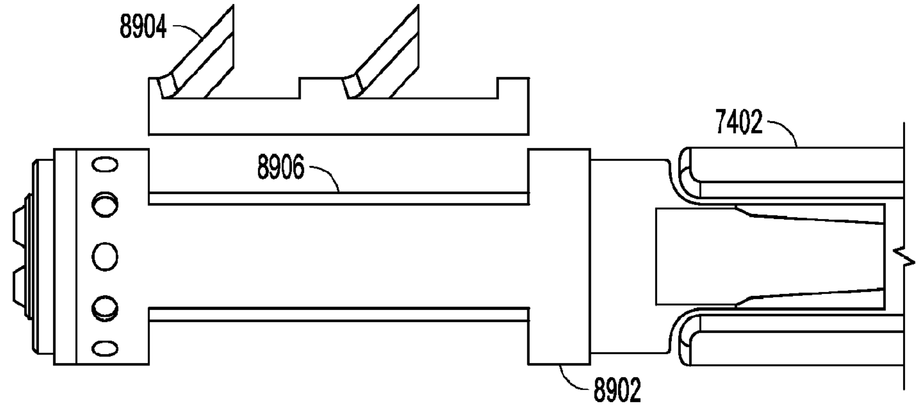

FIG. 89 illustrates a fixation mechanism in the form of removable tines 8904. The removable tines 8904 provide a protrusion that extends along and outward from a longitudinal axis of the implantable device 110. The removable tines 8904 can mate with a corresponding feature 8906 (see FIG. 90) or tine receptacle in an antenna housing 8902 of the implantable device 110. The mating between the feature 8906 and the removable tines 8904 can include a form fit, a detent and a mating protrusion, a compression fit, or other mechanical coupling, such as with or without an adhesive. FIG. 90 illustrates the removable tines 8904 disconnected from the feature 8906.

Figure 91:
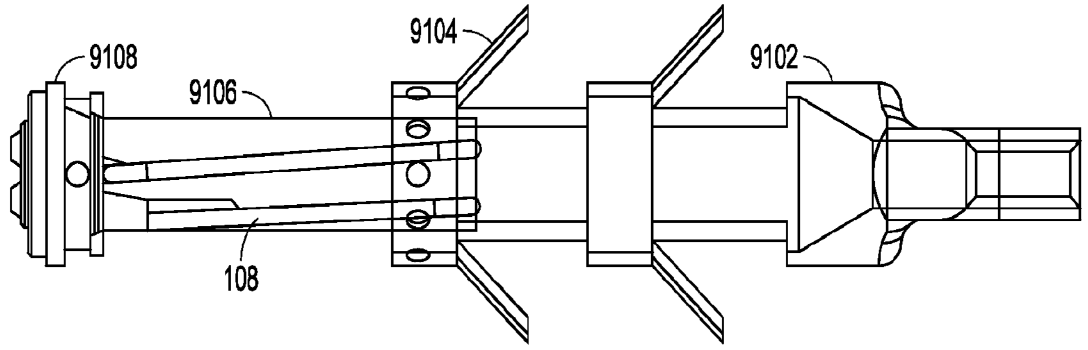
FIG. 91 illustrates an antenna housing that includes tines.

FIG. 91 illustrates an antenna housing 9102 that includes tines 9104 (similar to the removable tines 8904) integrally formed therewith. The antenna housing 9102 can be radiotransparent at the frequency (or multiple frequencies) at which the antenna 108) operates. The antenna housing 9102 can be mechanically coupled with an end cap 9108 to retain the antenna housing 9102 to the implantable device. The mechanical coupling between the antenna housing 9102 and the end cap 9108 can include a flange and groove coupling, a detent and indent coupling, a form fit, a compression fit, or the like. The end cap 9108 can help form a hermetic seal to a circuitry housing (e.g., see FIG. 92) to help protect circuitry of the implantable device 110 within the circuitry housing. The antenna 108 can be wound about a radiotransparent support 9106, such as to help the antenna 108 retain its form and operating characteristics.

Figure 92:
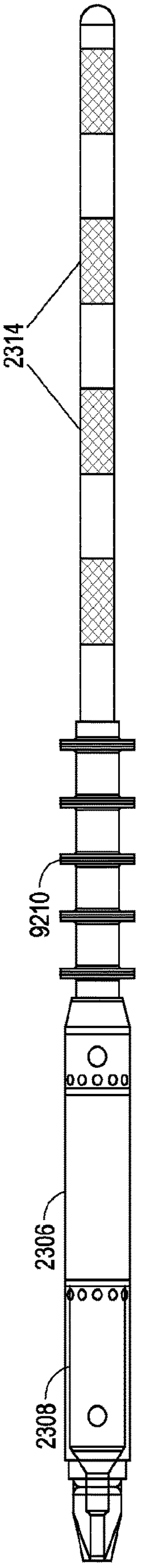
FIGS. 92, 93, and 94 illustrate different fixation components, respectively.
Figure 93:
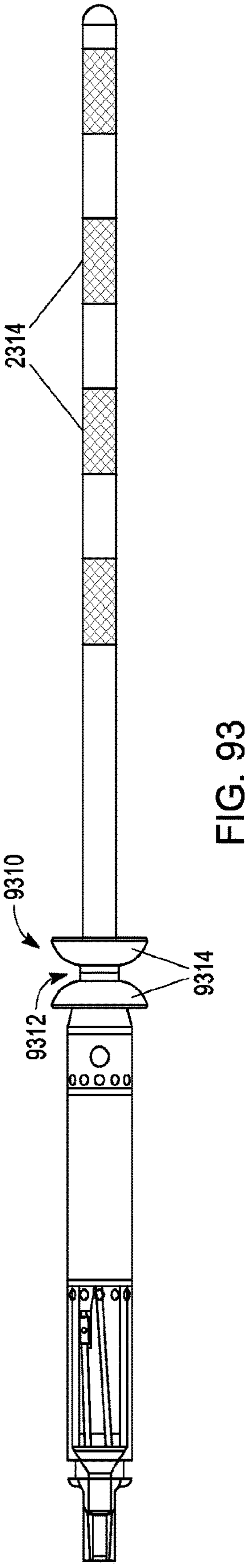
Figure 94:
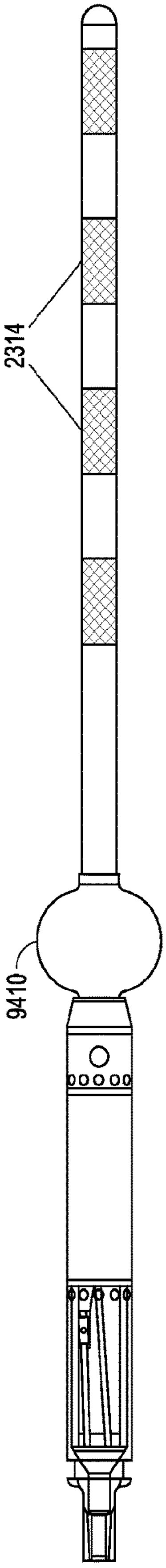

FIGS. 92, 93, and 94 illustrate different fixation components 9210, 9310, and 9410, respectively. The fixation components 9210, 9310, and 9410 are illustrated as being situated between electrodes 2314 and a circuitry housing 2306 of the implantable device 110. The circuitry housing 2306 is illustrated as being situated between the fixation components 9210, 9310, or 9410 and the antenna housing 2308.

The fixation component 9210 of FIG. 92 is similar to the migration mitigation component illustrated in FIGS. 64 and 65, with the fixation component 9210 being onboard the implantable device 110. The fixation component 9310 of FIG. 93 has a groove configuration that can allow tissue to propagate into a groove 9312 and along sidewalls 9314 thereof. FIG. 94 shows a fixation component 9410 in the form of a balloon. The balloon can be formed of an expandable and collapsible material, such as a thermoplastic or other polymer. The fixation component 9410 can be inserted into the patient in an uninflated configuration. Then, after the implantable device 110 is situated in an implanted position, the fixation component 9410 can be inflated to enhance fixation with the surrounding tissue.

Figure 95:
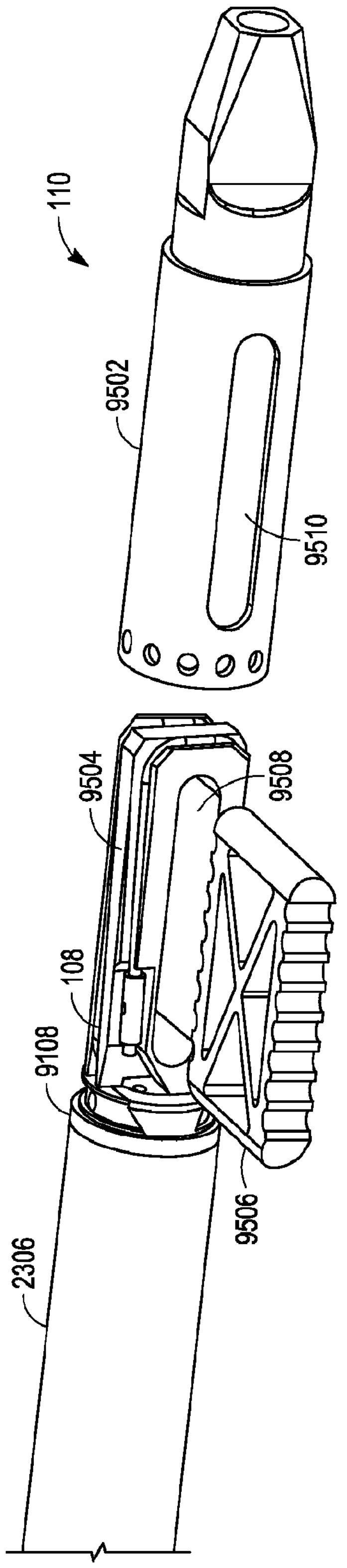
FIGS. 95, 96, and 97 illustrate portions of a technique for inserting a fixation component through an antenna support.
Figure 96:
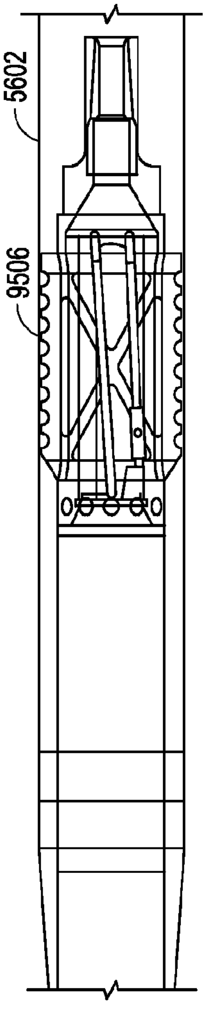
Figure 97:
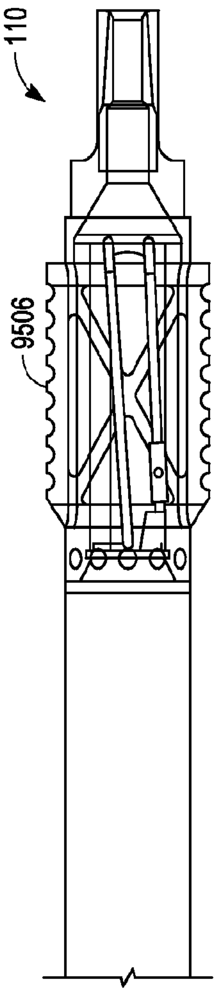

FIGS. 95, 96, and 97 illustrate portions of system that includes a fixation component 9506 inserted through an antenna support 9504. The antenna 108 can be wound about (e.g., through one revolution, or more or fewer) the antenna support 9504. The antenna support 9504 can include a hole or slot 9508 formed therethrough. The fixation component 9506 can be formed of a compressible or otherwise deformable material. The fixation component 9506 can be situated in the slot 9508. A portion of the fixation component 9506 can reside external to side edges of the slot 9508 when the fixation component 9506 is in uncompressed form. The antenna housing 9502 can be slid over the antenna 108 and the antenna support 9504, such as to mechanically couple with the end cap 9108, the antenna support 9504, or a combination thereof. A slot 9510 can be formed through the antenna housing 9502. The slot 9510 can allow the fixation component 9506 to extend beyond an outer surface of the antenna housing 9502. The fixation component 9506 can be compressed when it is in the slot 9508 while the antenna housing 9502 is slid over the antenna support 9504. Then, the fixation component 9506 can expand to extend through the slot 9510.

After the antenna housing 9502 is mechanically coupled to the antenna support 9504, the end cap 9108, or a combination thereof, and the fixation component 9506 extends through the slot 9510, and the implantable device 110 can be inserted into the sheath shaft 5602. Inserting the implantable device of FIG. 95 can compress the fixation component 9506 such that it can fit into the lumen of the sheath shaft 5602. Then, when the sheath shaft 5602 is pulled back or the fixation component 9506 is otherwise exposed internal to the patient, the fixation component 9506 can expand and at least a portion of the fixation component 9506 can extend out of the slot 9510 in the antenna housing 9502. FIG. 96 illustrates the compression of the fixation component 9506 inside the sheath shaft 5602. FIG. 97 illustrates the implantable device 110 of FIG. 96 after the fixation component 9506 is exposed.

Figure 98:
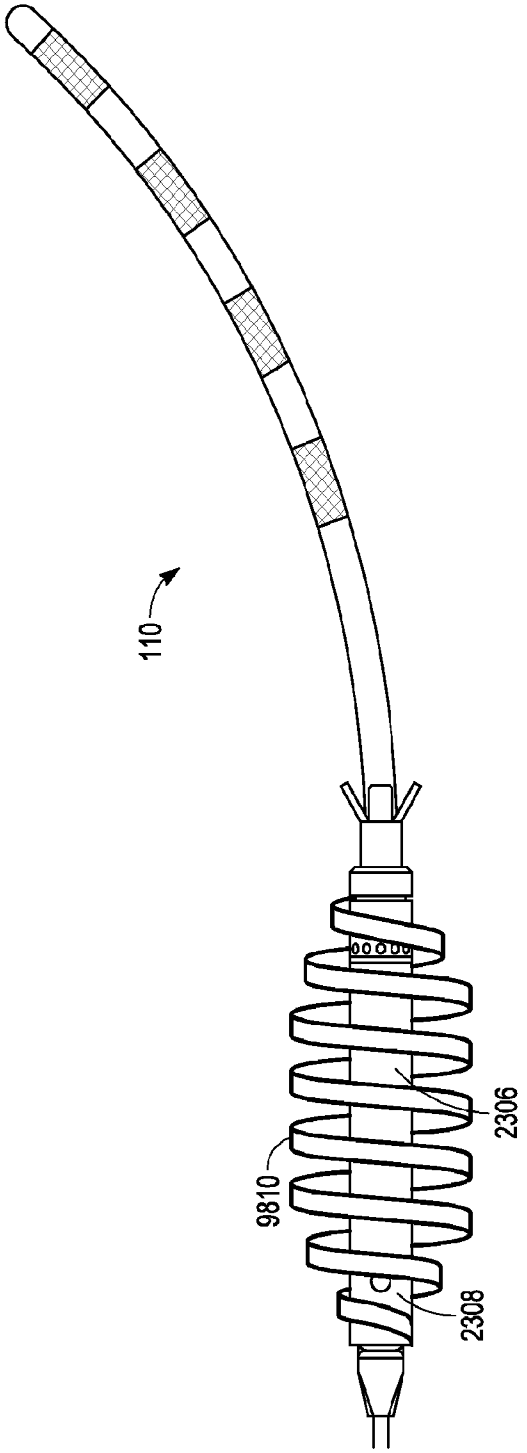
FIG. 98 illustrates an embodiment of a fixation component in the form of an expandable spring.

FIG. 98 illustrates an embodiment of a fixation component 9810 in the form of a coil, such as can include an expandable or contractable spring. The fixation component 9810 can be formed of a shape memory material, such as nitinol or the like. The fixation component 9810 can have shape memory for the shape illustrated. The fixation component 9810 can be wound about the circuitry housing 2306, antenna housing 2308, or a combination thereof. The fixation component 9810 can be wound such that it can fit into the lumen of the sheath shaft 5602. The implantable device 110 can then be implanted. Then, when the sheath shaft 5602 is removed or the fixation component 9810 is otherwise exposed, the fixation component 9810 can unwind to the position illustrated in FIG. 98. The fixation component 9810 can help restrict movement of the implantable device 110.

Sleep Apnea

Figure 99:
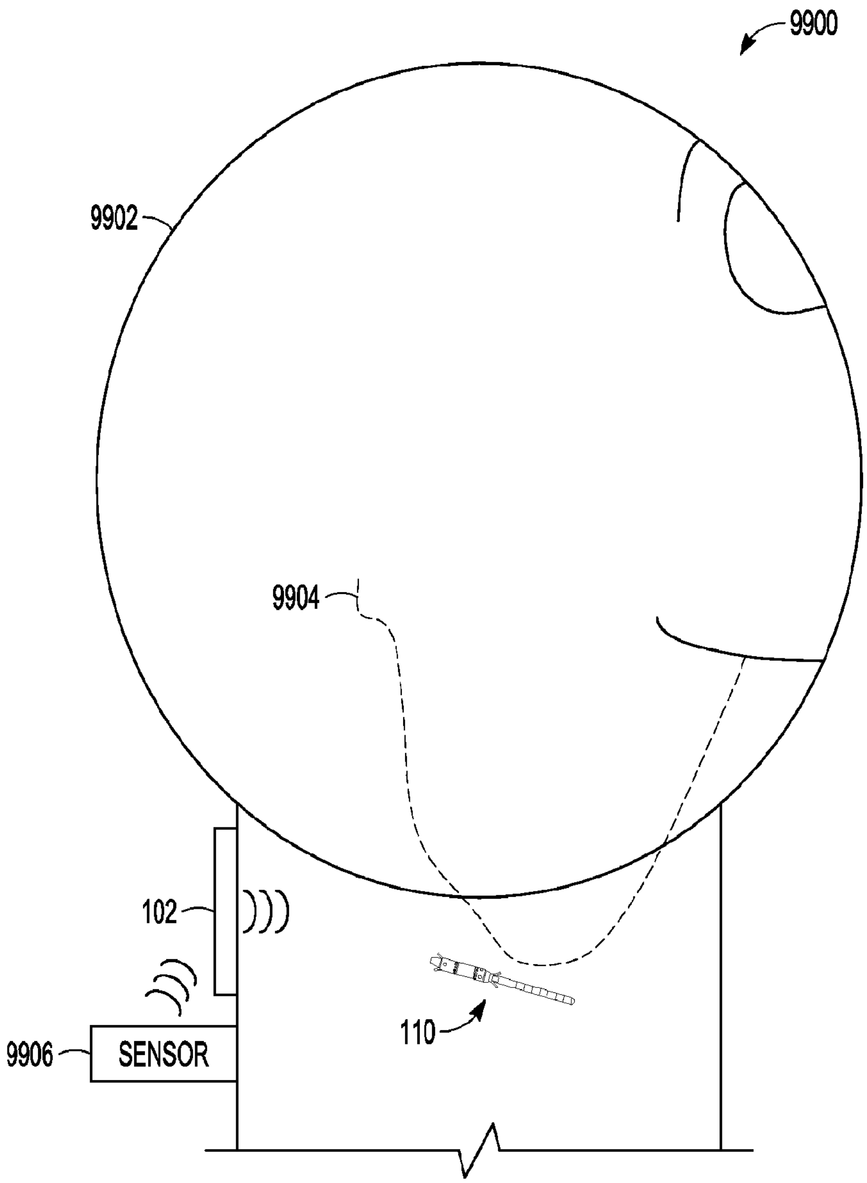
FIG. 99 illustrates, by way of example, a diagram of an embodiment of a system for sleep apnea management.

FIG. 99 illustrates, by way of example, a diagram of an embodiment of a system 9900 for sleep apnea management. The system 9900 as illustrated includes a patient 9902 with the implantable device 110 implanted proximate their hypoglossal nerve 9904. The implantable device 110 can be situated internal to the patient 9902, such as through an incision in an area around where the neck of the patient 9902 meets the chin of the patient 9902. This area is sometimes called the "jowls". The system 9900 further includes the external power source 102 wirelessly coupled with the implantable device 110. The system 9900 further includes a sensor 9906 communicatively coupled (e.g., wired or wirelessly coupled) with the external power source 102.

The sensor 9906 can monitor one or more apnea indicators such as blood-oxygen, noise (e.g., snoring detection), accelerometer, or the like. For example, noise above a specified threshold decibel level can indicate that the patient 9902 is having trouble breathing. In another example, a blood oxygen level at or below a specified threshold level can indicate that the patient 9902 is having trouble breathing. A microphone or accelerometer can be used to determine when normal respiration has stopped. The sensor 9906 can provide data indicative of the apnea indicator to the external power source 102.

The external power source 102 or another device that receives the data from the sensor 9906 can determine, based on the received data, whether an apnea event (e.g., trouble breathing) is being experienced by the patient 9902. The external power source 102, responsive to determining that an apnea event is being experienced based on the data from the sensor 9906, can provide electrical power to the implantable device 110. The implantable device 110 can receive the electrical power wirelessly from the external power source 102. The implantable device 110 can provide electrical stimulation to the hypoglossal nerve 9904. The hypoglossal nerve 9904, responsive to the electrical stimulation, can cause a muscle of the tongue to contract and move the tongue away from blocking airflow to the lungs. The tongue reflex responsive to the electrical stimulation can additionally or alternatively move the epiglottis or other structure so the epiglottis is not blocking airflow to the lungs.

Embodiments of Computer Hardware and/or Architecture

Figure 100:
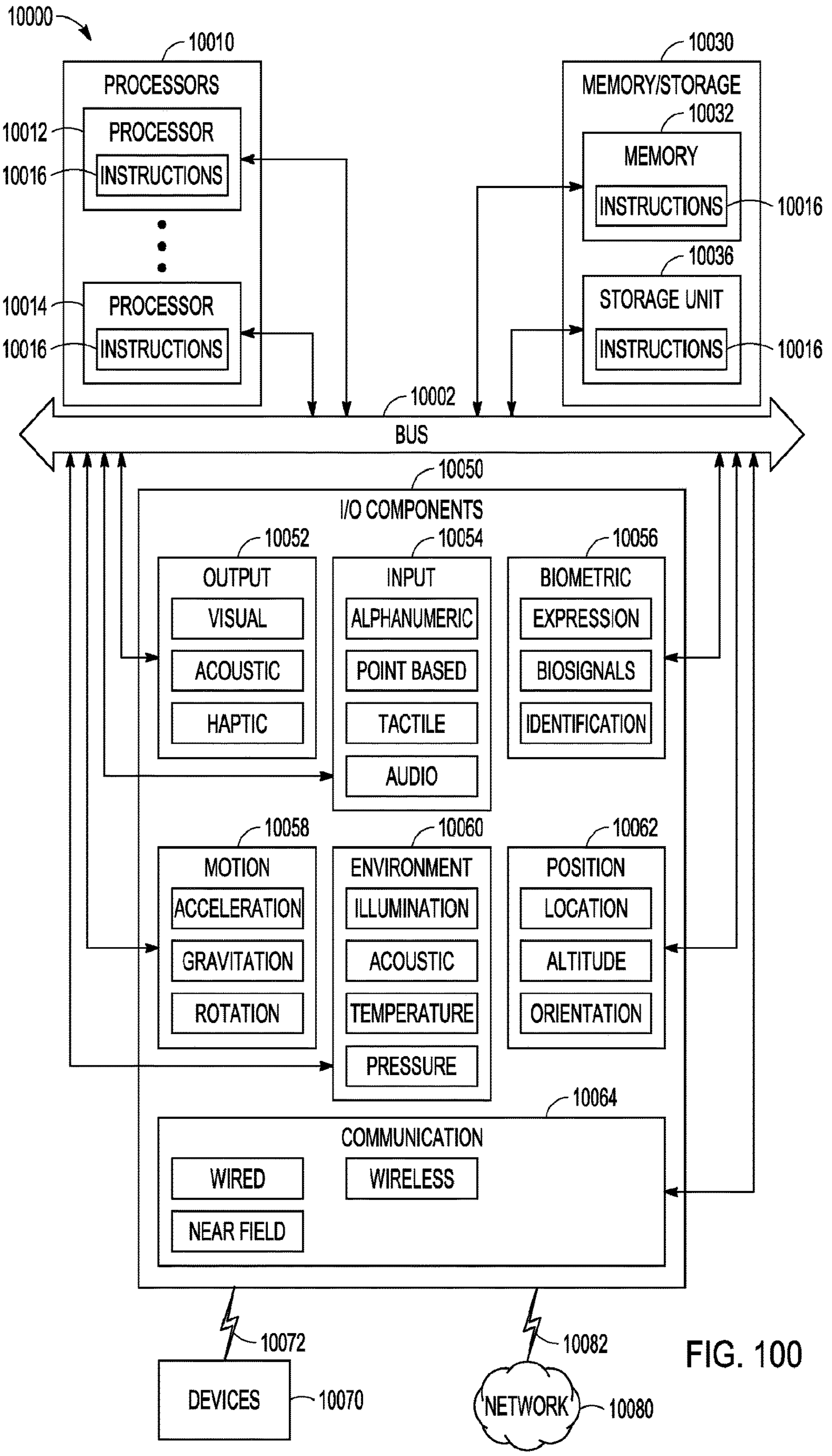
FIG. 100 illustrates, by way of example, a block diagram of an embodiment of a machine upon which one or more methods discussed herein can be performed or in conjunction with one or more systems or devices described herein may be used.

FIG. 100 illustrates, by way of example, a block diagram of an embodiment of a machine 10000 upon which one or more methods discussed herein can be performed or in conjunction with one or more systems or devices described herein may be used. FIG. 100 includes reference to structural components that are discussed and described in connection with several of the embodiments and figures above. In one or more embodiments, the implantable device 110, the source 102, the sensor 107, or other circuitry, such as location circuitry 3646, control circuitry 3752, transceiver 3644, can include one or more of the items of the machine 10000. The machine 10000, according to some example embodiments, is able to read instructions from a machine-readable medium (e.g., a machine-readable storage medium) and to perform any one or more of the methodologies, one or more operations of the methodologies, or one or more circuitry functions discussed herein, such as the methods described with regard to the FIGS. described herein. For example, FIG. 100 shows a diagrammatic representation of the machine 10000 in the example form of a computer system, within which instructions 10016 (e.g., software, a program, an application, an applet, an app, or other executable code) for causing the machine 10000 to perform any one or more of the methodologies discussed herein can be executed. The instructions transform the general, non-programmed machine into a particular machine programmed to carry out the described and illustrated functions in the manner described. In alternative embodiments, the machine 10000 operates as a standalone device or can be coupled (e.g., networked) to other machines. In a networked deployment, the machine 10000 can operate in the capacity of a server machine or a client machine in a server-client network environment, or as a peer machine in a peer-to-peer (or distributed) network environment. Various portions of the machine 10000 can be included in, or used with, one or more of the external source 102 and the implantable device 110. In one or more embodiments, different instantiations, or different physical hardware portions of the machine 10000 are separately implanted at the external source 102 and the implantable device 110.

In one or more embodiments, the machine 10000 can comprise, but is not limited to, a server computer, a client computer, a personal computer (PC), a tablet computer, a laptop computer, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 10016, sequentially or otherwise, that specify actions to be taken by machine 10000. Further, while only a single machine 10000 is illustrated, the term "machine" shall also be taken to include a collection of machines 10000 that individually or jointly execute the instructions 10016 to perform any one or more of the methodologies discussed herein.

The machine 10000 can include processors 10010, memory 10030, or I/O components 10050, which can be configured to communicate with each other such as via a bus 10002. In one or more embodiments embodiment, the processors 10010 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuitry (ASIC), a Radio-Frequency Integrated Circuitry (RFIC), another processor, or any suitable combination thereof) can include, for example, processor 10012 and processor 10014 that can execute instructions 10016. The term "processor" is intended to include multi-core processors that can include two or more independent processors (sometimes referred to as "cores") that can execute instructions contemporaneously. Although FIG. 100 shows multiple processors, the machine 10000 can include a single processor with a single core, a single processor with multiple cores (e.g., a multi-core process), multiple processors with a single core, multiple processors with multiples cores, or any combination thereof.

The memory/storage 10030 can include a memory 10032, such as a main memory, or other memory storage, and a storage unit 10036, both accessible to the processors 10010 such as via the bus 10002. The storage unit 10036 and memory 10032 store the instructions 10016 embodying any one or more of the methodologies or functions described herein. The instructions 10016 can also reside, completely or partially, within the memory 10032, within the storage unit 10036, within at least one of the processors 10010 (e.g., within the processor's cache memory), or any suitable combination thereof, during execution thereof by the machine 10000. Accordingly, the memory 10032, the storage unit 10036, and the memory of processors 10010 are examples of machine-readable media.

As used herein, "machine-readable medium" means a device able to store instructions and data temporarily or permanently and can include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 10016. The term "machine-readable medium" shall also be taken to include any medium, or combination of multiple media, that is capable of storing instructions (e.g., instructions 10016) for execution by a machine (e.g., machine 10000), such that the instructions, when executed by one or more processors of the machine 10000 (e.g., processors 10010), cause the machine 10000 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 10050 can include a wide variety of components to receive input, provide output, produce output, transmit information, exchange information, capture measurements, and so on. The specific I/O components 10050 that are included in a particular machine will depend on the type of machine. For example, portable machines such as mobile phones will likely include a touch input device or other such input mechanisms, while a headless server machine will likely not include such a touch input device. It will be appreciated that the I/O components 10050 can include many other components that are not shown in FIG. 100. The I/O components 10050 are grouped according to functionality merely for simplifying the following discussion and the grouping is in no way limiting. In various example embodiments, the I/O components 10050 can include output components 10052 and input components 10054. The output components 10052 can include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 10054 can include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 10050 can include biometric components 10056, motion components 10058, environmental components 10060, or position components 10062 among a wide array of other components. For example, the biometric components 10056 can include components to detect expressions (e.g., hand expressions, facial expressions, vocal expressions, body gestures, or eye tracking), measure physiologic signals (e.g., blood pressure, heart rate, body temperature, perspiration, or brain waves, neural activity, or muscle activity), identify a person (e.g., voice identification, retinal identification, facial identification, fingerprint identification, or electroencephalogram based identification), and the like.

The motion components 10058 can include acceleration sensor components (e.g., accelerometer), gravitation sensor components, rotation sensor components (e.g., gyroscope), and so forth. In one or more embodiments, one or more of the motion components 10058 can be incorporated with the external source 102 or the implantable device 110 and can be configured to detect motion or a physical activity level of a patient. Information about the patient's motion can be used in various ways, for example, to adjust a signal transmission characteristic (e.g., amplitude, frequency, etc.) when a physical relationship between the external source 102 and the implantable device 110 changes or shifts.

The environmental components 10060 can include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that can provide indications, measurements, or signals corresponding to a surrounding physical environment. The position components 10062 can include location sensor components (e.g., a Global Position System (GPS) receiver component), altitude sensor components (e.g., altimeters or barometers that detect air pressure from which altitude can be derived), orientation sensor components (e.g., magnetometers), and the like. In one or more embodiments, the I/O component(s) 10050 can be a part of the implantable device 110 and/or the external source 102.

Communication can be implemented using a wide variety of technologies. The I/O components 10050 can include communication components 10064 operable to couple the machine 10000 to a network 10080 or devices 10070 via coupling 10082 and coupling 10072 respectively. For example, the communication components 10064 can include a network interface component or other suitable device to interface with the network 10080. In further examples, communication components 10064 can include wired communication components, wireless communication components, cellular communication components, Near Field (nearfield) Communication (NFC) components, midfield communication components, far field communication components, and other communication components to provide communication via other modalities. The devices 10070 can be another machine or any of a wide variety of peripheral devices.

Moreover, the communication components 10064 can detect identifiers or include components operable to detect identifiers. For example, the communication components 10064 can include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information can be derived via the communication components 10064, such as, location via Internet Protocol (IP) geo-location, location via Wi-Fi® signal triangulation, location via detecting an NFC beacon signal that can indicate a particular location, and so forth.

In some embodiments, the systems comprise various features that are present as single features (as opposed to multiple features). For example, in one embodiment, the system includes a single external source and a single implantable device or stimulation device with a single antenna. Multiple features or components are provided in alternate embodiments.

In some embodiments, the system comprises one or more of the following: means for tissue stimulation (e.g., an implantable stimulation device), means for powering (e.g., a midfield powering device or midfield coupler), means for receiving (e.g., a receiver), means for transmitting (e.g., a transmitter), means for controlling (e.g., a processor or control unit), etc.

Although various general and specific embodiments are described herein, it will be evident that various modifications and changes can be made to these embodiments without departing from the broader scope of the present disclosure. Accordingly, the specification and drawings are to be regarded in an illustrative rather than a restrictive sense. The accompanying drawings that form a part of this application show, by way of illustration, and not of limitation, specific embodiments in which the subject matter can be practiced. The embodiments illustrated are described in sufficient detail to enable those skilled in the art to practice the teachings disclosed herein. Other embodiments can be used or derived therefrom, such that structural and logical substitutions and changes can be made without departing from the scope of this disclosure. This Detailed Description, therefore, is not to be taken in a limiting sense, and the scope of various embodiments is defined only by the appended claims, along with the full range of equivalents to which such claims are entitled. Specific embodiments or examples are illustrated and described herein, however; it should be appreciated that any arrangement calculated to achieve the same purpose can be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Each of these non-limiting examples or embodiments can stand on its own or can be combined in various permutations or combinations with one or more of the other examples or embodiments.

Example 1 includes an elongate implantable electrostimulation device comprising electrodes, a circuitry housing extending proximally from the electrodes, electrical stimulation circuitry situated in the circuitry housing, and an antenna situated more proximal than the circuitry housing. The device of example 1 can further include a migration mitigation component circumferentially situated about, separable from, and extending from the circuitry housing. The migration mitigation component can include a larger outer diameter than an outer diameter of the circuitry housing. The outer diameter of the migration mitigation component can be less than, or equal to, an outer diameter of a shaft of a component that introduces the device into a body during implant. The migration mitigation component can be a portion of a sheath through which the implantable device is implanted. The migration mitigation component can include one or more indents, protrusions, surface finishes, barbs, rings, through-holes or braids formed in an outer surface thereof. The migration mitigation component can be longitudinally compressible such that an outer diameter of the migration mitigation component increases responsive to longitudinal compression. The migration mitigation component can be separable from the circuitry housing and configured to be situated about the device after implant of the device. The migration mitigation component can be separable from the circuitry housing and the device can be configured to be situated into the migration mitigation component after implant of the migration mitigation component. The migration mitigation component can be separable from the circuitry housing and can include a compressible coil structure that, when compressed, includes a smaller outer diameter than when uncompressed.

Example 2 includes a system comprising the device of Example 1 and including an implantation sheath. The implantation sheath can include a lumen with an inner diameter greater than an outer diameter of the implantable device. The implantation sheath can be configured to guide the implantable device to an implant site in tissue. The migration mitigation component can be configured to receive and mechanically couple about the circuitry housing when the implantable device traverses a distal portion of the sheath. The migration mitigation component can be integrally formed with and comprise the distal portion of the sheath. The migration mitigation component can be configured to separate from a proximal portion of the sheath. The migration mitigation component can include a first radiopaque marker in a distal portion thereof. The sheath can include a second radiopaque marker more proximal than the distal portion of the sheath. The migration mitigation component includes one or more indents, protrusions, surface finishes, barbs, rings, or braids formed in an outer surface thereof. The migration mitigation component can be discrete and mechanically coupled to a distal end of the sheath. The sheath can be perforated at a breakaway junction between a proximal portion of the sheath and the migration mitigation component. The implantable device can comprise a frustoconical housing member, and wherein the migration mitigation component comprises an inner sidewall configured to interfere with the frustoconical housing member when the implantable device traverses the distal portion of the sheath.

Example 3 includes a method for implanting an implantable device. The method can include, using a push rod, advancing an implantable device through a lumen of a sheath toward an implant site. The method can include exerting force on a distal end of the sheath via the implantable device to cause a migration mitigation component to mechanically decouple from the sheath and couple about a housing of the implantable device. Exerting the force on the distal end of the sheath can include using a frustoconical outer housing portion of the implantable device to interfere with a mating frustoconical inner wall portion of the migration mitigation component. The migration mitigation component can be either (i) integrally formed with the sheath and more distal than a breakaway of the sheath or (ii) mechanically coupled to a distal end of the sheath. The migration mitigation component can comprise a distal portion of the sheath. The method can further include forming the sheath as a unitary structure that includes the migration mitigation component and a proximal sheath component, wherein forming the sheath includes providing a severable breakaway at a junction between the migration mitigation component and the proximal sheath component. The migration mitigation component can be configured to separate from the sheath responsive to the force applied at the distal end of the sheath. The method can further include fluoroscopically verifying a location of the migration mitigation component via a first radiopaque marker in a distal portion of the migration mitigation component. The method can further include fluoroscopically verifying a location of the implantable device via a second radiopaque marker on the sheath more proximal than migration mitigation component of the sheath. The migration mitigation component is discrete and mechanically coupled to a distal end of the sheath.

Example 4 can include a method for enhancing brain plasticity with respect to neural modulation therapy. The method can include providing a neural modulation therapy to a patient using an implanted midfield device, the neural modulation therapy based on one or more therapy parameters. The method can include prompting the patient for information about the therapy as provided. The method can include receiving a patient response. The method can include updating the one or more therapy parameters for the neural modulation therapy based on the patient response. Updating the therapy parameter can include changing one or more of an electrode configuration, an electrostimulation amplitude, an electrostimulation waveform, a therapy duty cycle, a therapy signal pulse width, and a therapy frequency of the neural modulation therapy. Receiving the patient response can include receiving information about whether the neural modulation therapy provided to the patient was felt or detected by the patient. Receiving the patient response can include receiving information about whether the patient experiences pain in coordination with the neural modulation therapy provided. Receiving the patient response can include receiving a qualitative indication about whether the neural modulation therapy as-provided as pleasant or unpleasant to the patient. The method can further include establishing a therapy diary for the patient by receiving the patient response to multiple different therapy events provided to the patient at respective different times. Prompting the patient for information can include prompting the patient before the neural modulation therapy is provided to the patient. Prompting the patient for information can include prompting the patient while the neural modulation therapy is provided to the patient. Prompting the patient for information can include prompting the patient after the neural modulation therapy is provided to the patient.

Example 5 can include a method for initializing an implanted device to provide an electrostimulation therapy at or near a sacral target in a patient body. The method can include selecting an electrostimulation signal amplitude that exceeds a perception threshold of the patient. The method can include selecting an electrostimulation electrode pair that provides a broadest electric field in the patient body. The method can include providing the electrostimulation therapy using the selected signal amplitude and using the selected electrostimulation electrode pair. The method can include receiving information about a patient response to the electrostimulation therapy as provided and based on the patient response, changing at least one of the signal amplitude and the electrode pair for a subsequent therapy. The method can include adjusting a power level of an external midfield transmitter that is in communication with the implanted device to balance heat generation and position of the external transmitter. The method can include changing a duty cycle of a therapy provided by the implanted device when a power level of an external transmitter exceeds a specified threshold power level. Changing the duty cycle can include decreasing a therapy on-time. The method can include providing an alert to the patient to change a position of the external transmitter.

Example 6 can include a system for providing electrostimulation to a patient body using electrodes in an epidural space. The system can include an implantable, wirelessly powered device comprising an electrode portion coupled to a housing portion. The electrode portion can be configured to be implanted inside the epidural space. The housing portion can be configured to be implanted outside of and adjacent to the epidural space. The housing portion can include one or more affixation features configured to maintain the implantable device in an implanted position such that the device resists migration toward or away from a spinal column. The housing portion can include tines configured to maintain the housing portion of the implantable device in an implanted position in muscle tissue between vertebrae. The housing portion can include tines configured to maintain the housing portion of the implantable device in an implanted position in muscle tissue adjacent to a vertebra. The system can further include an external midfield transmitter configured to communicate power signals to the implantable device when the implantable device is implanted in the patient body. The electrode portion can be configured for implantation into the epidural space via a foramen. The electrode portion is configured to be implanted inside the epidural space adjacent to a neural therapy target, and wherein the housing portion is configured to be implanted between a pair of vertebrae nearest the neural therapy target. The system can further include an external wireless power transmitter in communication with the implantable device. The system can further include a garment configured to be worn by the patient, the garment configured to retain the wireless power transmitter at a body-external surface adjacent to the implantable device when the implantable device is implanted. The garment can include a pocket coupled to a body portion of the garment, the pocket is configured to hold the wireless power transmitter, and the garment comprises a fabric cavity configured to receive and retain the pocket.

Example 7 can include a method for ensuring a wireless therapy device will not prohibitively wander after implant. The method can include implanting a wireless therapy device in tissue. The method can include verifying a circuitry housing is situated at a posterior edge of a sacrum. The method can include verifying a specified portion of an electrode array is situated at an anterior edge of the sacrum. The specified portion can be a most proximal electrode. The specified portion can be between a most proximal electrode and a second most proximal electrode. Implanting the wireless therapy device can be performed via a sacral foramen. Verifying the circuitry housing is situated at the posterior edge can include using fluoroscopy to visually identify a placement of a fiducial marker on the circuitry housing relative to a first side of the sacrum of a patient. Verifying the electrode array is situated at a posterior edge of the sacrum includes using fluoroscopy to visually identify a placement of a fiducial marker on or associated with the electrode array relative to a second side of the sacrum of the patient. The method can further include determining an implantation depth of a proximal portion of the circuitry housing.

Example 8 can include an implantable device. The implantable device can include an antenna, a circuitry housing, circuitry in the circuitry housing and electrically coupled to the antenna, a body portion, and electrodes on the body portion and electrically coupled to the circuitry. The implantable device can include a connector collar between and mechanically connected to the body portion and the circuitry housing, the connector collar including a cylindrical outer perimeter. The connector collar can further include an inner frustoconical surface (in a distal end thereof). The connector collar can further include a cylindrical surface portion adjacent to (e.g., proximal to) the inner frustoconical surface. The implantable device can include a tine structure mechanically coupled between the connector collar and the body portion. The connector collar can include an inwardly extending tab that is configured to mate with a corresponding detent in the tine structure. The connector collar can include a material that is less flexible than the body portion and more flexible than the connector collar. The connector collar can be adhered to the body portion and the circuitry housing, and wherein one or more electrode conductors extend through the connector collar. The connector collar can include one or more through-holes, and wherein the implantable device further comprises a dielectric filler received via the one or more through-holes. The connector collar can include one or more sight holes on a proximal side thereof, the sight holes configured to allow visual verification of one or more electrical connections inside of the connector collar.

Example 9 can include a method for forming an implantable device with improved strain relief. The method can include receiving a tine assembly over a portion of an elongate electrode array. The method can include coupling leads from the electrode array with electrostimulation circuitry in a circuitry housing. The method can include receiving a connector collar over a portion of the tine assembly. The method can include filling an interior portion of the connector collar with a dielectric filler. The method can further include mechanically coupling corresponding mating features of the connector collar and the circuitry housing. The method can further include mechanically coupling corresponding mating features of the connector collar and the tine assembly. Mechanically coupling the corresponding mating features can include receiving, in a detent in the tine structure, an inwardly extending tab of the connector collar. Coupling the leads from the electrode array with electrostimulation circuitry in the circuitry housing can include using laser welding to couple respective electrically conductive collars about the leads and from the electrode array and leads from the electrostimulation circuitry. Laser welding can occur via one or more sight hole in the connector collar.

Example 10 includes a garment. The garment can include a body portion including layers of one or more pieces of fabric and an access port providing access to a space between two of the layers of the fabric. The garment can include an enclosure attached to the body portion at an attachment point such that the enclosure is removable from the space via the access port and the enclosure is configured to be situated inside the space via the access port. The enclosure can include a top edge and an opposing bottom edge connected by two opposing sides, and a relative physical position of the top edge and the bottom edge is the same when (i) the garment is worn, and the enclosure is situated inside the space and (ii) the garment is worn, and the enclosure is situated outside the space. The enclosure can be removable from the space via the access port without exposing an item situated in the enclosure during removal. The access port can include an opening in an external layer of the layers. The attachment point can be substantially parallel to the opening. The attachment point can be accessible through the access port. The enclosure can include a stretchable material. The enclosure can include a fabric mesh. The one or more layers of fabric can include a same or different stretchable and bendable material. The attachment point can configure the enclosure to rest directly over a point on a surface of skin of a user that is closest to a specified foramen of the user, such as when the garment is worn by the user. The garment can be underwear. The underwear can include a stretchable and bendable band at a waist-opening of the underwear, and wherein the attachment point is coupled to the stretchable and bendable band. The stretchable and bendable band can extend around less than half of the waist-opening of the underwear. The garment can be a band. The enclosure can be tapered to be smaller at the attachment point than elsewhere. The enclosure can have three to five degrees of freedom with respect to the body portion when removed from the space. The enclosure can be attached so as to have five degrees of freedom including rotation about three perpendicular axes and translation along two of those three axes. The garment can include a thermal protective material situated inside the enclosure. The thermal protective material can be situated to protect skin of a user from heat produced by an electronic component situated in the enclosure. The garment can include a dielectric material situated in contact with the thermal protective material on a side of the thermal protective material opposite skin of a user when the garment is worn.

Example 11 can include an underwear garment comprising a body portion including two or more fabric layers, and an opening in an exposed layer of the fabric layers providing access to a space between two of the fabric layers. The underwear garment can include an enclosure including a top edge and a bottom edge connected by front and back side panels, the enclosure attached to the body portion at an attachment region and the enclosure configured to be inserted into or removed from the space via the opening and the enclosure further configured such that a relative physical position of the top edge and the bottom edge is the same when (i) the enclosure is situated inside the space and (ii) the enclosure is situated outside the space to provide user access to contents of the enclosure, wherein the attachment region is substantially parallel to the opening, and wherein the enclosure is attached to the body portion such that the enclosure is disposed adjacent to a surface of skin of a user that is closest to a specified foramen of the user when the underwear is worn by the user. The enclosure can have three to five degrees of freedom when attached to the body portion and removed from the space. The enclosure can have five degrees of freedom including rotation about three perpendicular axes and translation along two of those three axes. The underwear garment can include a thermal protective material situated inside the enclosure adjacent to the side panel that is configured to be worn closest to the surface of the skin of the user when the enclosure is inside the space. The thermal protective material can be configured to insulate skin of a user from heat produced by an electronic component situated in the enclosure. The underwear garment can include a dielectric material situated in contact with the thermal protective material on a side of the thermal protective material opposite the surface of the skin of the user when the garment is worn.

Example 12 can include a medical device. The medical device can include a garment configured to be worn about a groin area of a user. The garment can include multiple fabric layers configured to provide an inter-layer cavity accessible via an opening between the layers. The garment can include a device enclosure configured to be fixedly coupled, along a side portion of the enclosure, with a body portion of the garment, wherein the inter-layer cavity is configured to receive and retain the enclosure therein, wherein the enclosure is configured to be removed from the inter-layer cavity to permit user access to contents of the enclosure, and wherein the inter-layer cavity inhibits user access to contents of the enclosure when the enclosure is inside the inter-layer cavity. The medical device can include a wireless power transmitter. The device enclosure can be configured to receive and retain the wireless power transmitter when the enclosure is inside the inter-layer cavity and when the enclosure is outside of the inter-layer cavity. The enclosure can further include an insulator coupled to a skin-side surface of the enclosure. The insulator can include a thermal insulator and can be configured to inhibit heat transfer from the wireless power transmitter to the user. The insulator can include a dielectric member configured to maintain a specified spacing distance between an emissive surface of the wireless power transmitter and a surface of the skin of the user. The device enclosure can include an opening configured to admit the wireless power transmitter, and the device enclosure further includes a closure mechanism to secure the opening.

Example 13 can include a method for electrostimulation with sensor feedback. The method can include providing, by a (electrical power) source external to a patient, a first stimulation command to a neurostimulation device implanted in the patient that causes the neurostimulation device to generate first electrical stimulation with first electrical stimulation parameters. The method can include receiving, by the source, sensor data from sensor circuitry mechanically coupled to the patient. The method can include determining, by the source, whether the sensor data indicates a condition of the patient is improving or declining. The method can include providing, by the source, a second stimulation command to the neurostimulation device that causes the neurostimulation device to generate second electrical stimulation with second electrical stimulation parameters, the second electrical stimulation parameters including at least one parameter different than the parameters of the first electrical stimulation parameters. The first and second stimulation parameters can include one or more of a frequency, amplitude, time between pulses, or number of pulses. The sensor circuitry can include one or more of a force, pressure, temperature, capacitance, magnetic field, resistivity, salinity, moisture, or oxygenation sensor. Determining whether the condition of the patient is improving or getting worse can include determining one or more of a force, pressure, temperature, capacitance, magnetic field, resistivity, salinity, moisture, or oxygenation is increasing or decreasing. The condition can include neuropathy and the sensor circuitry includes one or more of a force or motion sensor situated under a foot of the patient.

Example 14 can include a system with improved fixation for an implantable device. The system can include an implantable electrostimulation device. The system can include an introducer configured to deliver the electrostimulation device to a target location inside a patient body. The introducer can include a migration mitigation component configured to couple with the electrostimulation device. The migration mitigation component can be configured to receive and couple with the electrostimulation device at the target location inside the patient body. The introducer can include a sheath, and wherein the sheath and the migration mitigation component have the same outer diameter. The sheath can include a proximal portion of the introducer and the migration mitigation component comprises a distal portion of the introducer, and wherein the sheath and migration mitigation component are separable at a breakaway junction. The breakaway junction can include a perforation in a sidewall of an elongate portion of the introducer. The introducer can include a sheath in which, or through which, the migration mitigation component and the electrostimulation device are configured to travel. The implantable electrostimulation device can include multiple electrodes, a circuitry housing extending proximally from the electrodes, electrical stimulation circuitry inside the circuitry housing, and an antenna on a proximal side of the circuitry housing. The migration mitigation component can be coupled to the electrostimulation device at the circuitry housing. The migration mitigation component can be coupled to the electrostimulation device at the antenna. The migration mitigation component can be coupled circumferentially about the circuitry housing. The electrostimulation device can be configured to travel through a sheath portion of the introducer. The migration mitigation component can include a distal portion of the introducer. The migration mitigation component can be configured to arrest travel of the electrostimulation device through a distal end of the introducer. The migration mitigation component can include a frustoconical inner wall portion, wherein the electrostimulation device comprises a frustoconical outer wall portion, and wherein the inner wall portion of the migration mitigation component is configured to couple with the outer wall portion of the electrostimulation device when the migration mitigation component arrests travel of the electrostimulation device through the distal end of the introducer. The migration mitigation component can include an outer surface that includes one or more of indents, protrusions, barbs, rings, fan blades, through-holes, tines, or braids. The migration mitigation component can be longitudinally contractible and an outer diameter of at least a portion of the migration mitigation component can be configured to increase in response to longitudinal contraction of the migration mitigation component. The electrostimulation device can be configured to be inserted through the migration mitigation component after implantation of the migration mitigation component.

The device of Example 1 or system 14 can be used in the method of any of Examples 3-5, 7, 9, and 13. The device or migration mitigation component of any of the Examples can be implanted using the push rod, sheath, introducer or a combination thereof of one of Examples 1-3 and 14. The method of Example 3 can include using the device of Examples 1, 2, or 14, migration mitigation component of Examples 1, 2, or 14, or sheath of Example 2 or 14. Example 4 can be performed using the device of one of Examples 1-3 or 14. Example 5 can be performed using the device of one of Examples 1-3 or 14. The system of Example 6 can include the implantable device or the migration mitigation component, of one of Examples 1-3 or 14. The method of one of Examples 4-5 can be performed using the system of Example 6. Example 3 and Example 6 can be performed in conjunction. Example 7 can be performed using the device, migration mitigation component, sheath, or push rod of one of Examples 1-3 or 14. The device of one of Examples 1-3 or 14 can include the connector collar, tine structure, circuitry housing, or body portion of the implantable device of Example 8. The device of one of Examples 1-3 can include the implantable device formed using the method of Example 9. An external power source of any of the Examples 1-14 can be situated in the enclosure of the garment of each of Examples 10-12. The method of Example 13 can be performed using the device of one of Examples 1-9 or 14.

The above detailed description includes references to the accompanying drawings, which form a part of the detailed description. The drawings show, by way of illustration, specific embodiments in which methods, apparatuses, and systems discussed herein can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 300 Hz" includes "300 Hz." Terms or phrases preceded by a term such as "substantially" or "generally" include the recited term or phrase. For example, "substantially parallel" includes "parallel" and "generally cylindrical" includes cylindrical.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention(s) and embodiments should be determined with reference to the appended claims, along with the full scope of equivalents to which such claims are entitled.

The stimulation devices, sources, systems, and methods discussed above can be used alone or can be combined with one or more other aspects of this disclosure. For example, embodiments can be used for or in combination with stimulation of dorsal root ganglion as described in Appendix B or can be used with stimulation for pain and inflammation as described in Appendix A.

What is claimed is:

1. A system comprising:

an implantable electrostimulation device; and an introducer including an inner sidewall that defines a lumen extending through the introducer, the introducer configured to receive the implantable electrostimulation device in a proximal end of the lumen and deliver the electrostimulation device to a target location inside a patient body at a distal portion of the lumen, wherein the introducer comprises a migration mitigation component integrally formed with the introducer, in a distal portion of the introducer, and including the lumen extending therethrough, the migration mitigation component i) configured to directly mechanically connect with an outer surface of the electrostimulation device and arrest travel of the electrostimulation device through a distal end of the distal portion of the introducer and (ii) is longitudinally contractible and an outer diameter of at least a portion of the migration mitigation component is configured to increase in response to longitudinal contraction of the migration mitigation component.

2. The system of claim 1, wherein the migration mitigation component is configured to receive and couple with the electrostimulation device at the target location inside the patient body.

3. The system of claim 1, wherein the introducer comprises a sheath, and wherein the sheath and the migration mitigation component have a same outer diameter.

4. The system of claim 3, wherein the sheath comprises a proximal portion of the introducer and the migration mitigation component comprises the distal portion of the introducer, and wherein the sheath and migration mitigation component are separable at a breakaway junction.

5. The system of claim 4, wherein the breakaway junction comprises a perforation in a sidewall of an elongate portion of the introducer.

6. The system of claim 1, wherein the implantable electrostimulation device comprises:

multiple electrodes;

a circuitry housing extending proximally from the electrodes;

electrical stimulation circuitry inside the circuitry housing; and an antenna on a proximal side of the circuitry housing.

7. The system of claim 6, wherein the migration mitigation component is coupled to the electrostimulation device at the circuitry housing.

8. The system of claim 7, wherein the migration mitigation component is coupled circumferentially about the circuitry housing.

9. The system of claim 6, wherein the migration mitigation component is coupled to the electrostimulation device at the antenna.

10. The system of claim 1, wherein the migration mitigation component comprises a frustoconical inner wall portion, wherein the electrostimulation device comprises a frustoconical outer wall portion, and wherein the inner wall portion of the migration mitigation component is configured to couple with the outer wall portion of the electrostimulation device when the migration mitigation component arrests travel of the electrostimulation device through the distal end of the introducer.

11. The system of claim 1, wherein the migration mitigation component includes an outer surface comprises one or more of indents, protrusions, barbs, rings, fan blades, through-holes, tines, or braids.

12. The system of claim 1, wherein the electrostimulation device is configured to be inserted into the migration mitigation component after implantation of the migration mitigation component.

13. A system comprising:

an implantable electrostimulation device comprising a frustoconical outer wall portion; and an introducer including an inner sidewall that defines a lumen extending through the introducer, the introducer configured to receive the implantable electrostimulation device in a proximal end of the lumen and deliver the electrostimulation device to a target location inside a patient body at a distal portion of the lumen, wherein the introducer comprises a migration mitigation component integrally formed with the introducer, in a distal portion of the introducer, and including the lumen extending therethrough, the migration mitigation component configured to directly mechanically connect with an outer surface of the electrostimulation device and arrest travel of the electrostimulation device through a distal end of the distal portion of the introducer, and the migration mitigation component comprises a frustoconical inner wall portion, the inner wall portion of the migration mitigation component is configured to couple with the outer wall portion of the electrostimulation device when the migration mitigation component arrests travel of the electrostimulation device through the distal end of the introducer.

* * * * *